(12) United States Patent
Monroe

(10) Patent No.: US 7,640,083 B2
(45) Date of Patent: Dec. 29, 2009

(54) RECORD AND PLAYBACK SYSTEM FOR AIRCRAFT

(76) Inventor: David A. Monroe, 7800 IH-10 W., #700, San Antonio, TX (US) 78230

( * ) Notice: Subject to any disclaimer, the term of this patent is extended or adjusted under 35 U.S.C. 154(b) by 662 days.

(21) Appl. No.: 10/719,796

(22) Filed: Nov. 21, 2003

(65) Prior Publication Data

US 2004/0230352 A1    Nov. 18, 2004

Related U.S. Application Data

(63) Continuation of application No. 10/719,976, filed on Nov. 21, 2003.

(60) Provisional application No. 60/428,386, filed on Nov. 22, 2002.

(51) Int. Cl.
  *G01C 5/00* (2006.01)
  *G05D 1/06* (2006.01)

(52) U.S. Cl. .................. 701/9; 701/3; 701/4; 701/5; 701/7; 701/8; 701/10; 701/14; 340/937; 340/945; 340/988; 340/539.1; 244/194

(58) Field of Classification Search .................. 701/3–5, 701/7–10, 14, 35; 340/937, 945, 539.1, 3.1, 340/500, 988; 386/E5.001; 244/194
  See application file for complete search history.

(56) References Cited

U.S. PATENT DOCUMENTS 3,256,386 A   6/1966  Morchand .................. 348/485
3,688,029 A * 8/1972  Bartoe et al. .................. 348/81
4,163,283 A   7/1979  Darby
4,179,695 A   12/1979 Levine et al.

(Continued)

FOREIGN PATENT DOCUMENTS

EP            209397           1/1987

(Continued)

OTHER PUBLICATIONS

M. J. Bos, ICAF 2009, Bridging the Gap between Theory and Operational Practice; Proceedings of the 25th Symposium of the International Committee on Aeronautical Fatigue, Rotterdam, The Netherlands, May 27-29, 2009 - 10.1007/978-90-481-2746-7_67.*

(Continued)

*Primary Examiner*—Cuong H Nguyen

(57) ABSTRACT

Multiple data and images are multiplexed and sequenced in order to minimize the recording and monitoring hardware required to process the images, providing a detailed record of an event, greatly enhancing event reconstruction efforts. The multi-media safety and surveillance system for aircraft incorporates a plurality of strategically spaced sensors including video imaging generators for monitoring critical components and critical areas of both the interior and the exterior of the aircraft. The captured data and images are recorded and may be transmitted to ground control stations for real time or near real time surveillance. The system includes a plurality of strategically located video image sensors such as, by way of example, analog and/or digital video cameras, a video data recorder (VDR) and a pilot display module (MCDU or MIDU). All data is in recorded in an IP format. The IP encoder may be an integral component of the VDR, or the data may be transmitted in an IP format from the data generator device.

24 Claims, 54 Drawing Sheets

U.S. PATENT DOCUMENTS

| | | | |
|---|---|---|---|
| 4,197,536 A | 4/1980 | Levine | |
| 4,516,125 A | 5/1985 | Schwab et al. | |
| 4,831,438 A | 5/1989 | Bellman, Jr. et al. | 348/148 |
| 4,845,629 A | 7/1989 | Murga | |
| 4,857,912 A | 8/1989 | Everett, Jr. et al. | |
| 4,891,650 A | 1/1990 | Sheffer | |
| 4,910,692 A | 3/1990 | Outram | |
| 5,027,104 A | 6/1991 | Reid | |
| 5,027,114 A | 6/1991 | Kawashima et al. | |
| 5,091,780 A | 2/1992 | Pomerleau | |
| 5,109,278 A | 4/1992 | Erickson | |
| 5,111,291 A | 5/1992 | Erickson | |
| 5,166,746 A | 11/1992 | Sato et al. | |
| 5,166,789 A | 11/1992 | Myrick | 348/144 |
| 5,191,412 A | 3/1993 | Thomson | 348/148 |
| 5,218,367 A | 6/1993 | Sheffer et al. | |
| 5,243,340 A | 9/1993 | Norman et al. | |
| 5,243,530 A | 9/1993 | Stanifer et al. | |
| 5,268,698 A | 12/1993 | Smith, Sr. et al. | |
| 5,283,643 A | 2/1994 | Fujimoto | 348/143 |
| 5,321,615 A | 6/1994 | Frisbie et al. | |
| 5,334,982 A | 8/1994 | Owen | |
| 5,341,194 A | 8/1994 | Haneda et al. | |
| 5,351,194 A | 9/1994 | Ross et al. | |
| 5,400,031 A | 3/1995 | Fitts | |
| 5,408,330 A | 4/1995 | Squicciarini et al. | |
| 5,432,838 A | 7/1995 | Purchase | |
| 5,440,337 A | 8/1995 | Henderson et al. | |
| 5,440,343 A | 8/1995 | Parulski | |
| 5,448,243 A | 9/1995 | Bethke et al. | |
| 5,463,595 A | 10/1995 | Rodhall et al. | |
| 5,469,371 A | 11/1995 | Bass | |
| 5,497,149 A | 3/1996 | Fast | |
| 5,508,736 A | 4/1996 | Cooper | |
| 5,509,009 A | 4/1996 | Laycock | |
| 5,530,440 A | 6/1996 | Danzer et al. | |
| 5,553,609 A | 9/1996 | Chen et al. | |
| 5,557,254 A | 9/1996 | Johnson et al. | |
| 5,557,278 A | 9/1996 | Piccirillo et al. | |
| 5,596,494 A | 1/1997 | Kuo | 702/2 |
| 5,598,167 A | 1/1997 | Zijderhand | |
| 5,604,534 A | 2/1997 | Hedges et al. | 348/144 |
| 5,612,668 A | 3/1997 | Scott | |
| 5,625,409 A | 4/1997 | Rosier et al. | 348/117 |
| 5,627,753 A | 5/1997 | Brankin et al. | |
| 5,629,691 A | 5/1997 | Jain | |
| 5,636,122 A | 6/1997 | Shah et al. | |
| 5,642,285 A | 6/1997 | Woo | |
| 5,666,157 A | 9/1997 | Aviv | |
| 5,670,961 A | 9/1997 | Tomita et al. | |
| 5,677,979 A | 10/1997 | Squicciarini | |
| 5,689,442 A | 11/1997 | Swanson | |
| 5,712,679 A | 1/1998 | Coles | |
| 5,712,899 A | 1/1998 | Pace, II | |
| 5,714,948 A | 2/1998 | Farmakis et al. | |
| 5,742,336 A | 4/1998 | Lee | |
| 5,751,346 A | 5/1998 | Dozier | |
| 5,777,551 A | 7/1998 | Hess | |
| 5,777,580 A | 7/1998 | Janky et al. | |
| 5,793,416 A | 8/1998 | Rostoker et al. | |
| 5,825,283 A | 10/1998 | Camhi | |
| 5,835,059 A | 11/1998 | Nadel et al. | |
| 5,850,180 A | 12/1998 | Hess | |
| 5,867,804 A | 2/1999 | Pilley et al. | |
| 5,917,405 A | 6/1999 | Joao | |
| 5,926,210 A * | 7/1999 | Hackett et al. | 348/158 |
| 5,933,098 A | 8/1999 | Haxton | |
| 5,938,706 A | 8/1999 | Feldman | |
| 5,974,158 A | 10/1999 | Auty et al. | |
| 5,983,161 A | 11/1999 | Lemelson et al. | |
| 5,999,116 A | 12/1999 | Evers | |
| 6,002,427 A | 12/1999 | Kipust | |
| 6,009,356 A | 12/1999 | Monroe | |
| 6,067,571 A | 5/2000 | Igarashi et al. | |
| 6,069,655 A | 5/2000 | Seeley | |
| 6,078,850 A | 6/2000 | Kane et al. | |
| 6,084,510 A | 7/2000 | Lemelson et al. | |
| 6,092,008 A | 7/2000 | Bateman | |
| 6,100,964 A | 8/2000 | De Cremiers | |
| 6,133,941 A | 10/2000 | Ono | |
| 6,154,658 A | 11/2000 | Caci | |
| 6,157,317 A | 12/2000 | Walker | |
| 6,181,373 B1 | 1/2001 | Coles | |
| 6,195,609 B1 | 2/2001 | Pilley et al. | |
| 6,226,031 B1 | 5/2001 | Barraclough et al. | |
| 6,246,320 B1 | 6/2001 | Monroe | |
| 6,259,475 B1 | 7/2001 | Ramachandran et al. | |
| 6,275,231 B1 | 8/2001 | Obradovich | |
| 6,278,965 B1 | 8/2001 | Glass et al. | |
| 6,282,488 B1 | 8/2001 | Castor et al. | |
| 6,292,098 B1 | 9/2001 | Ebata | |
| 6,356,625 B1 | 3/2002 | Castelani | |
| 6,366,311 B1 | 4/2002 | Monroe | 348/148 |
| 6,385,772 B1 | 5/2002 | Courtney | |
| 6,424,370 B1 | 7/2002 | Courtney | |
| 6,462,697 B1 | 10/2002 | Klamer et al. | |
| 6,476,858 B1 | 11/2002 | Ramirez Diaz et al. | |
| 6,504,479 B1 | 1/2003 | Lemons | |
| 6,522,532 B2 | 2/2003 | Liao et al. | |
| 6,525,761 B2 | 2/2003 | Sato et al. | |
| 6,545,601 B1 * | 4/2003 | Monroe | 340/521 |
| 6,549,130 B1 | 4/2003 | Joao | |
| 6,549,162 B1 * | 4/2003 | Gage et al. | 342/353 |
| 6,556,241 B1 | 4/2003 | Yoshimura et al. | |
| 6,570,610 B1 | 5/2003 | Kipust | |
| 6,628,835 B1 | 9/2003 | Brill | |
| 6,646,676 B1 | 11/2003 | DaGrace | |
| 6,662,649 B1 | 12/2003 | Knight et al. | |
| 6,675,386 B1 | 1/2004 | Hendricks et al. | |
| 6,698,021 B1 | 2/2004 | Amini | |
| 6,720,990 B1 | 4/2004 | Walker et al. | |
| 6,732,027 B2 * | 5/2004 | Betters et al. | 701/29 |
| 7,113,971 B1 | 9/2006 | Ohi et al. | |
| 7,480,420 B2 * | 1/2009 | Wang | 382/274 |
| 2002/0029099 A1 * | 3/2002 | Gardner | 701/3 |
| 2003/0052798 A1 * | 3/2003 | Hanson | 340/945 |
| 2003/0063004 A1 * | 4/2003 | Anthony et al. | 340/574 |
| 2003/0071899 A1 | 4/2003 | Joao | |
| 2003/0097661 A1 * | 5/2003 | Li et al. | 725/109 |
| 2003/0185296 A1 * | 10/2003 | Masten, Jr. | 375/240.01 |
| 2005/0007988 A1 * | 1/2005 | Ferris et al. | 370/349 |
| 2005/0055727 A1 | 3/2005 | Creamer et al. | |
| 2005/0138083 A1 | 6/2005 | Rastegar | |
| 2007/0025259 A1 * | 2/2007 | Reinhold | 370/241 |
| 2008/0039967 A1 * | 2/2008 | Sherwood | 700/94 |

FOREIGN PATENT DOCUMENTS

| | | |
|---|---|---|
| EP | 220752 | 5/1987 |
| EP | 232031 | 8/1987 |
| EP | 532110 | 3/1993 |
| EP | 209397 | 7/1993 |
| EP | 613109 | 8/1994 |
| EP | 613110 | 8/1994 |
| EP | 613111 | 8/1994 |
| EP | 744630 | 11/1996 |
| EP | 785536 | 7/1997 |
| EP | 1362431 A2 * | 11/2003 |
| GB | 2373685 A * | 9/2002 |
| JP | 6-301898 | 10/1994 |
| JP | 9-251599 | 9/1997 |
| JP | 9-282600 | 10/1997 |
| JP | HEI-10-66058 | 3/1998 |
| JP | A-10-155040 | 6/1998 |

| | | |
|---|---|---|
| JP | 9-251599 | 4/1999 |
| JP | 11-160424 | 6/1999 |
| JP | 11-180424 | 6/1999 |
| WO | WO90/04242 | 4/1990 |
| WO | WO95/27910 | 10/1995 |
| WO | WO96/12265 | 4/1996 |
| WO | WO97/37336 | 10/1997 |
| WO | WO9737336 | 10/1997 |
| WO | WO98/52174 | 11/1998 |
| WO | WO 2007016518 A2 * | 2/2007 |
| WO | WO 2008021091 A2 * | 2/2008 |

OTHER PUBLICATIONS

Cruz et al., "Capturing and Playing Multimedia Events with Streams," Proceedings ACM Multimedia, Oct. 1994, pp. 193-200, cited by other.*

TVX, Inc. Brochure entitled, "How Can A Device This Small Make Such A Huge Contributon To Your Security System?".*

TVX, Inc. Brochure entitled, "The TVX Camera-On-A-Chip System Inexpensively Transmits 4 Pictures Of What Caused The Alarm To A Monitoring Station In Less Than 20 Seconds!".*

Apr. 1966, Apollo Unified S-Band System, NASA-Goddard Space Flight Center, Greenbelt, Maryland.

Apr. 1966, Apollo Unified S-Band System, NASA-Goddard Space Flight Center, Greenbelt, Maryland.

Nov. 24, 1976, TELEXIS ViaNet General Information Booklet Version 1.3.

2000, ViaNet 3000 Administrator's Manual Version 1.1- NetXpress Video by Telexis, Kanata, Ontario, Canada.

1999 Vianet 3000 Operator Manual Version 1.0 - NetXpress Video by Telexis, Kanata, Ontario, Canada.

1999 ViaNet 3000 Administrator Manual Version 1.0 - NetXpress Video by Telexis, Kanata, Ontario, Canada.

1999 ViaNet 3000 Instruction Manual Operator's Revision 1 - NetXpress Video by Telexis, Kanata, Ontario, Canada.

* cited by examiner

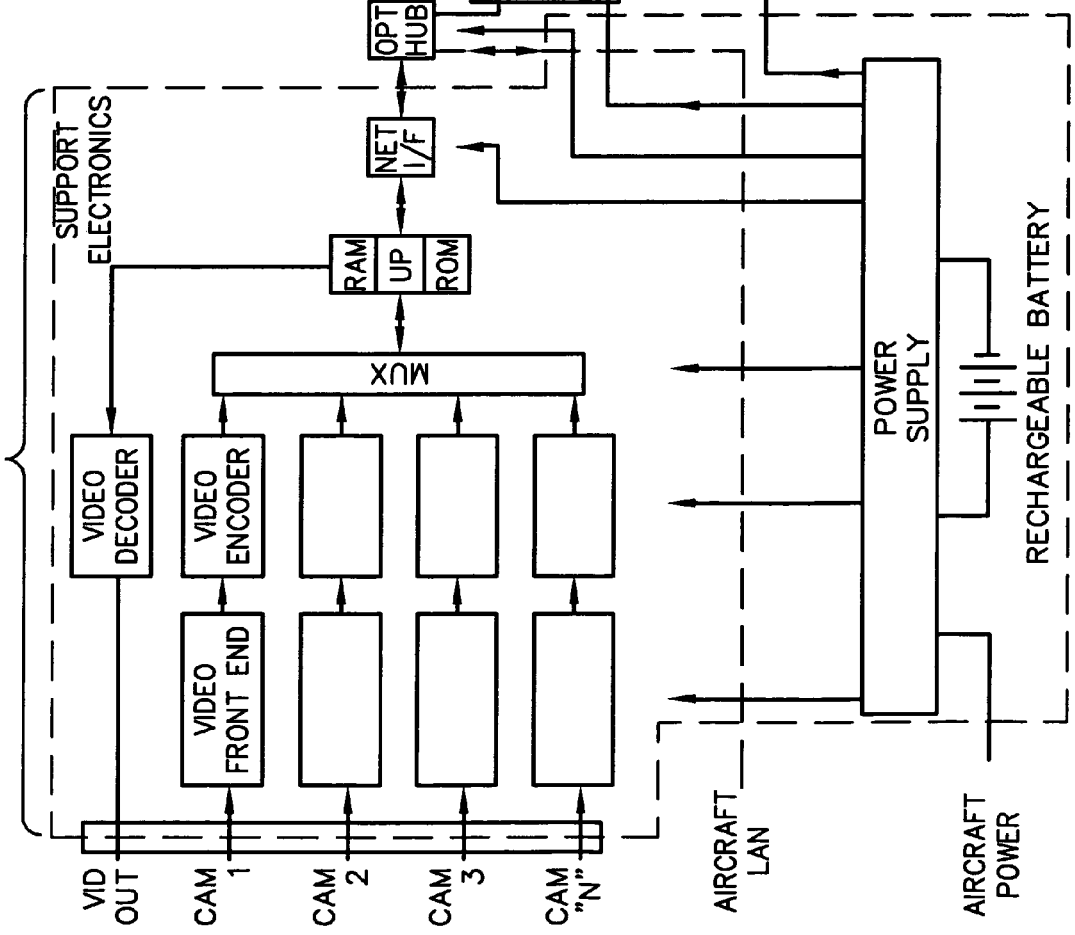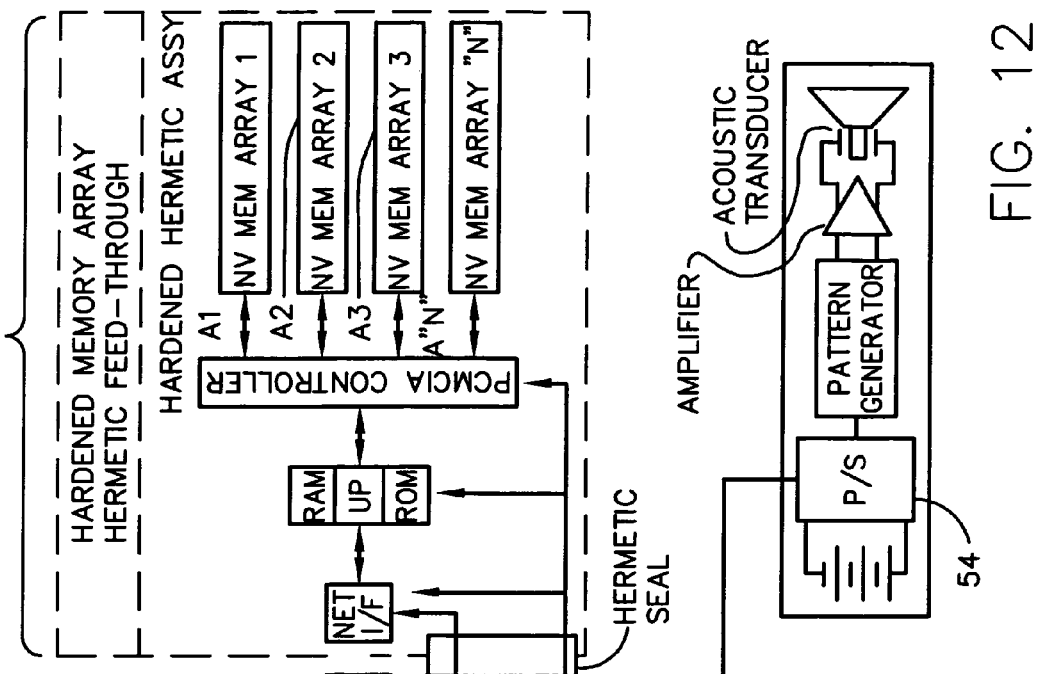

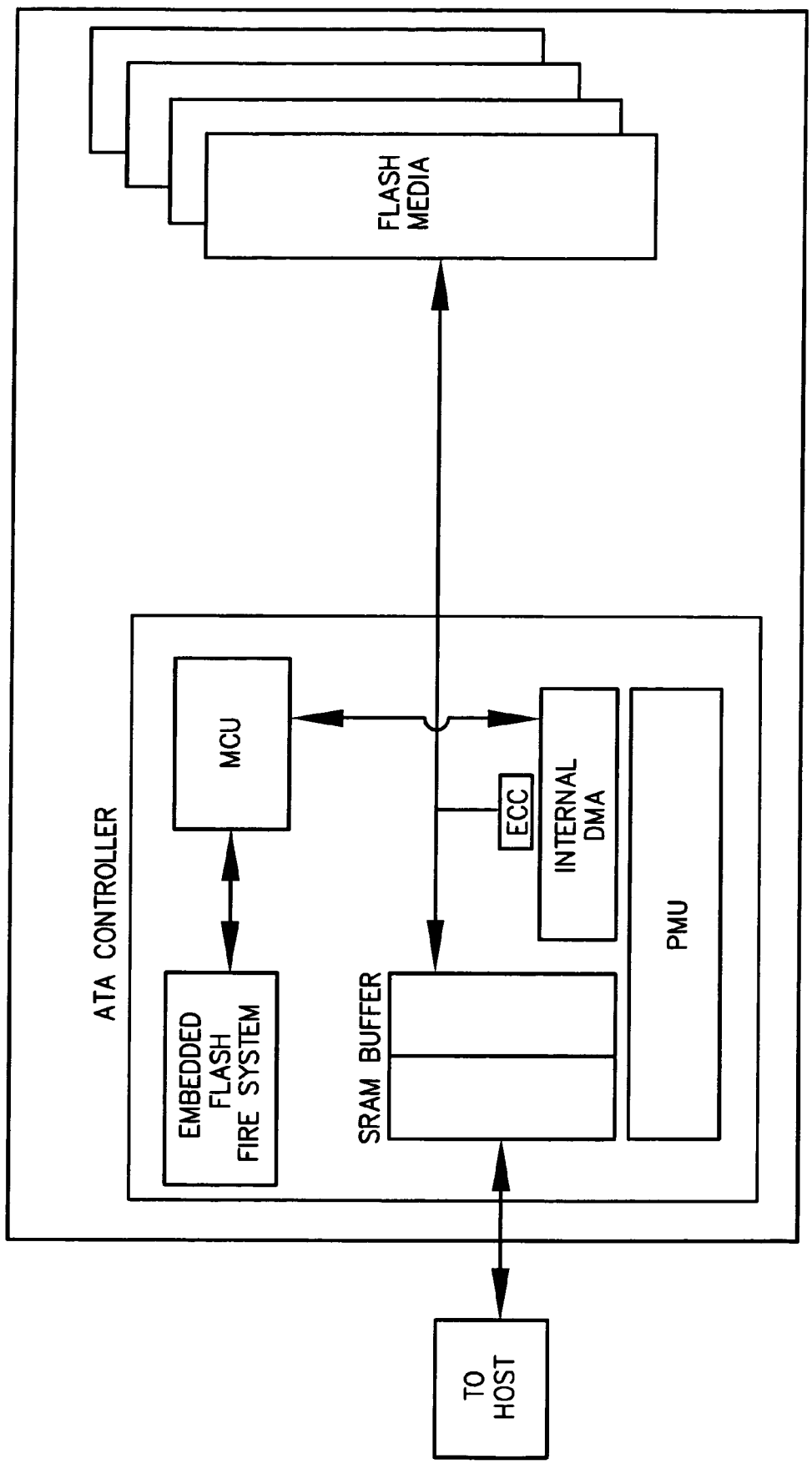

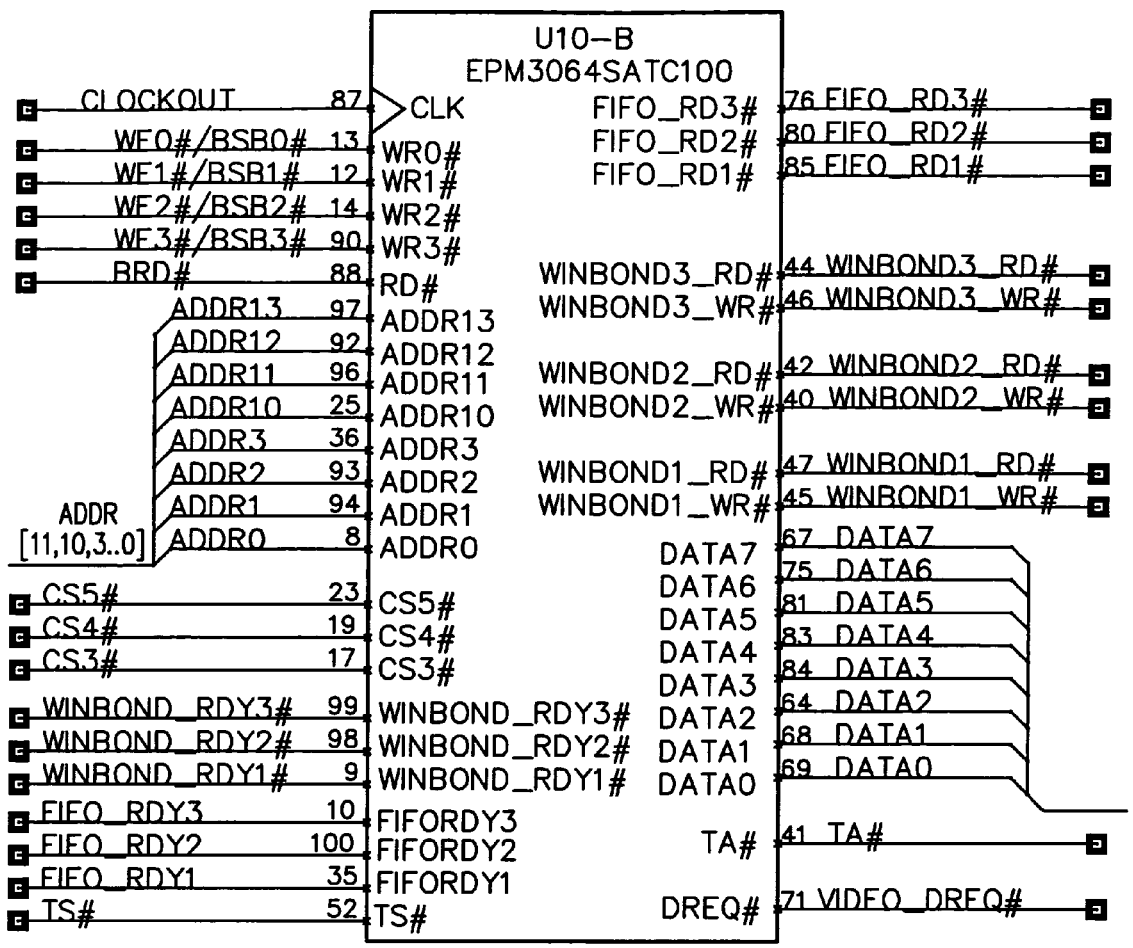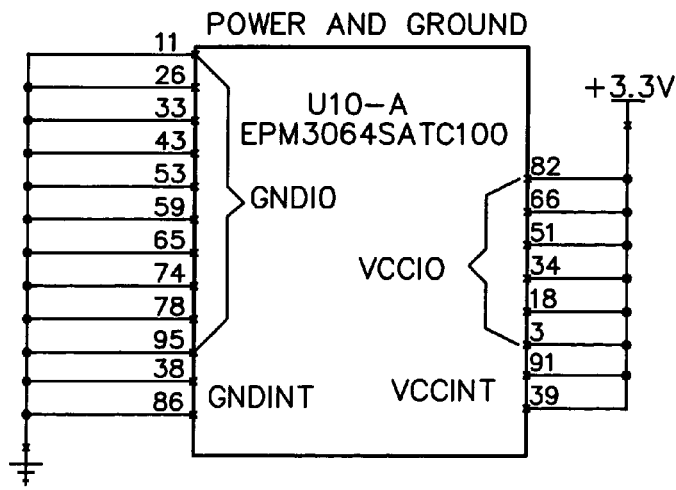
FIG. 160

RECORD AND PLAYBACK SYSTEM FOR AIRCRAFT

CROSS REFERENCE TO RELATED APPLICATION

This application is a continuation application of and claims the priority of U.S. Non-Provisional Patent Application Ser. No. 10/719,796 filed Nov. 21, 2003, which is incorporated herein by reference. This application likewise claims the priority of U.S. Provisional Application Ser. No. 60/428,386, filed Nov. 22, 2002.

BACKGROUND OF INVENTION

1. Field of Invention

The subject invention is generally related to safety and surveillance equipment for aircraft and is specifically directed to a comprehensive multi-media flight recording and playback system for commercial aircraft wherein data and/or video images may be collected, monitored, transmitted, stored and replayed for event reconstruction.

2. Discussion of the Prior Art

Aircraft safety is of ever increasing importance. This is particularly true with respect to commercial airlines as more and more people and freight are moved in this manner. The airways are becoming increasingly crowded with traffic. Global tracking systems are now in place to monitor the flight of the aircraft from the moment it lifts off until it safely lands at its destination. Radar and global positioning systems are commonplace both on the aircraft and at the ground tracking stations. All of these electronic systems have increased the overall safety record of commercial traffic to new standards as the number of miles flown continues to escalate at an alarming pace.

In addition, the on board avionics, including electronic monitoring and diagnostic equipment, particularly on large commercial jets, continues to evolve giving both the on board crew and the tracking station more complete, accurate and up-to-date information regarding the condition of the aircraft while in flight. Flight recorders long have been incorporated in order to provide a record of each flight and in order to provide critical information to aid in the determination of the causes of an accident or malfunction should one occur.

One of the greatest safety investigation inventions for the commercial airline industry has been the crash protected flight recorder, more commonly called the "Black Box." Today, flight recorders for accident investigation are mandatory pieces of equipment in civil aircraft. Flight recorders have changed in design and airline usefulness during the past 40 years.

Efforts to require crash-protected flight recorders date back to the 1940s. The introduction of Flight Data Recorders (FDR), however, experienced many delays, first being mandated in 1958. The initial requirement for these data recorders was to record the actual flight conditions of the aircraft, i.e., heading, altitude, airspeed, vertical accelerations, and time. These early devices had very limited recording capabilities. The five analog parameters mentioned above were embossed onto a metal foil, which was used only once. With just five parameters, however, there were not enough recorded data for meaningful accident investigation. Consequently, in 1987, these recorders became unacceptable to most government regulatory authorities and additional parameters were required.

Although most major airlines replaced these old technology recorders long before required by law, many of the first generation recorders are still flying in older model aircraft. The remainder of these foil recorders will soon be unusable, since the metal foil is being quickly depleted.

Further, the flight data alone cannot provide all accident information needed by investigators. An advanced technology covering the recording of sounds in the cockpit, crews' conversations, air traffic control communications and aircraft noises is required. This initiated development of the second next generation of recorders that use magnetic tape as the recording medium. The first product to use this new technology was the cockpit voice recorder (CVR). In 1965, all commercial operators were mandated to install a CVR, which would retain the last 30 minutes of crew voice communications and noises within the cockpit environment. The magnetic tape required very complex fire and crash protection.

The Fairchild CVR, Models A100 and A100A, manufactured by L-3 Communications Aviation Recorders, are examples of second generation recorders. These have become the most widely used CVR in the world and have now been in service for more than 30 years. More recently, this same "tape" technology has been expanded to the flight data recorder. This second-generation FDR records additional flight parameters while meeting higher crash and fire protection requirements than the first generation FDR's, including operational data for engines, flight controls, flaps and other operating components to fully assist accident investigators. By the mid 1980s, all newly Type Certified (TC) aircraft were being fitted with recorders that could capture between 17 to 32 parameters.

In 1990, the third generation Solid State Flight Data Recorder (SSFDR) became commercially practical. The SSFDR, Model F1000, was the first certified flight recorder to use this new technology. The Solid State CVR (SSCVR) became available in a 30-minute format in 1992 and in a two-hour format in 1995.

SUMMARY OF THE INVENTION

The subject invention is directed to a recording and playback system wherein data, video, audio and/or images are multiplexed and sequenced in order to provide a detailed record of the time of an event, the altitude and geographic location of the aircraft and the type and location of the event within the aircraft, greatly enhancing event reconstruction efforts. The terms VDR, Multimedia Flight Data Recorder, IP Data are used interchangeably to refer to this system. The system is a comprehensive multi-media safety and surveillance system, which in the preferred form provides both visual and audio information as well as critical data to the flight crew, and to a ground tracking station, and also permits recording the information and data generated during flight for archival purposes and for later playback, particularly useful in reconstructing catastrophic events. In one preferred embodiment, a plurality of sensor units, including at least one video image sensor/device, are placed strategically throughout the aircraft. For example, several video cameras may be placed such that the lens of each is aimed through an opening provided in the fuselage in order to provide video imaging of the engines, tail section, and landing gear and other functional components of the aircraft. Additional cameras may be placed throughout the interior of the aircraft on the flight deck, in the cargo hold, in the passenger cabin and other desired spaces. The data sensors/transducers, such as by way of example, the engine temperature sensor, oil pressure and hydraulic pressure sensors, strain gauges and the like, are also incorporated in the data collection system of the subject invention. Audio may also be digitized, such as cockpit audio, radio audio, and microphone audio, and stored in the data collection system. This can thus combine the function of the previous generation Cockpit Voice Recorder (CVR) into the Multimedia Flight Data Recorder (MFDR) of the subject invention.

In an additional preferred embodiment, the Multimedia Flight Data Recorder described by this invention also records data from conventional Flight Data Acquisition & Management System (FDAMS), Digital Flight Data Acquisition Unit (DFDAU), and Aircraft Condition Monitoring System (ACMS). These conventional systems would be interfaced with the I/P Flight Data Recorder of this invention utilizing I/P (Internet Protocol). The conventional systems above, typically interfaced with protocols ARINC 429, ARINC 573, ARINC 724, ARINC 724B, ARINC 739, ARINC 740 and the like, would be converted to I/P protocol for transmission to the Multimedia Flight Data Recorder of this invention. This provides a dramatic improvement in data collection techniques by utilizing highly flexible LAN techniques for the transmission of and storage of aircraft safety data. This converted data can be stored in conjunction with other LAN data such as streaming motion video, step video (still images), streaming audio and event data such as alarms.

In summary, the Multimedia Flight Data Recorder can record conventional flight data, video data, image data, audio data and event data in any selection or combination as communicated over the aircraft LAN to the Multimedia Flight Data Recorder. The Flight Data Recorder may also play back data simultaneously to recording operations, such as for reference to the pilots or to ground analysts during emergency situations.

The system may be hardwired in the aircraft, or may use wireless transmission and receiving systems. The wireless system is particularly useful for adapting the system as a retrofit on existing aircraft and also provides assurances against disruption of data transmission and collection during a catastrophic airframe failure. In the preferred embodiment, the wireless system is fully self-contained with each sensor unit having an independent power supply and where appropriate, a sensor light source. The ground link, monitoring and recording systems for collecting and transmitting the data are also self-contained. This assures that the system will continue to operate in the event of either a malfunction, such as a total power failure, or a structural failure of the aircraft causing a disruption in power source, power wiring or signaling wiring and will not disrupt the generation and collection of data and visual images.

A monitor may be provided on the flight deck and recorders may be placed in the tail section, as is common for flight data and voice recorders currently in use. The flight deck would have instant live access to all of the images as they are captured by the video cameras and/or flight sensors and the recorder would make an historic record of the images and data for archive purposes. Where random access recording techniques are used, such as, by way of example, digital random access memory storage devices, the flight deck and the ground station may also be able to search and retrieve stored information. For example, current hydraulic pressure of a component may be compared with the pressure of a past point in time to monitor rate of change.

Where desired, ground tracking or control stations would have selective access to the images on a near or real-time basis. In addition, the ground station could send video images to the aircraft flight deck monitors on a selective basis. That is, the ground tracking station will have the capability of interrogating the in-flight data, including video images, while the aircraft is in flight. Near real-time data can be received and historical data can be retrieved as well, when the random access storage device is utilized.

The plurality of sensors are synchronized through an on-board multiplexing system whereby the plurality of data, including visual image data, may be displayed, recorded, and/or transmitted with known time criteria for each element of data. In the preferred embodiment, the system is adapted for incorporating the data signal generated by the aircraft navigational data such as that provided by the on-board global positioning system for tracking the altitude, latitude and longitude coordinates synchronized with the collected data in order to provide accurate information of where the aircraft is in its flight plan when an incident occurs. A time or chronology signal may also be incorporated in the data scheme. Any signal that is capable of being captured and stored may be monitored in this manner. For example, radar images that are currently displayed on a cockpit monitor can also be transmitted to the ground and can be stored in the record of the "black box" recording system on board the aircraft. Transducer signals monitoring pressure system and engine components are also be collected for transmission and storage. Data generated by image sensors ranging from analog video cameras to digital cameras to infrared sensors and the like can be collected and distributed by the system. The system is particularly well suited for use in combination with forward linking infrared (FLIR) cameras for producing visual images in darkness. This would be particularly useful in determining the flight path of the aircraft, both on board and for later retrieval when incidents occur in low light level conditions. Some of these features are shown and described in my co-pending application entitled: "Record and Playback System for Aircraft", Ser. No. 09/257,765, filed on Feb. 25, 1999 and incorporated by reference herein.

The system of the subject invention provides a comprehensive multi-media data capture, display, transmission and storage surveillance system for the aircraft while in flight, with data readily accessible to both the flight crew and a ground tracking station. The system is particularly suited for providing data transmission over a Local Area Network (LAN) onboard the aircraft and in an IP (Internet Protocol) format and is adapted for merging both analog and digital legacy and state of the art systems into a comprehensive recording and playback system for aircraft.

In one embodiment of the invention, the capture, retrieval, monitor and archive system is installed utilizing a wireless transmitting/receiving system combined with a sensor in order to assure that transmission will not be lost in the event of a power shutdown or a structural failure causing possible open circuit conditions that could occur in a hard wired system. Such a system may be completely self-contained with an integrated power supply and an integrated illumination system in the case of a video sensor. The illumination system would provide lighting to permit capture of images in the event the aircraft power system fails. The communication between the sensor and the Multimedia Flight Data Recorder, in the preferred embodiment, would utilize the industry standards 802.11 or 802.11b or their predecessors. These wireless protocols are highly developed for small size, provide error correction protocol and sufficient bandwidth for video.

The system is of invaluable service to the flight crew and the ground tracking station, providing visual indication of such information as the operation of the landing gear, for example, or of an engine smoke condition, or of the presence of smoke or fire in the cargo hold. In addition, the system provides instant visual access to conditions in the passenger cabin or in the cargo hold. The ground or tracking station can relay video information directly to the crew in the event of certain conditions. For example, if a terrorist or terrorist group were on board, the ground crew would have access to visual information indicating the conditions in the passenger cabin and cockpit. This would permit the ground crew to ascertain the number of terrorists on board, the types of weapons carried and visual identification of the individuals without any communication from the flight crew and without any flight crew action. Such information is invaluable in determining the best course of action for dealing with such a crisis. Further, critical visual information can be transmitted to the flight crew for assisting the crew in dealing with the situation.

Of course, it is an important aspect of the invention that all of the collected data, including any video images, be recorded on the flight recorder to provide an historic video record of the flight. This is invaluable in reconstructing the cause of catastrophic occurrences during a flight.

In the preferred embodiment, the system includes a plurality of strategically located video image sensors such as, by way of example, analog and/or digital video cameras, a video data recorder and a pilot display module (MCDU or MIDU). In the preferred embodiment, all data is recorded in an IP format. The IP encoder may be an integral component of the recorder, or the data may be transmitted in an IP format from the data generator device. The recorder includes one or more non-volatile memory arrays for storing and processing the data. The recorder includes both wired and wireless network connectivity. In the preferred embodiment, the memory arrays are in a hardened hermetic assembly while other support electronics may be housed in a less rigorous assembly. An underwater beacon generator may be provided to assist in locating a downed recorder unit. The system is adapted for sending live signals directly to ground support via radio or satellite communications channels. The system also includes audio sensors and component monitoring sensor devices and can replace the Cockpit Voice Recorder (CVR) system where desired. The system is adapted for selectively transmitting all of the data on a near real time basis to a ground tracking station.

Discussion of Typical Data Storage Requirements:

Storage of typical flight data such as altitude, ground speed, air speed, engine parameters and the like does not consume much data storage capacity, even when samples are recorded every few seconds. Storage of streaming video is, however, intensive. Compression is utilized to reduce the bandwidth of full motion video from the raw bandwidth of 15 MBytePS to lesser rates from 128 KBytePS to 2 MPBytePS based on compression types and parameter selection. The most popular commercial video compression standards are now MPEG, the Motion Picture Experts Group. High-resolution still frame images, such as JPEG or wavelet, can be utilized to store higher quality images at a lower capture rate than full motion video. Images compressed to 16 KByte to 32 KByte have shown adequate quality for flight video collection. Combinations of full motion video at various frame rates and compression ratios and still frame imagery at various compression rates and intervals may be utilized to optimize image quality and storage requirements.

Solid-state non-volatile memory technology is quite dense, and is continuing to double in density every few years. One solid-state flash memory that can be utilized for this invention is the SST CompactFlash technology, which is currently available in a 256 MByte package that is approximately 1.5 inches square and 0.13 inches thick. An array of 16 of these modules will provide 4 GByte of storage, enough storage to record 16 cameras running at 2 FPS of high quality wavelet compression at 16 KBytes per image for over 2 hours in addition to storing flight data. The CompactFlash technology utilized in the preferred embodiment is that which is in the Silicon Storage Technology, Inc. model number SST48CF256.

The following applications are fully incorporated herein by reference:

| Ser. No. | Filing Date | U.S. Pat. No. |
| --- | --- | --- |
| 09/005,932 | Jan. 12, 1998 | |
| 09/005,931 | Jan. 12, 1998 | |
| 09/350,197 | Jul, 08, 1999 | |
| 09/006,073 | Jan. 12, 1998 | |
| 09/257,765 | Feb. 25, 1999 | |
| 09/257,769 | Feb. 25, 1999 | |
| 08/729,139 | Oct. 11, 1996 | |
| 08/745,536 | Nov. 12, 1996 | 6,009,356 |
| 08/738,487 | Oct. 28, 1996 | 5,798,458 |
| 09/005,892 | Jan. 12, 1998 | |
| 09/257,802 | Feb. 25, 1999 | |
| 09/257,766 | Feb. 25, 1999 | |
| 09/257,767 | Feb. 25, 1999 | |
| 09/257,720 | Feb. 25, 1999 | |

It is, therefore, an object and feature of the subject invention to provide a network compatible, comprehensive, multimedia data collection, storage and playback system for aircraft.

It is an additional object and feature of the subject invention to provide a video record of critical components and areas of an aircraft during flight for archival and retrieval purposes.

It is an object and feature of the subject invention to provide a video or other sensor record of surrounding periphery of the aircraft such that a missile attack to that aircraft can be recorded for identification.

It is yet another object and feature of the subject invention to provide apparatus for permitting ground personnel to receive near real-time video images, audio information and/or data relating to critical components and areas of an aircraft during flight.

It is a further object and feature of the subject invention to provide apparatus for permitting ground personnel to query, retrieve and receive historical video images, audio information and/or data relating to critical components and areas of an aircraft during flight It is a further object and feature of the subject invention to provide accurate information of where the aircraft is during a flight path when a specific visually captured image occurs.

It is a further object and feature of the subject invention to provide accurate information of where the aircraft is during a flight path when a specific event occurs.

It is also an object and feature of the subject invention to provide a system for linking recorded video images with an inertial navigation system such or other navigational data source such as, by way of example, a global positioning system for archival purposes.

It is still another object and feature of the invention to permit the monitoring, storing and retrieval of any of a variety of video images, audio signals and performance data by the tracking, surveillance and imaging equipment on board the aircraft.

It is an object and feature of the invention to convert on board navigation and safety equipment interface buses such as industry standard ARINC 429, ARINC 573, ARINC 724, ARINC 724B, ARINC 739, ARINC 740 to an I/P connection, such as Ethernet 10/100 BASE-T and the like, for distribution throughout the aircraft and to the flight recorder.

It is a further object and feature of the invention to convert on board navigation and safety equipment data streams and files such are typically communicated on industry standard ARINC 429, ARINC 573, ARINC 724, ARINC 724B, ARINC 739, ARINC 740 formats, to data files communicated over an I/P connection, such as Ethernet 10/100 BASE-T and the like, for recording on an industry standard file server architecture, such as Unix or Windows NT architecture, within a hardened Multimedia Flight Data Recorder.

It is an object and feature of the invention to power one or more remote sensors with a standby battery that is in wireless communication with the data recorder apparatus which also has standby battery power to enable operation of the data collection system for a period of time after the aircraft has had a power failure or wiring failure due to fire, airframe failure, explosion, sabotage or the like.

It is an object and feature of the invention to utilize 802.11, 802.11b or a predecessor standard for data transmission between the sensor and the Multimedia Flight Data Recorder.

It is an object and feature of the invention to utilize a simple modification to the 802.11 standard for use exclusively for aircraft and airport security such that commercial 802.11 industry standard product would not interfere with data transmissions in the aircraft and airport systems.

It is an object and feature of the invention to minimize the number of electrical signals (wires) that are necessary to interconnect the to the hardened portion of the aircraft data recorder by utilization of I/P for the interconnection between the mass memory array and the rest of the system electronics for the purposes of simplifying the hermetic sealing and hardening of the mass memory array.

It is an object and feature of the invention to be a hardened file server that can be utilized to store important data that may be required to be maintained after the recorder is subjected to an intense event, such as an airplane or train crash, fire, explosion, or other environmentally severe event.

Other objects and features of the subject invention will be readily apparent from the accompanying drawings and detailed description of the preferred embodiments.

BRIEF DESCRIPTION OF THE DRAWINGS

FIG. 12 is a block diagram depicting the preferred embodiment shown in schematics of FIGS. 16A-16Z and 17A-17M.

FIG. 13 is the block diagram of the high-density flash memory array.

DETAILED DESCRIPTION OF THE PREFERRED EMBODIMENTS

Figure 1:
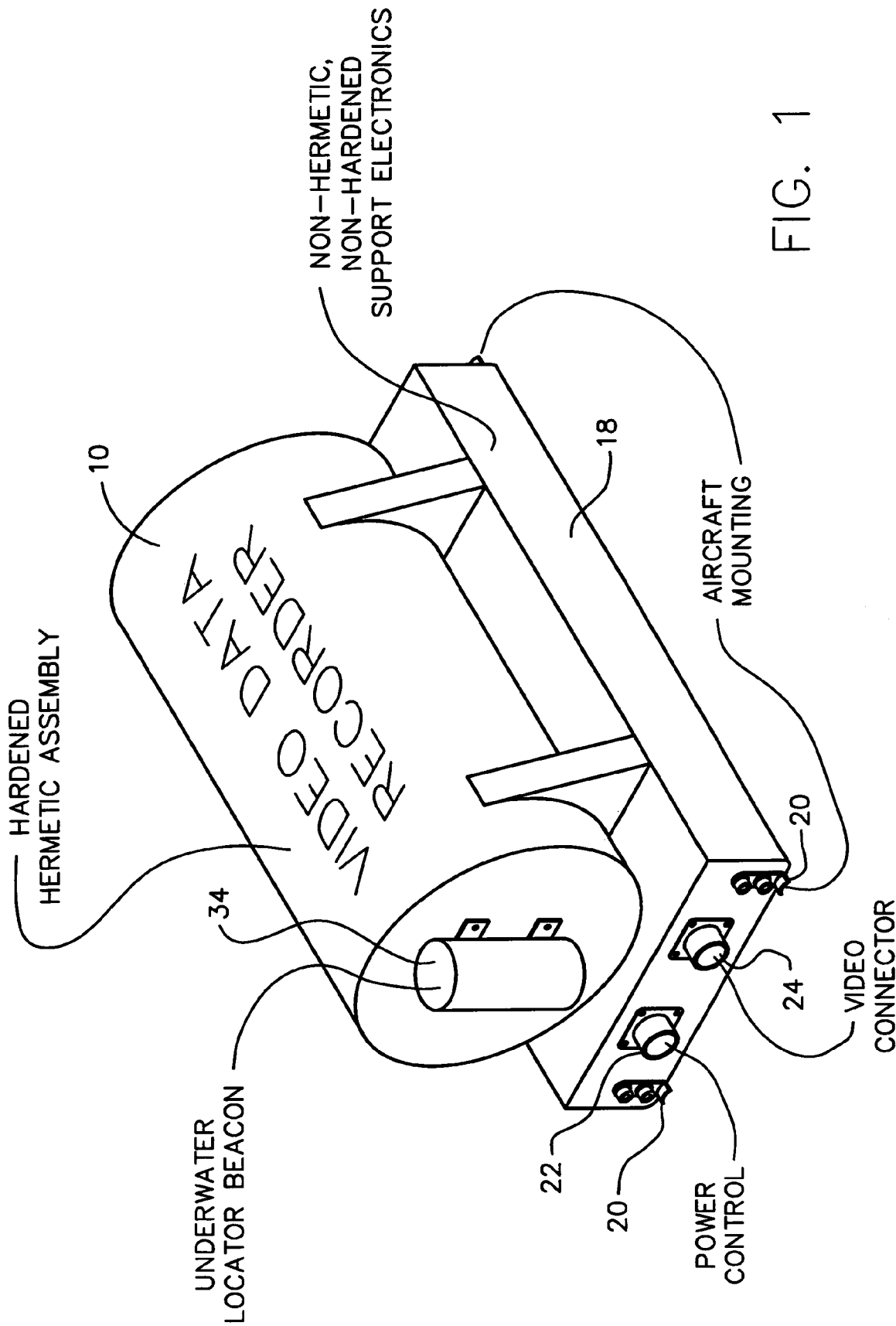
FIG. 1 is a perspective view of a digital VDR incorporating the basic features of the subject invention.
Figure 2:
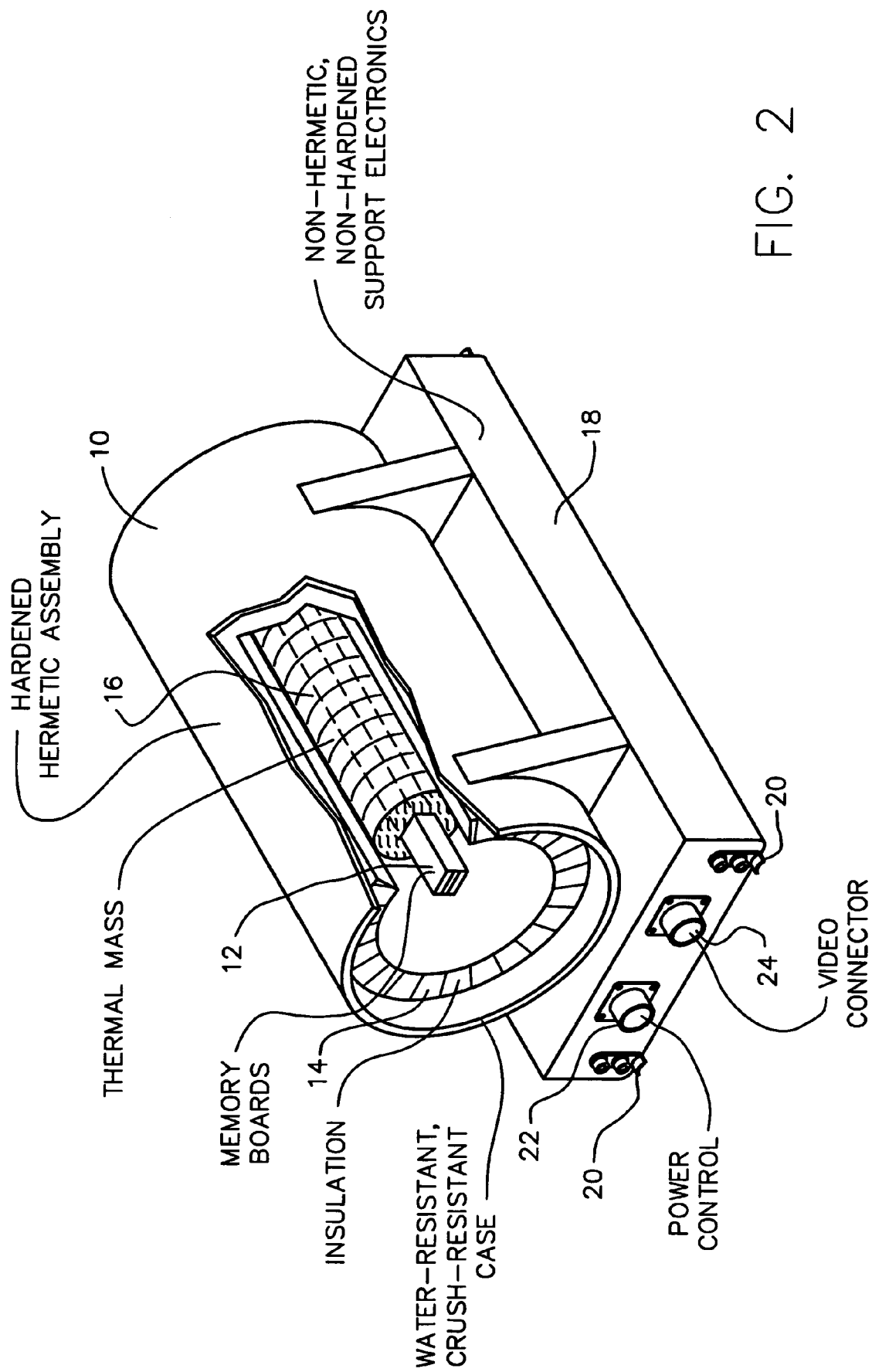
FIG. 2 is a cutaway view of the VDR of FIG. 1.

FIG. 1 is an illustration of VDR in accordance with the teachings of the subject invention and includes a hardened hermetic assembly 10 for housing the nonvolatile memory units or boards 12, see FIG. 2. In typical application, the term hardened refers to an assembly that can withstand the following conditions:

60 minutes high temperature fire exposure at 1100° C.;
10 hours low temperature fire exposure at 260° C.;
30 days of deep water immersion at a depth of 20,000 feet;
impact shock survival of 3400 Gs;
impact drop survival of 500 pounds dropped from 10 feet; and
penetration and static crush of 5000 pounds.

Standards and specifications may be found in Minimum Operational Specifications (MOPS) of TSO C-123a/C124a and Eurocae ED-56/55A.

In the subject invention, the boards are encased in an insulating envelope 14 and are sealed in a thermal mass 16. The outer wall or cover of the assembly 10 is a water-resistant, crush-resistant fire-resistant case. The support electronics are mounted in a separate support housing 18 that may be non-hardened and non-hermetic, if desired. The VDR is mounted on the airframe by suitable mounting means such as the integral tab mounts 20. The power and control coupling 22 and data or video input coupling 24 are mounted in the support housing.

Figure 3:
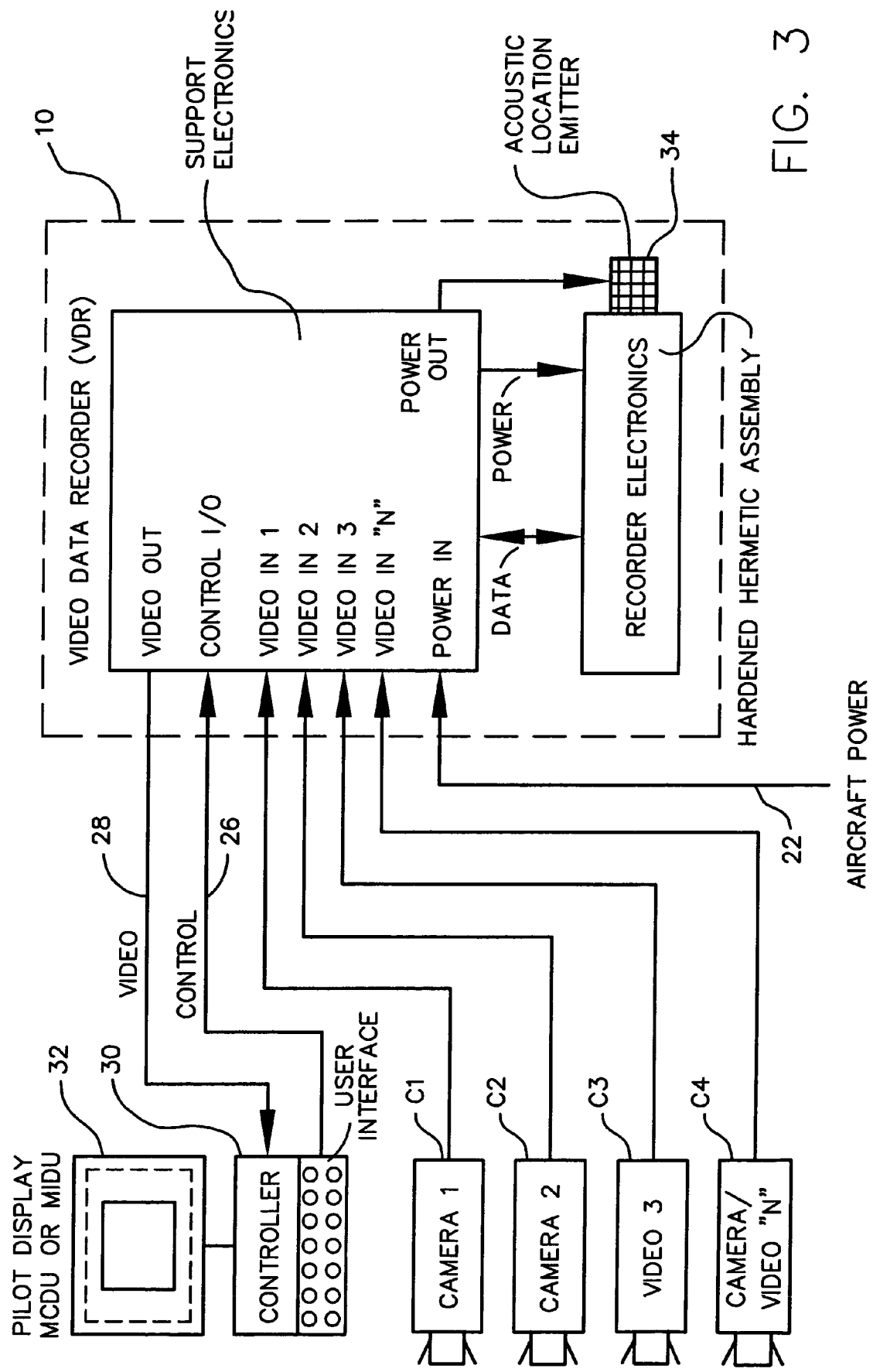
FIG. 3 is a block diagram of multiple image collection system utilizing the teachings of the subject invention.

The basic configuration of the invention is shown in FIG. 3. The VDR 10 includes a power input as previously indicated at 22, a combined multiple video/still input system for supporting a plurality of cameras C1, C2, C3, and C4, a control input/output signal line 26 and a video/still output line 28. Other video sources, such as radar video, can be connected to the video inputs instead of the cameras as show. The control and output lines are connected to the cockpit user interface controller 30 and a pilot display such as the MCDU or MIDU display 32. The controller 30 can have user interface keys for control of the system.

The memory array is contained in the hardened hermetic assembly 10. The controller supplies power and a data interchange bus to the memory array in the hardened housing. In this embodiment, an acoustic locator transmitter device 34 comprising a pattern generator is attached to the exterior of the hardened housing to provide for assistance in locating the VDR during an investigation.

Figure 4:
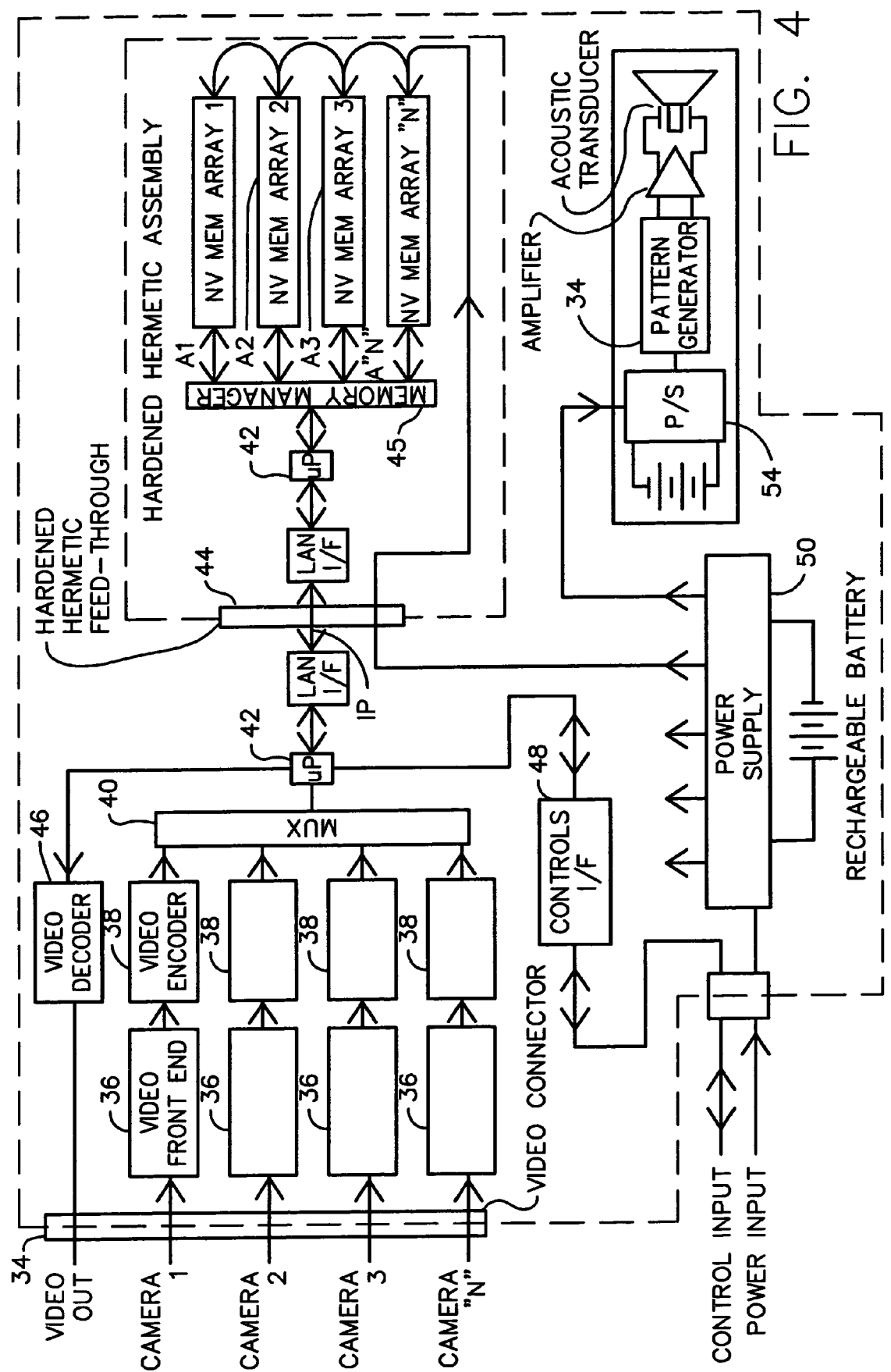
FIG. 4 is a modified system with discrete device encoders.
Figure 5:
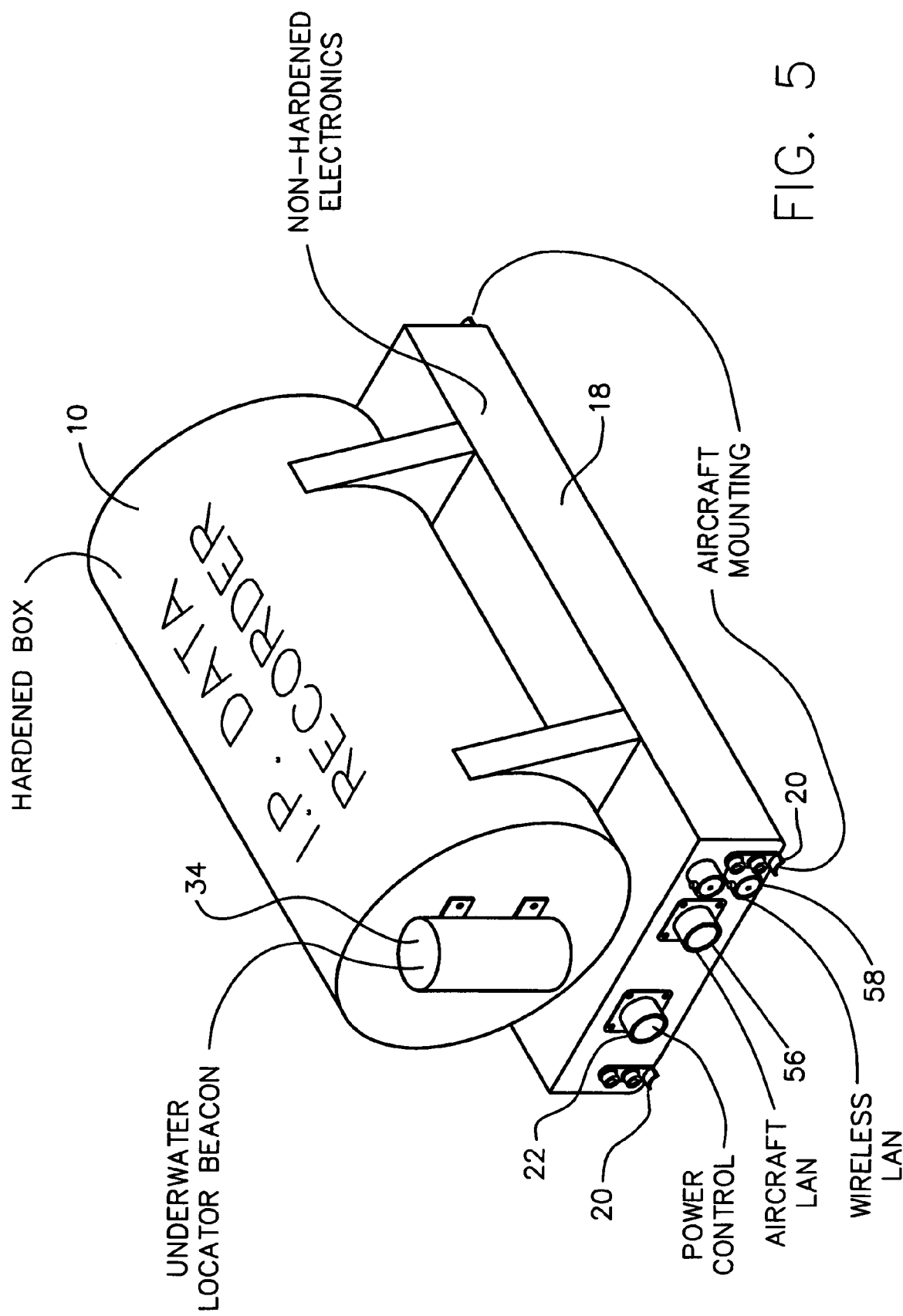
FIG. 5 is a perspective view of a modified digital multimedia flight data recorder with network connectivity.
Figure 6:
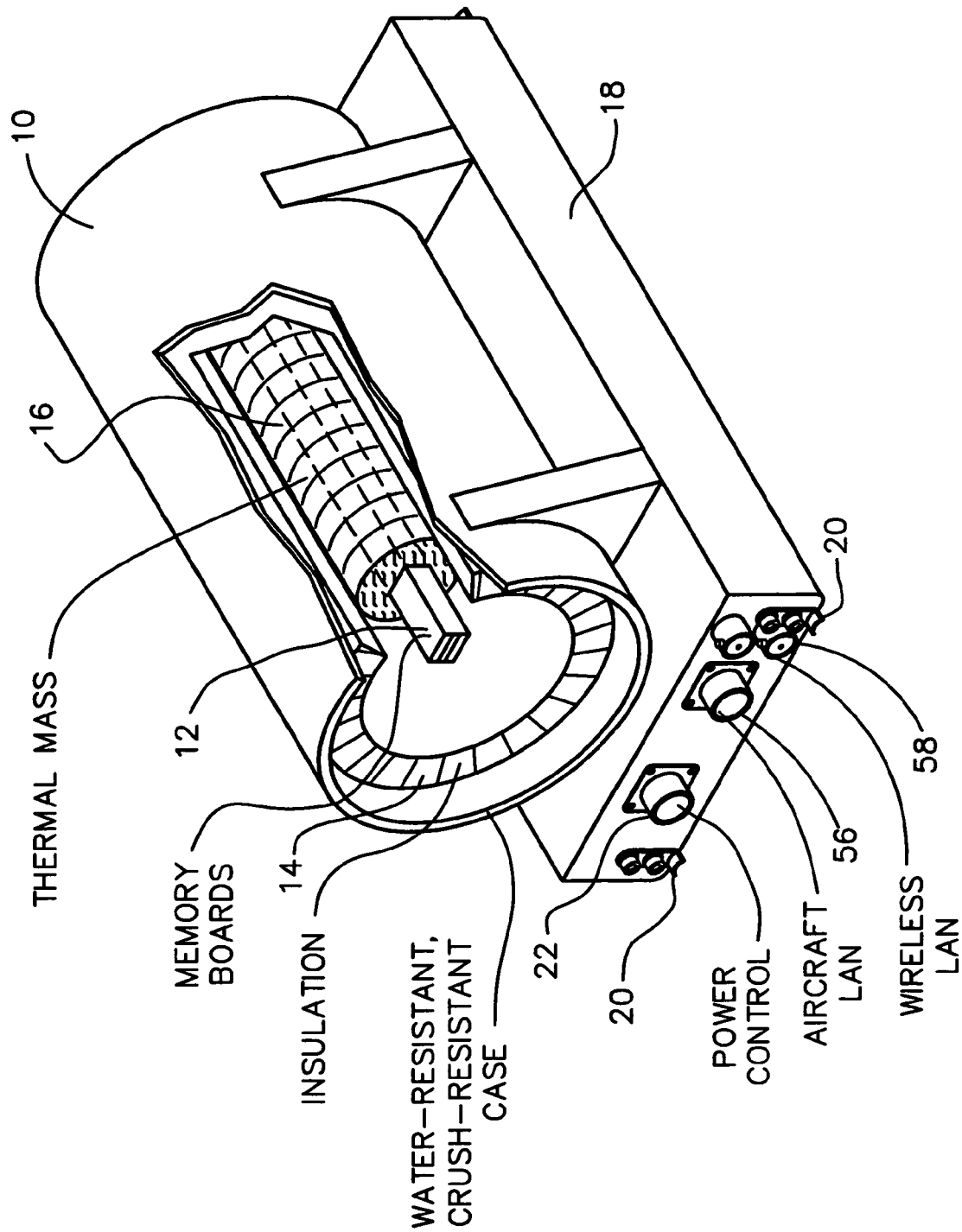
FIG. 6 is a cutaway view of the multimedia flight data recorder of FIG. 5.

An enhanced configuration of the system is shown in FIG. 4. In this configuration, each of the video devices C1, C2, C3 . . . Cn is connected to a front-end analog signal processor in the VDR for decoding and digitizing the raw data signal and entering it into the video digital encoder 38 for converting the raw data signal into a compressed video digital data stream. The plurality of encoder digital output signals are combined at a multiplexer 40 for providing a combination signal that is introduced into a processor 42 for managing and distributing the signal. The signal is sent through a suitable interface, hermetic connector 44, an additional interface to a memory manager/processor 45 for distributing the signal to the nonvolatile memory arrays A1, A2, A3 . . . AN. The signal is also entered into a video digital decoder 46 for output through the video connector 24 to facilitate display of real time data from the selected video input or archival data recalled from the hardened memory array. The control input data from the pilot or automated systems is introduced to the processor 42 through the controls interface 48. System power is provided to the power supply 50 which powers the entire system and memory array and typically will include a rechargeable battery system. The acoustic locator 34 also includes an integral backup power supply and battery 54.

In a preferred embodiment of the multimedia flight data recorder, it is an important feature of the invention that the digital data signal is in a network IP protocol and can be distributed over a wired LAN and/or wireless LAN as shown in FIGS. 5, 6, 8 and 9. In this configuration, the multimedia recorder includes a wired LAN port 56 and a wireless LAN access point such as the receiver/transmitter 58.

Figure 7:
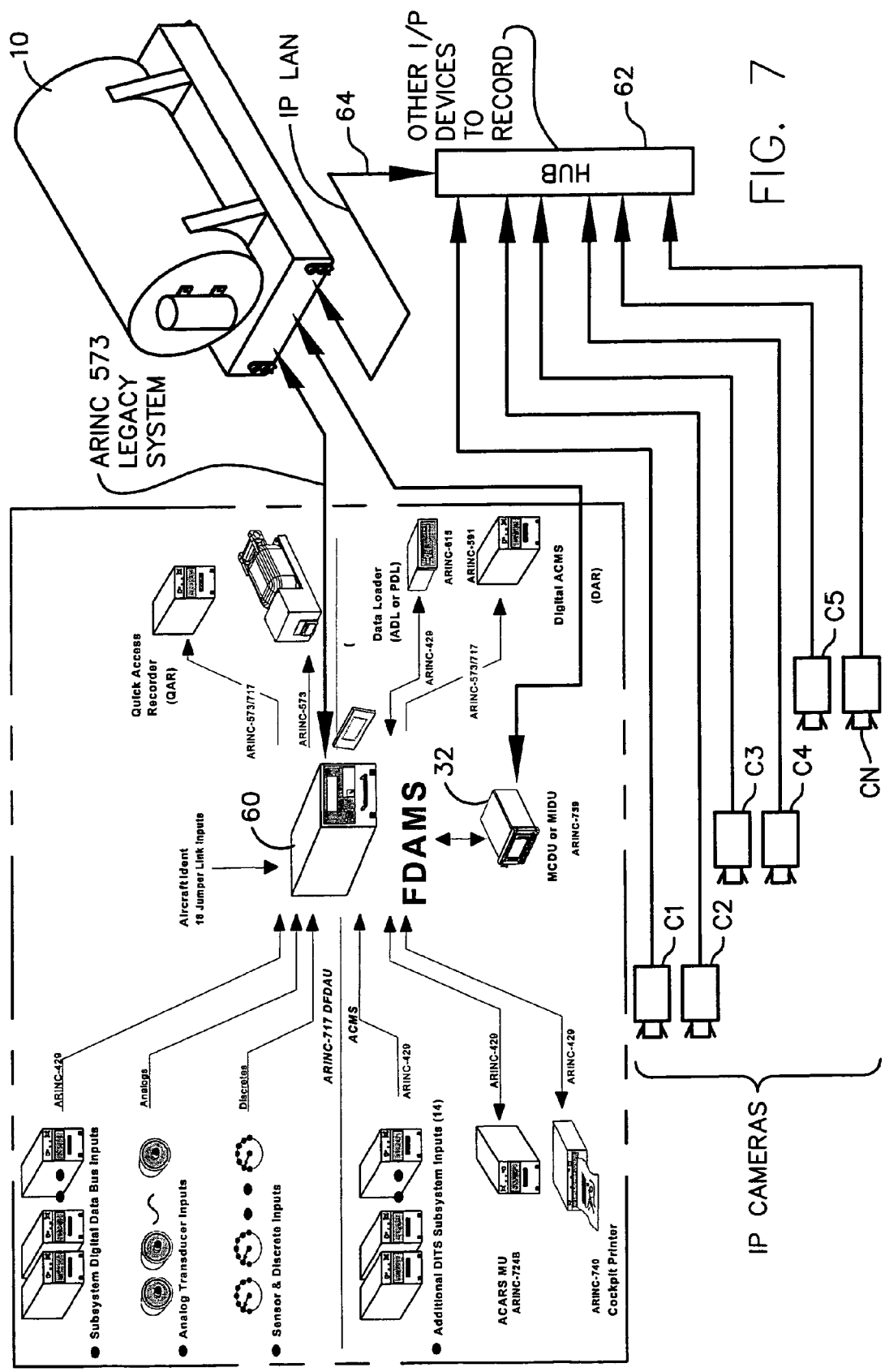
FIG. 7 is a block diagram of the system of the subject invention in combination with a legacy flight data acquisition and management system (FDAMS).

A hub 62 configuration is shown in FIG. 7 and illustrates the system of the subject invention utilizing digital encoded cameras C1-Cn. The Multimedia Flight Data Recorder can also be used in combination with a legacy flight data acquisition and management system such as (FDAMS) 60. The FDAMS system is an aircraft interface for collecting and distributing data. An example of a FDAMS system is the Honeywell Model PN 967-0212-002 or the Honeywell Model PN 967-0214-001 that is a fully integrated digital flight data acquisition unit and aircraft condition monitoring system with PC card extractable data storage. By combining this system with the data recorder of the subject invention, the data typically stored and managed in FDAMS is also transmitted to the data recorder 10 and through the data recorder management system to the pilot display MCDU or MIDU 32. Various IP sensors such as the camera C1 . . . Cn and other IP devices are connected to a central hub 62 from which a combined input signal 64 is sent over an IP LAN or IP WLAN to the data recorder 10. Control signals are also sent over the LAN connection 64.

Figure 8:
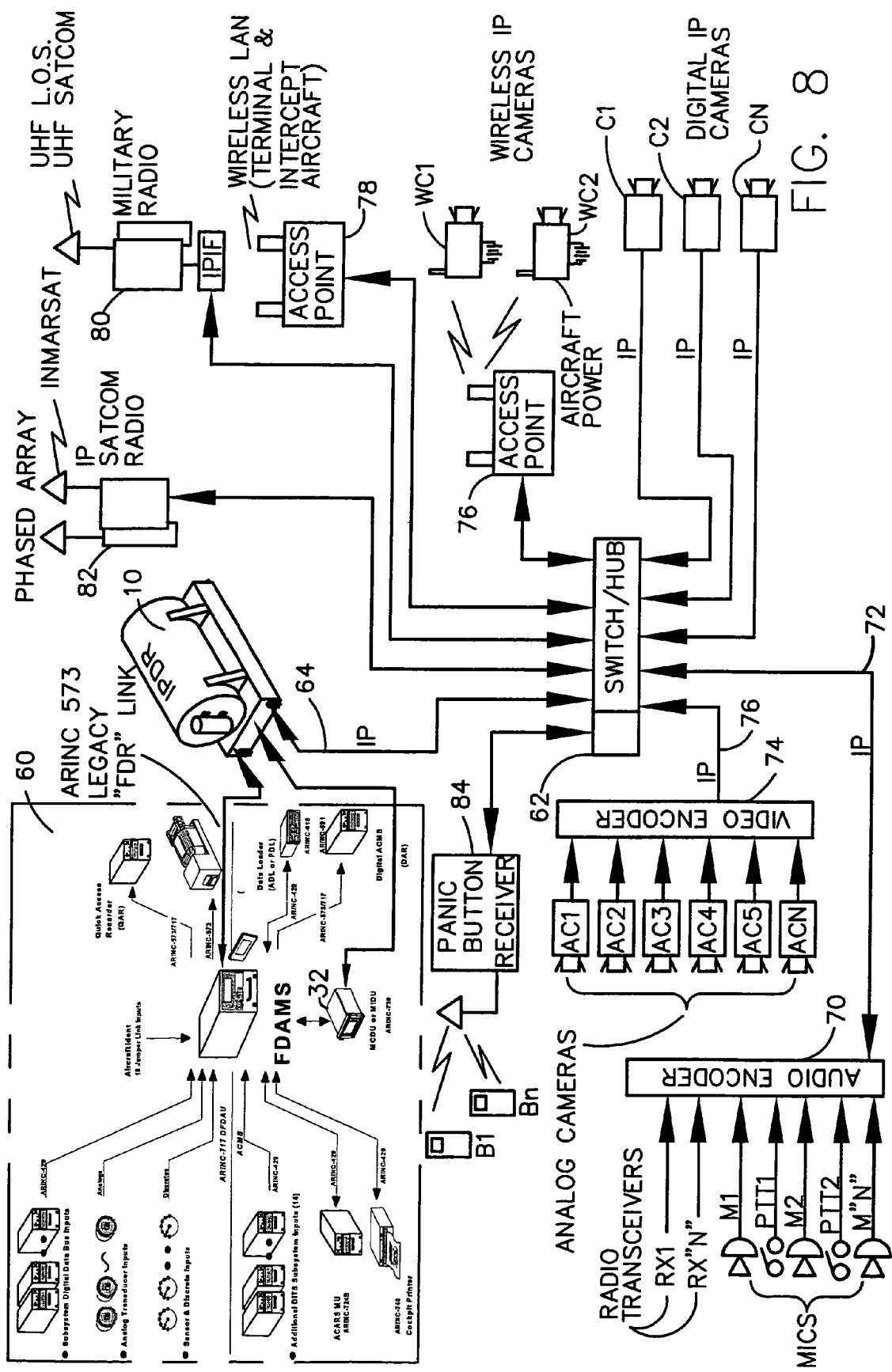
FIG. 8 is an expansion of the block diagram of FIG. 6, showing additional sensor, communications and display combinations.

A fully enhanced system is shown in FIG. 8. This incorporates the legacy FDAMS system 60, legacy analog cameras AC1 . . . ACn, various audio devices interconnected through the audio encoder 70 and the IP cameras C1 . . . Cn in a comprehensive system. The system also includes a wireless panic button system as more fully shown and described in my co-pending application Ser. No. 09/974,337, entitled: "Networked Personal Security Device", filed on Oct. 10, 2001 and incorporated herein by reference. Additional output links include SATCOM capability 82 for transmission to ground control, a military radio link 80 and a wireless LAN access point 78 for communication with the terminal and chase aircraft or other pursuit transports. Specifically, the various radio transceivers may include multiple radio channel, a speaker system and various microphone or acoustic devices, all of which feed into an audio encoder 70 to convert the discrete signals into a combined IP signal at 72. The various analog cameras AC1 . . . ACN produce raw signals introduced into a video encoder 74 for producing an IP signal at 76. The IP signals are introduced to a switch hub 62. The signals from the IP cameras C1 . . . Cn are introduced to the switch hub. IP devices may also be connected to the system via wireless LAN as well as wired LAN. The wireless devices such as wireless IP cameras WC1 and WC2 produce a wireless signal received by an access point 76 for introducing these signals to the hub 62. The hub then distributes a combined IP output signal to the wireless LAN access point 78, the military radio interface 80 and the SATCOM interface 82, as well as the data recorder 10. The panic buttons B1 . . . Bn via the wireless access point or points 84. This signal is also sent to the various receiving stations and as disclosed in by co-pending application can be both an alert signal and a control signal.

Figure 9:
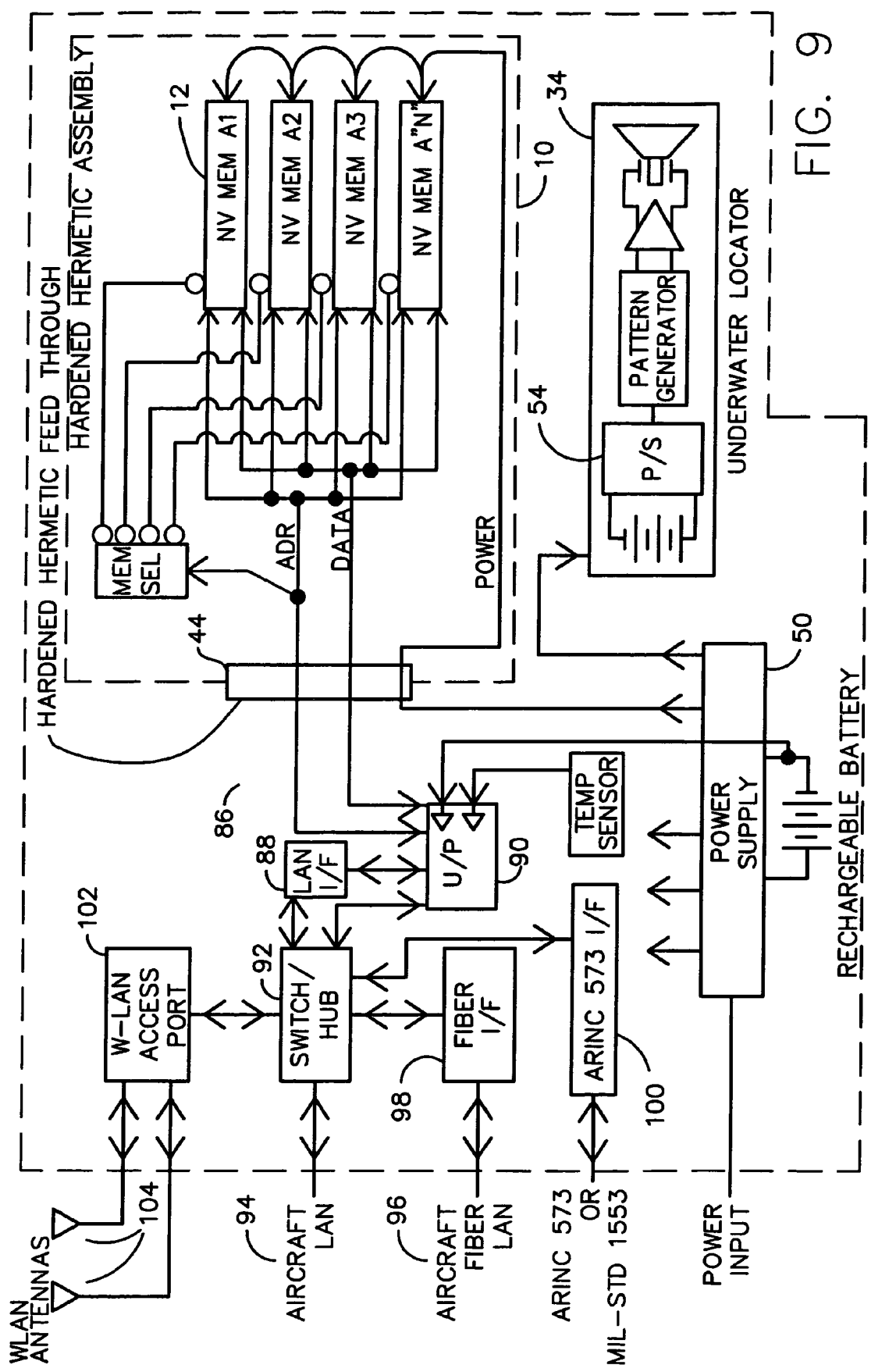
FIG. 9 is a block diagram showing LAN and wireless LAN (WLAN) capability.

FIG. 9 shows an enhancement including a LAN controller configuration. In this configuration the output signals are introduced into a memory selector 86. The memory selector distributes output to a LAN interface 88 managed by processor 90. The LAN interface is connected to a switch hub 92 for distributing the signals to the aircraft LAN 94, the aircraft fiber LAN 96 through the fiber interface 98 and an ARINC 573 or the like via the ARINC interface 100. The hub 92 also distributes the signal via a wireless LAN access point 102 to the wireless LAN via the antennas 104.

Figure 10:
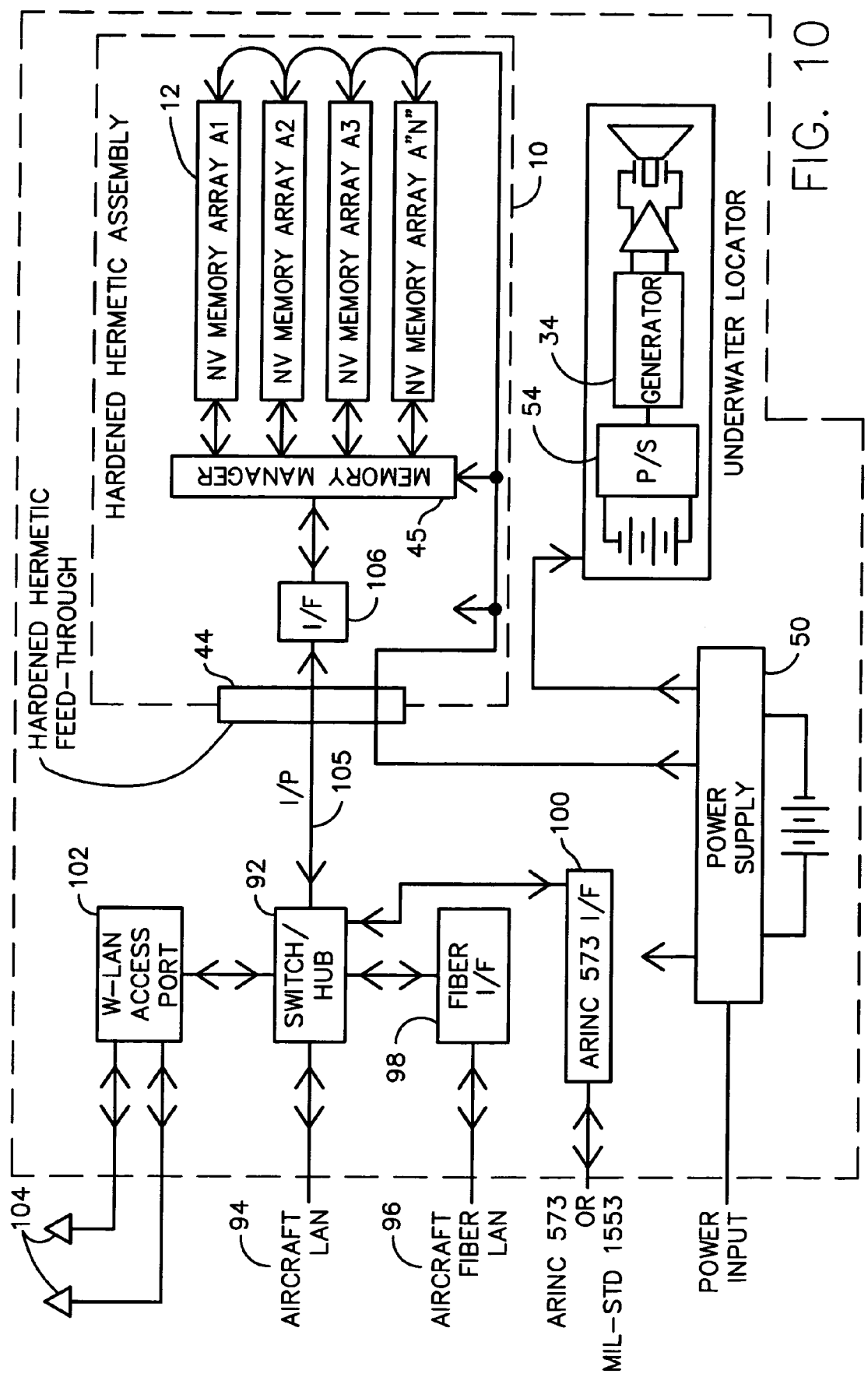
FIG. 10 is a block diagram showing direct LAN connections to the memory array in the multimedia flight data recorder.

FIG. 10 shows an enhancement with direct LAN to memory capability. This is a preferred configuration because it minimizes the number of wires that is required to enter the hardened memory array. In this configuration, the communication with the switched hub 92 is over a LAN signal line 105 and through a LAN interface 106 directly to the memory manager processor 45, fully implementing the IP protocol capability of the system.

Figure 11:
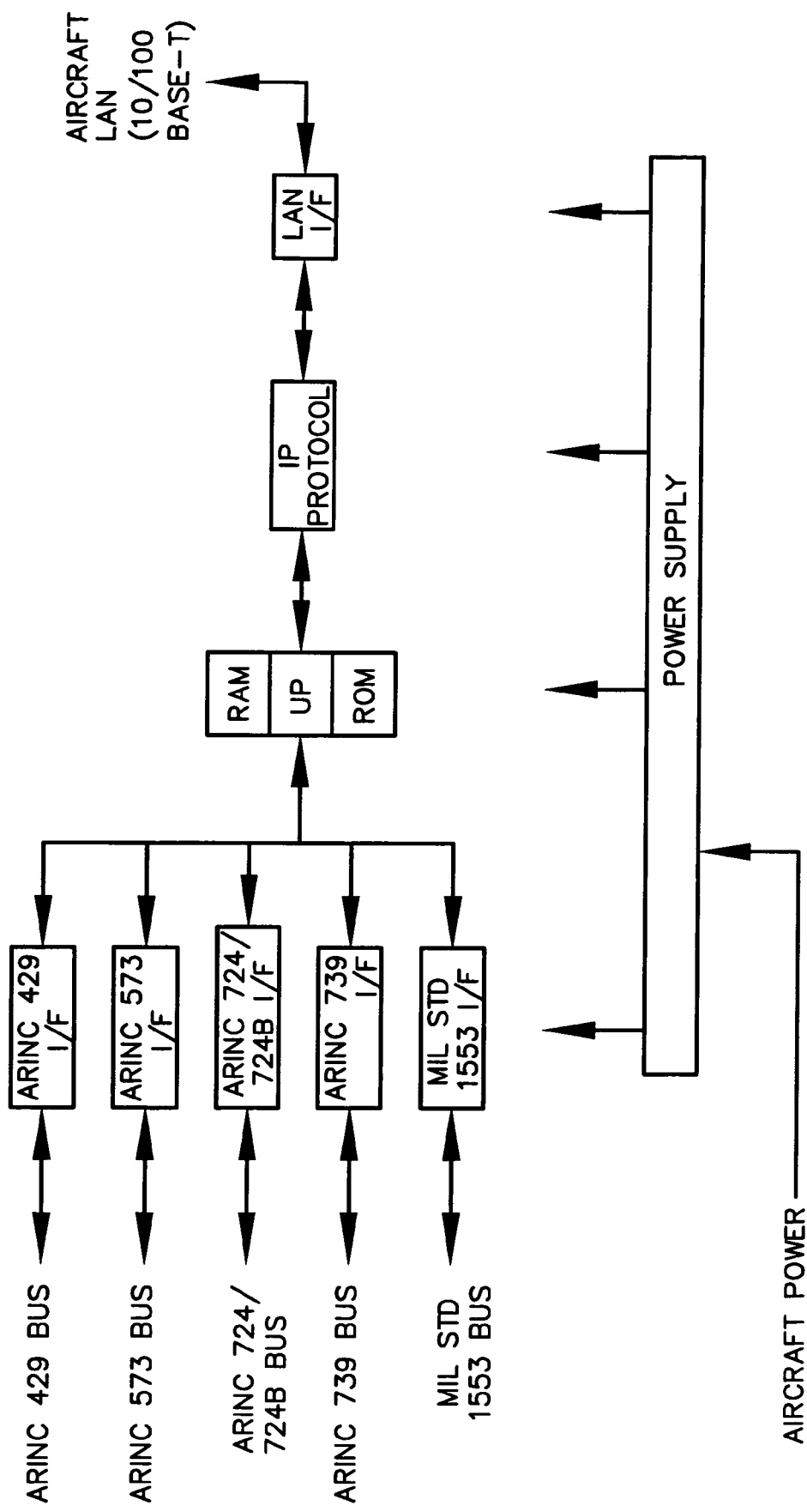
FIG. 11 is a block diagram of the protocol converter that converts AIRINC standard buses to industry standard LAN networks.

FIG. 11 shows a plurality of aircraft interface bus standards being bridged to an industry standard LAN protocol in order to communicate with the preferred embodiment of the Multimedia Flight Data Recorder or other LAN devices. Note that the protocol can be adapted to provide bridging of one or more protocols, such as Ethernet, AIRINC 429, ARINC 573, AIRINC 724/724B, ARINC 739, MIL-STD 1553B, and the like. The protocol conversion would communicate to the devices on the buses in the native protocol, strip the data and store it in the processor RAM, then transmits it out utilizing another protocol over another bus.

FIG. 12 is a preferred embodiment of the invention and is a block diagram as supported by the schematics of FIGS. 16 and 17. The circuitry is separated into main assemblies, the Support Electronics (see FIG. 16) and the Hardened Memory Array (see FIG. 17). The interface between the two is Ethernet in this preferred configuration. The Support Electronics and Hardened Memory Array can be directly tied, or can be passed through an optional switch or hub that allows interconnection to other LAN devices. There are several advantages in utilizing a standard LAN connection such as Ethernet as the interface into the Hardened Memory Array. One advantage is that there are a minimum number of wired that are required through the problematic hermetic connector into the Hardened Memory Array. Another advantage is that the Hardened Memory Array can be easily interfaced for production, setup, diagnostic and readout functions by plugging other LAN devices directly into the Hardened Memory Data Array. Of course data can be protected from unauthorized reading or tampering with system passwords and encryption.

FIG. 13 shows a high density flash card configuration such as the "CompactFlash Card data sheet from SST. The highest density card from this company is 256 megabytes on one module.

Figure 14:
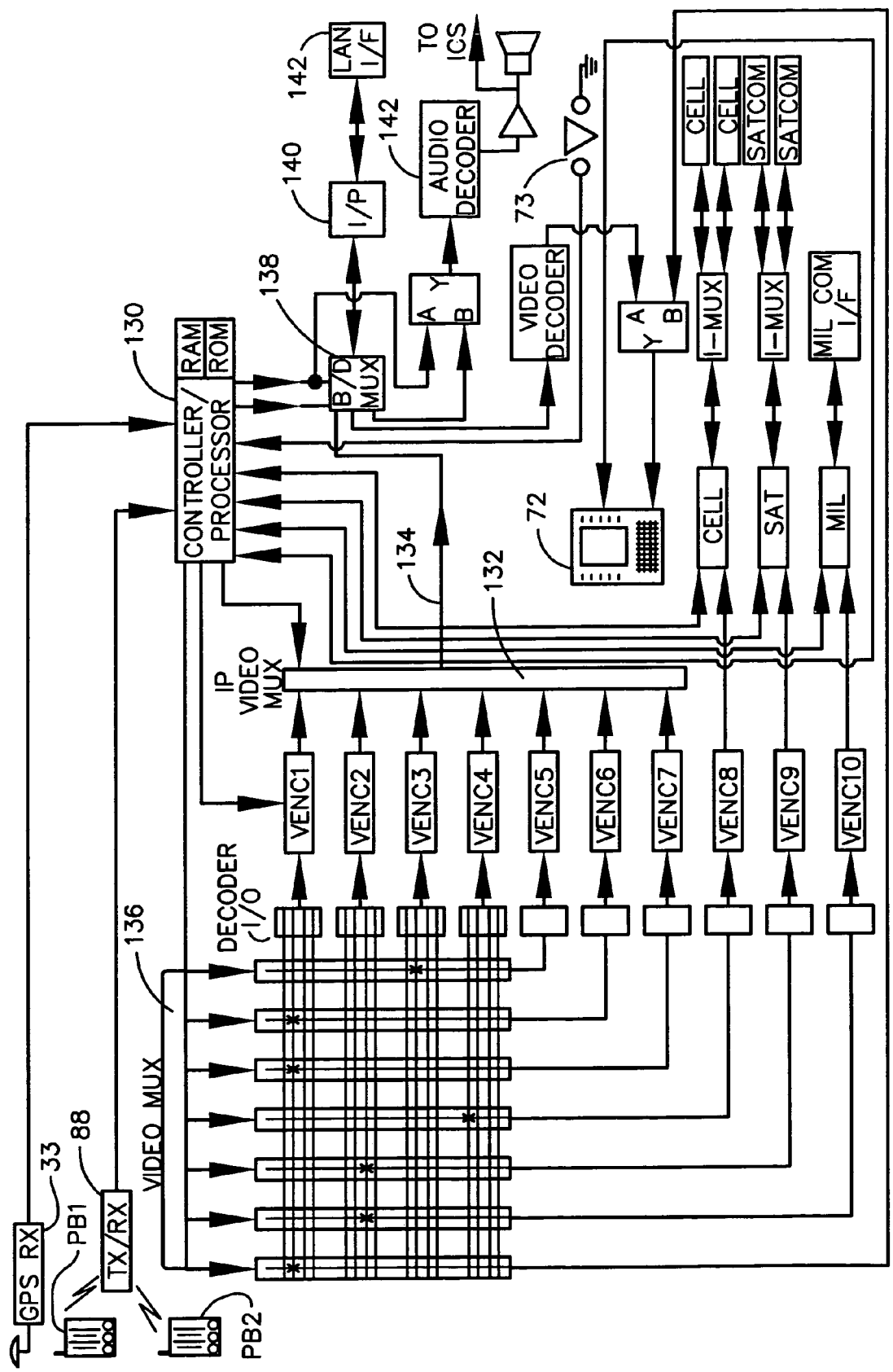
FIG. 14 is a block diagram of the "black box" circuitry of a recorder in accordance with the subject invention.
Figure 15:
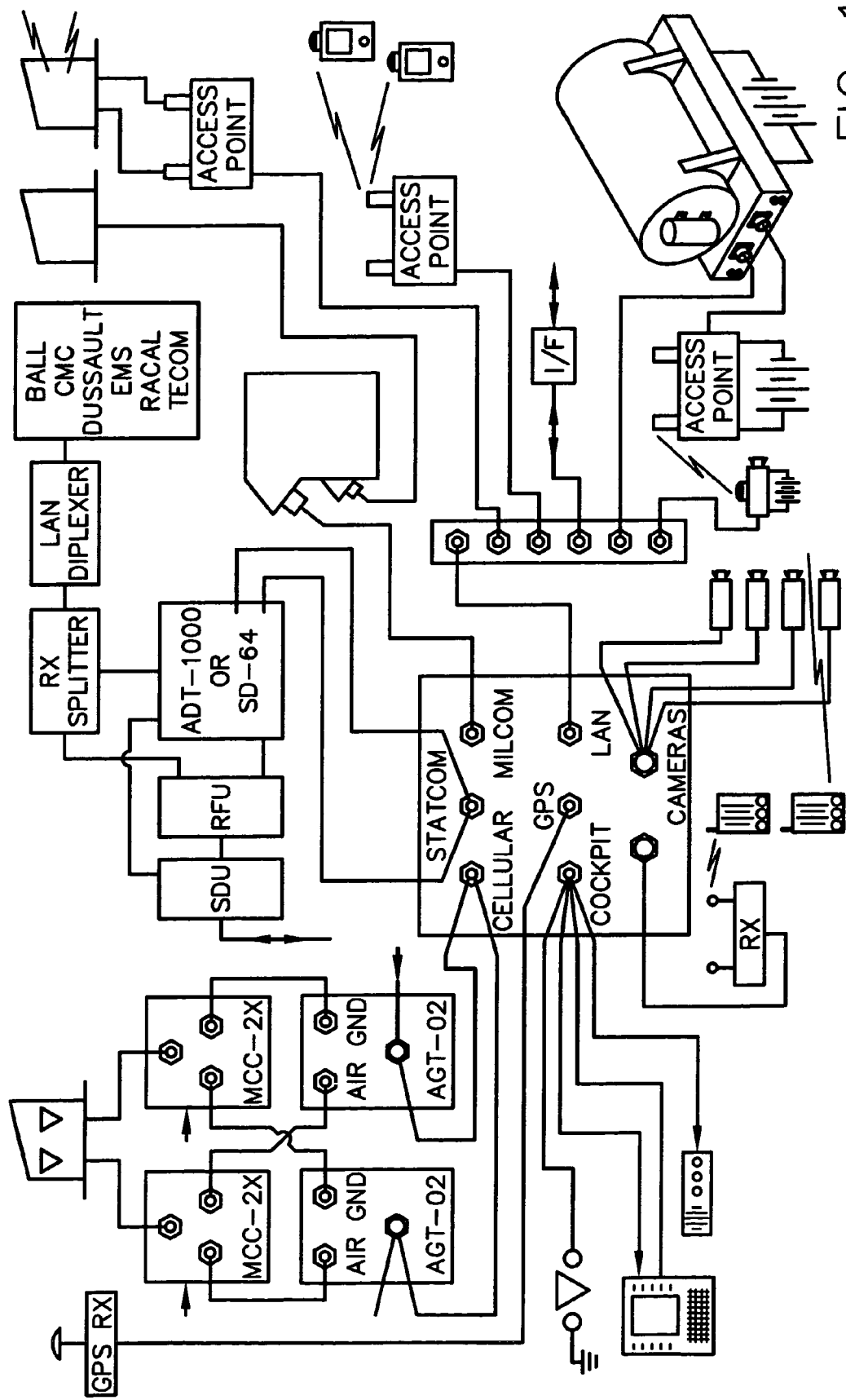
FIG. 15 is a block diagram of the connections incorporated in a typical modular system having the data recorder of the subject invention.

FIG. 14 shows the black box circuitry of the system. The GPS receiver 33, Panic Button transmitter/receivers 88, video multiplexer 136, and IP video multiplexer 132 are all in communication with the controller/processor 130. The IP video multiplexer 132 is also in communication with the multiplexer 138 (see connector cable 134) for distributing the signal via an IP interface 140 to a LAN interface 142. An Audio signal may also be distributed, see audio decoder 143. Connectivity to a control panel 72 is also shown. A typical modular commercial system is shown in FIG. 15.

Figure 16A:
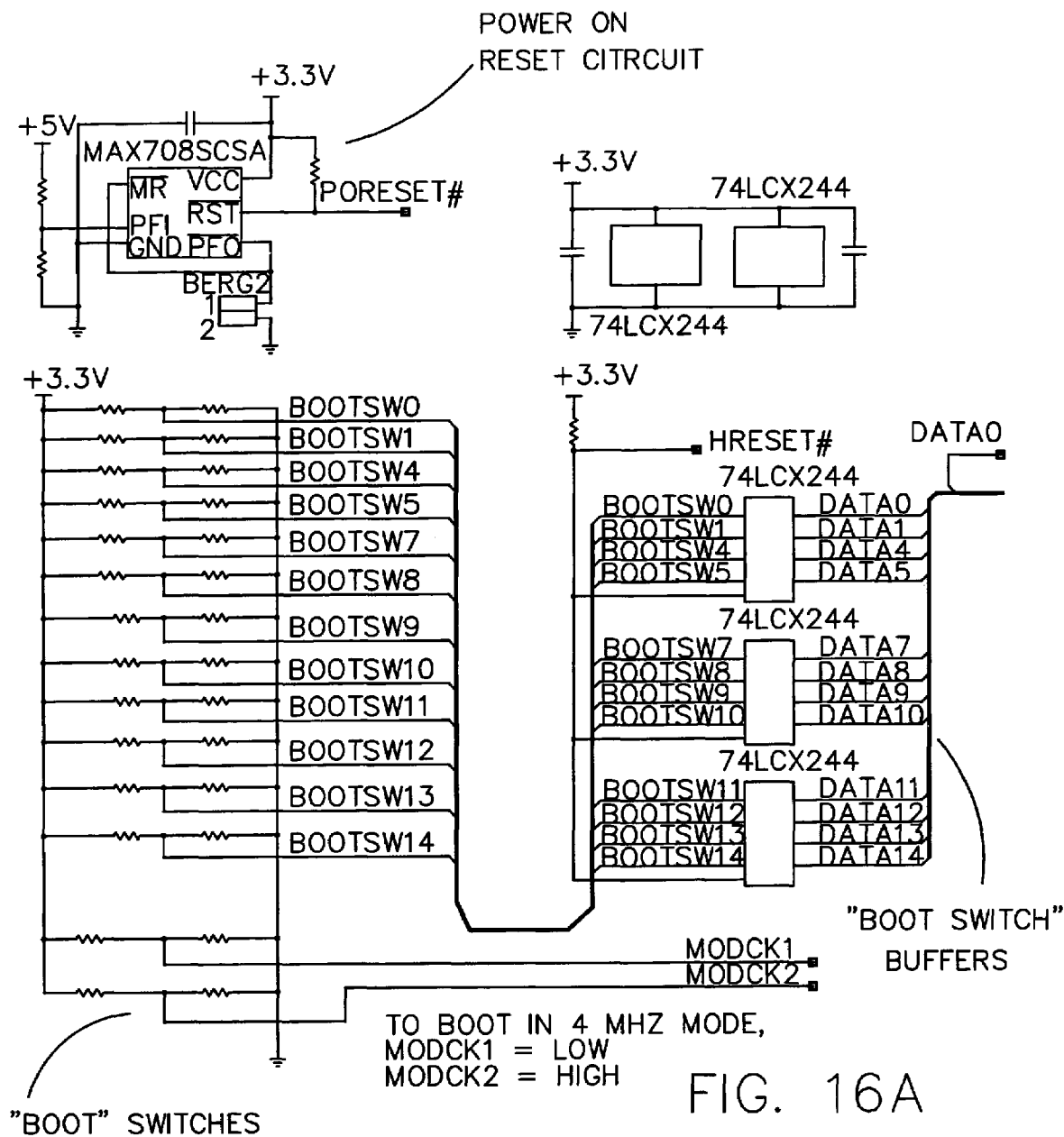
FIGS. 16A to 16Z are the schematic of the support electronics module of the preferred embodiment as shown in FIG. 12.
Figure 16B:
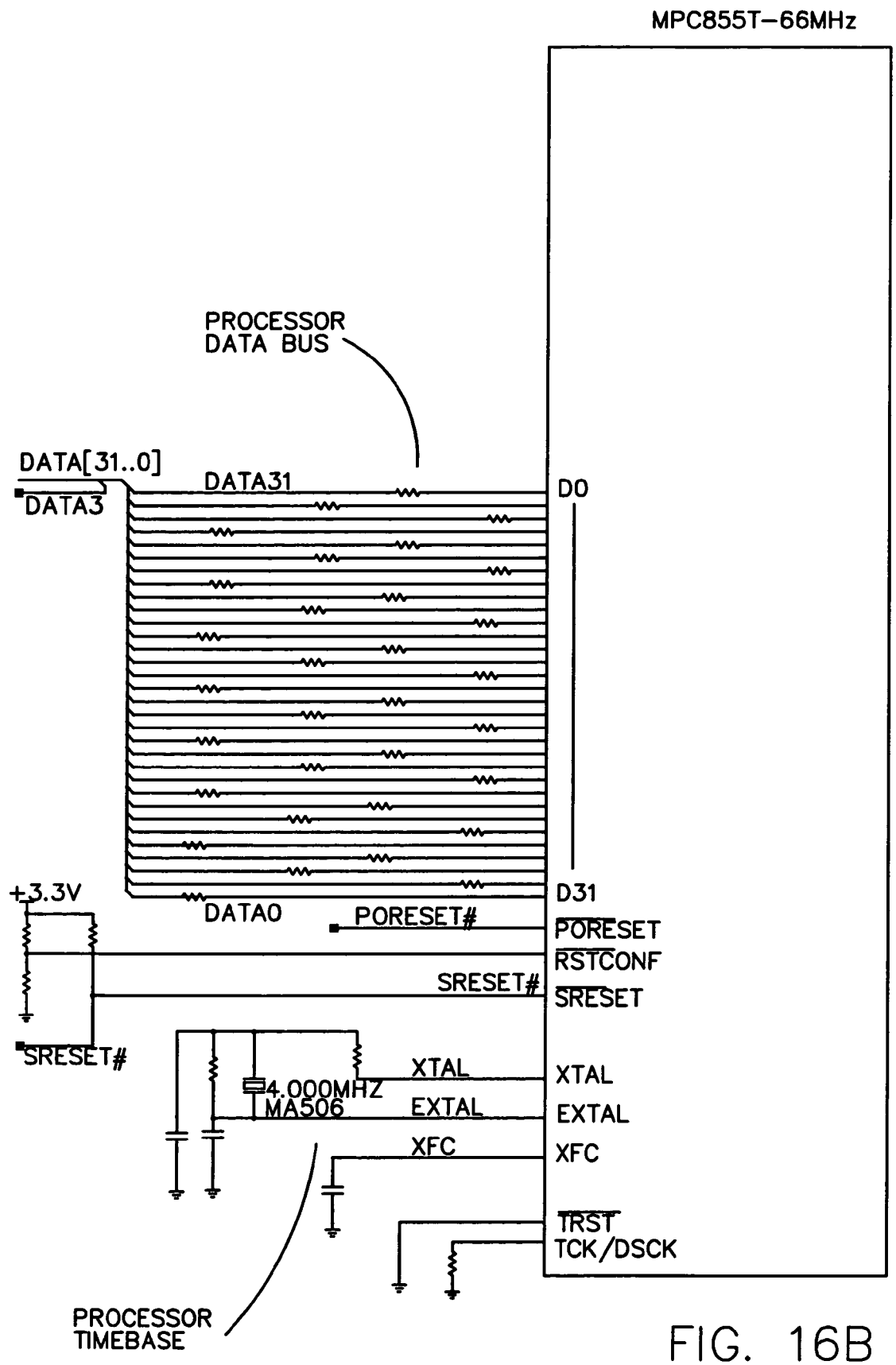
Figure 16C:
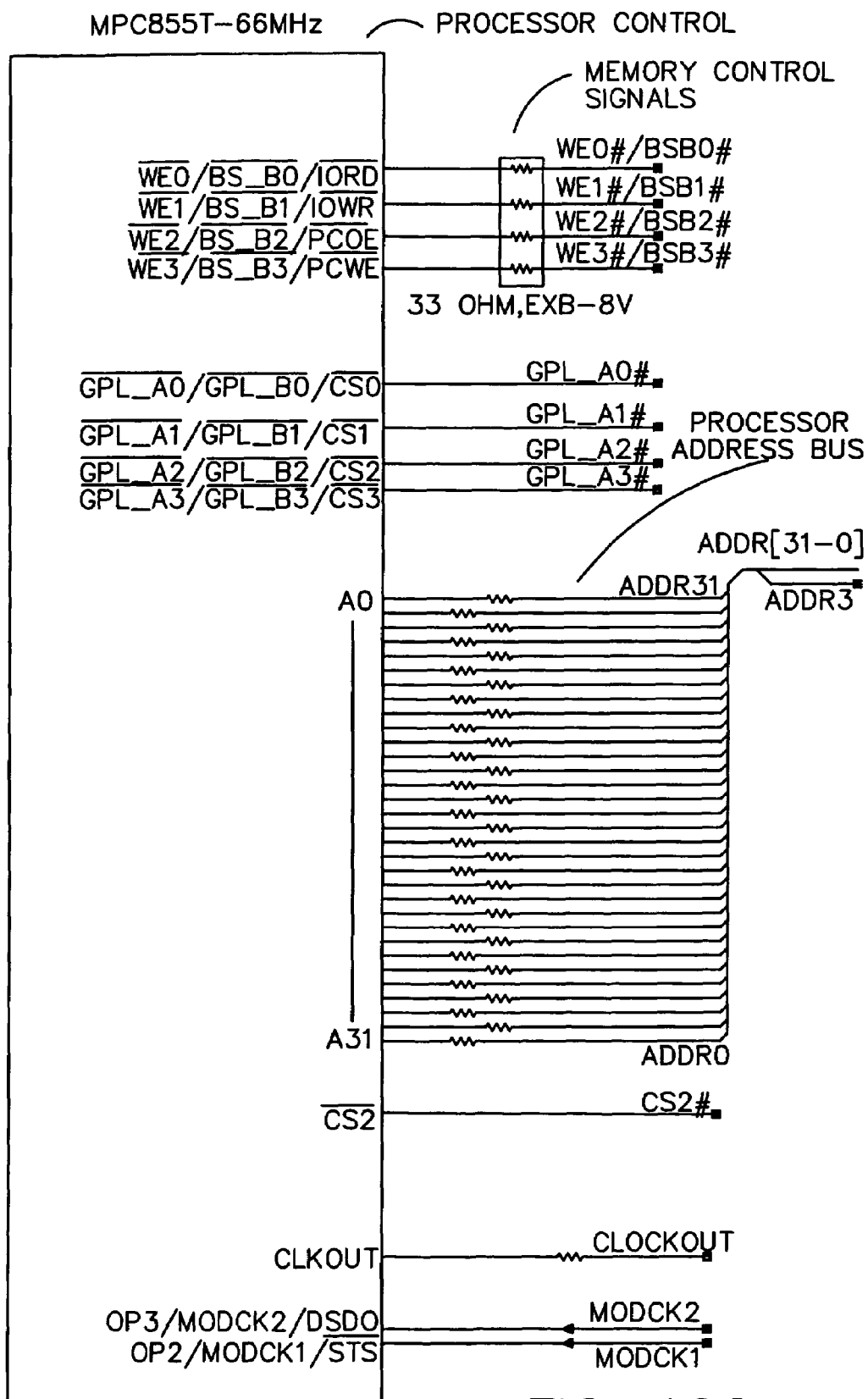
Figure 16D:
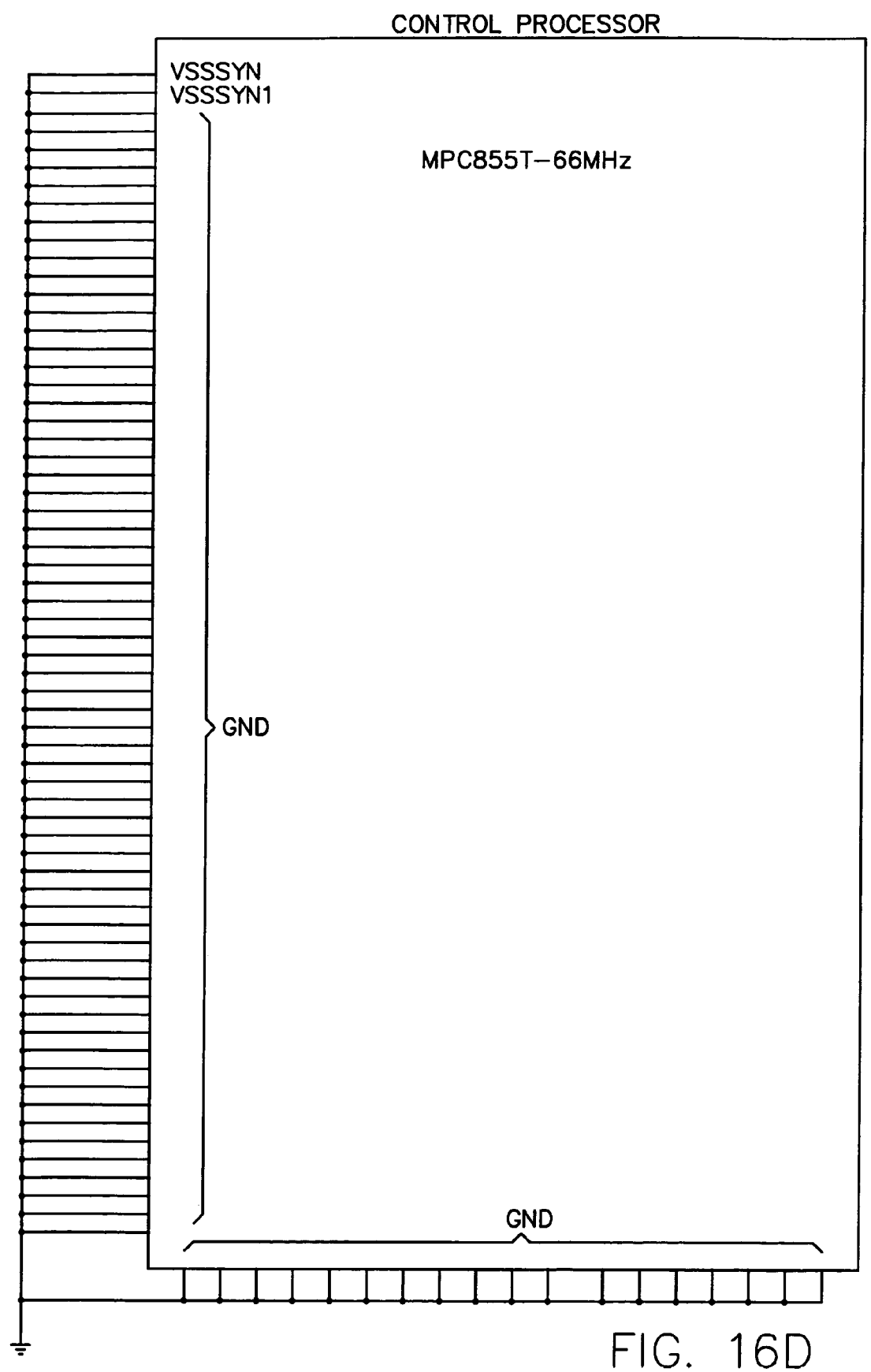
Figure 16E:
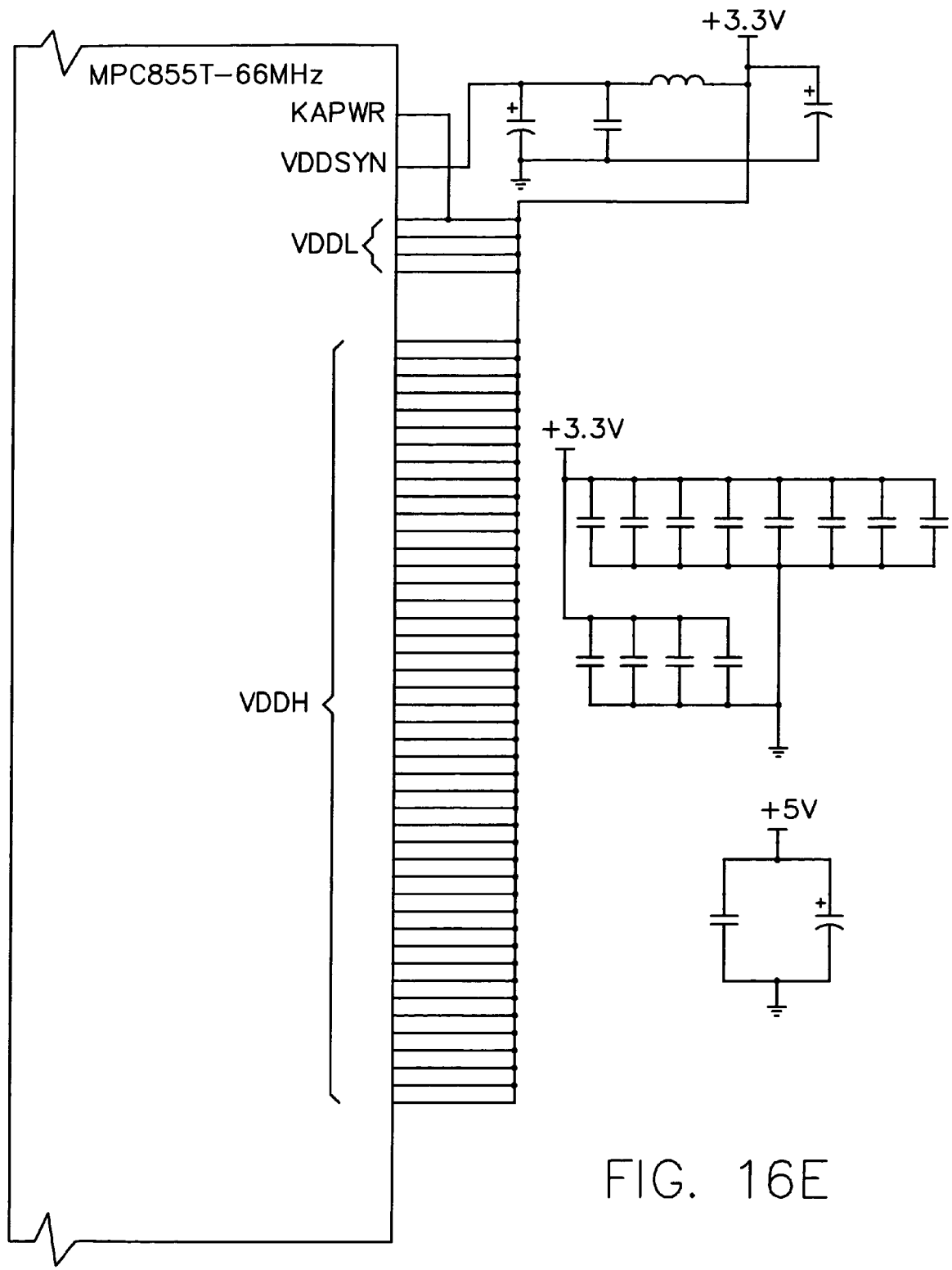
Figure 16F:
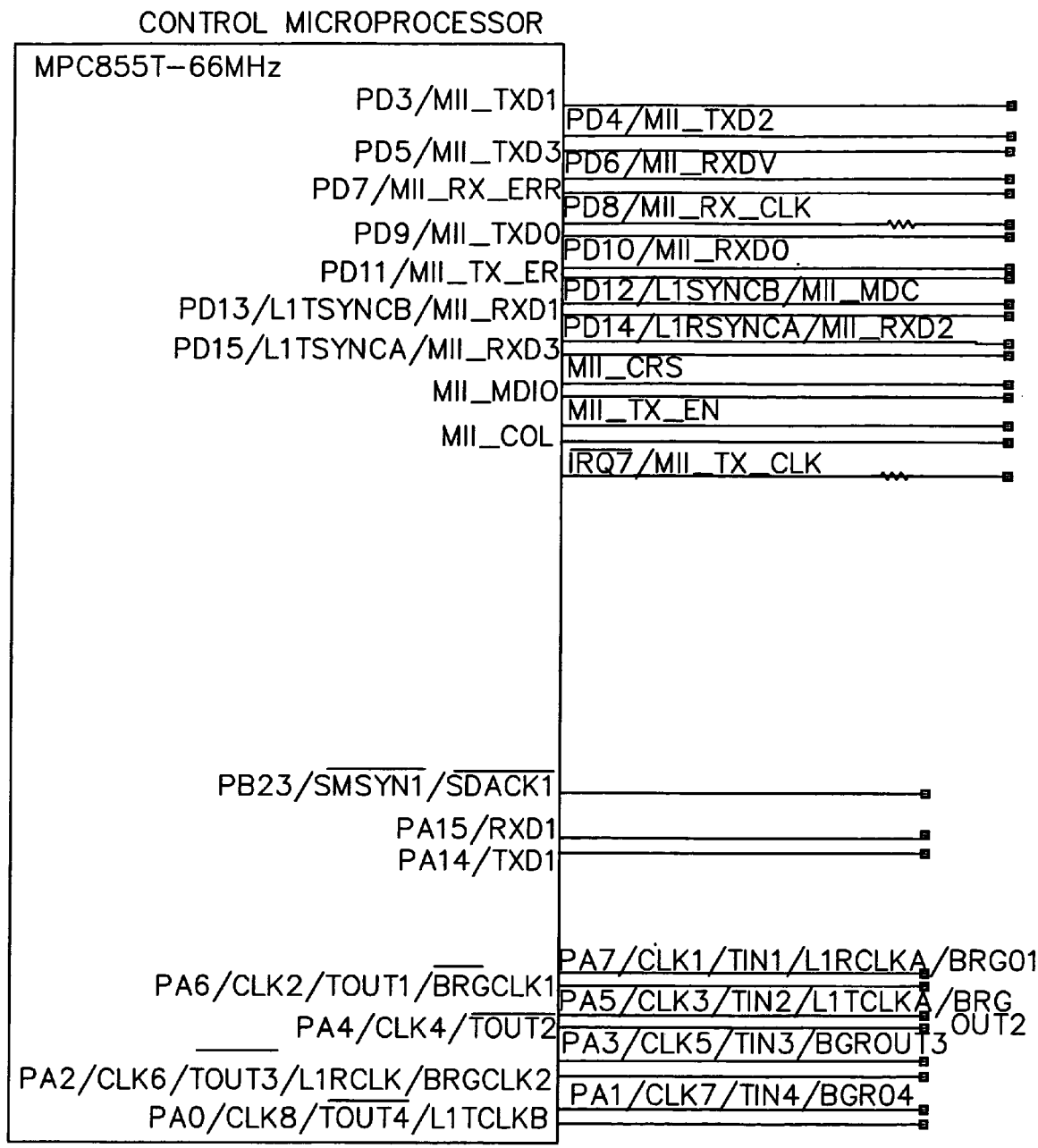
Figure 16G:
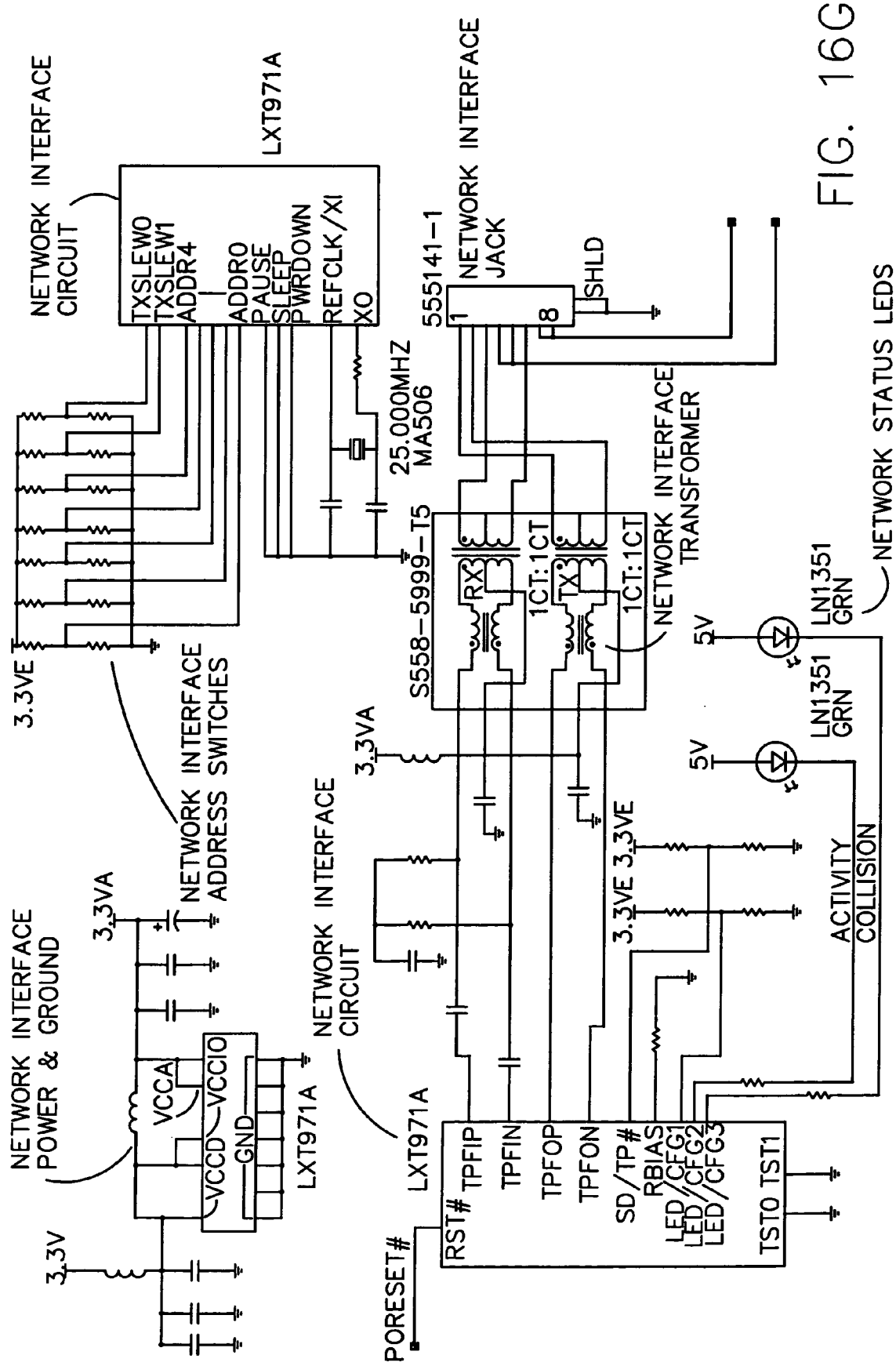
Figure 16H:
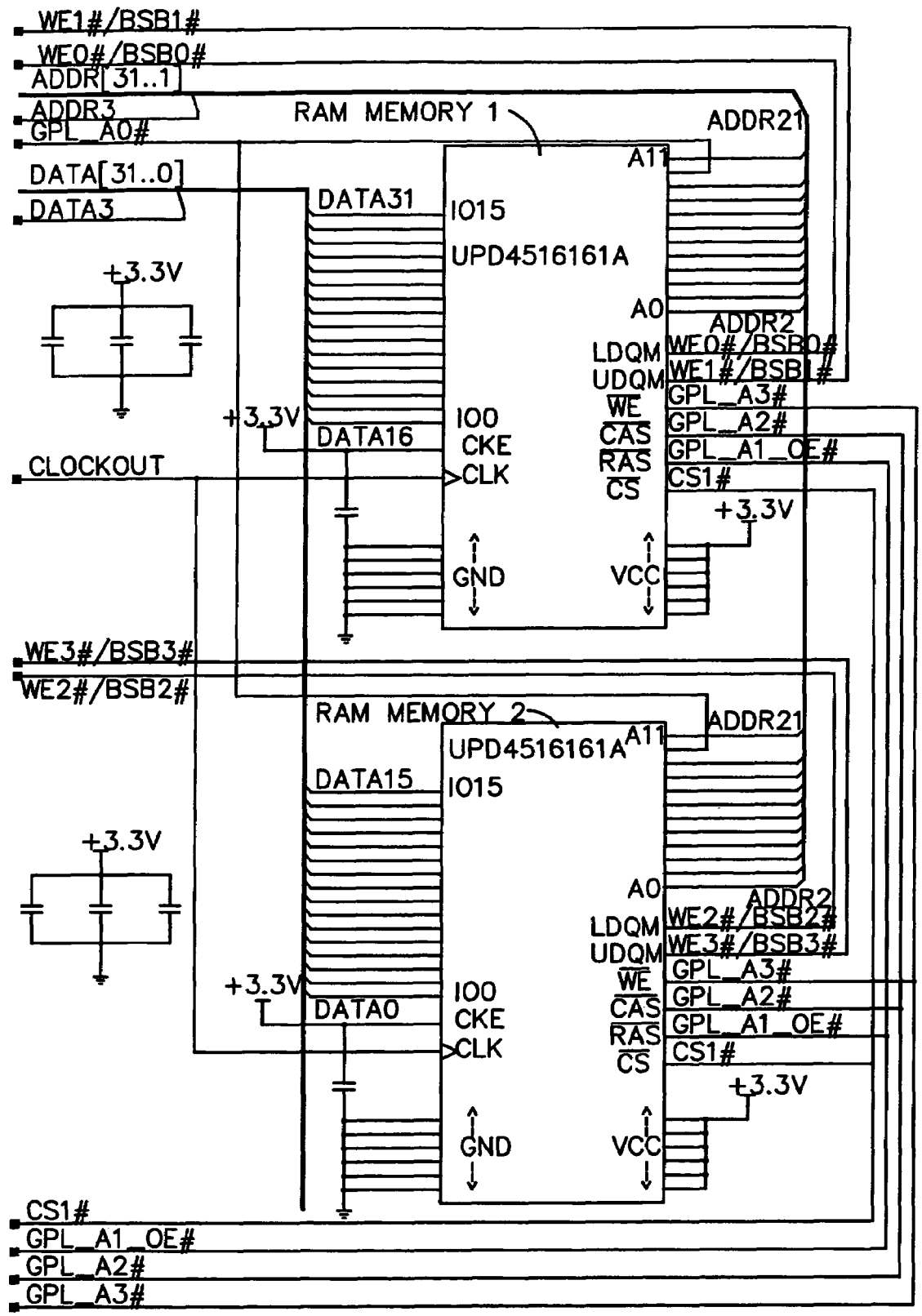
Figure 16I:
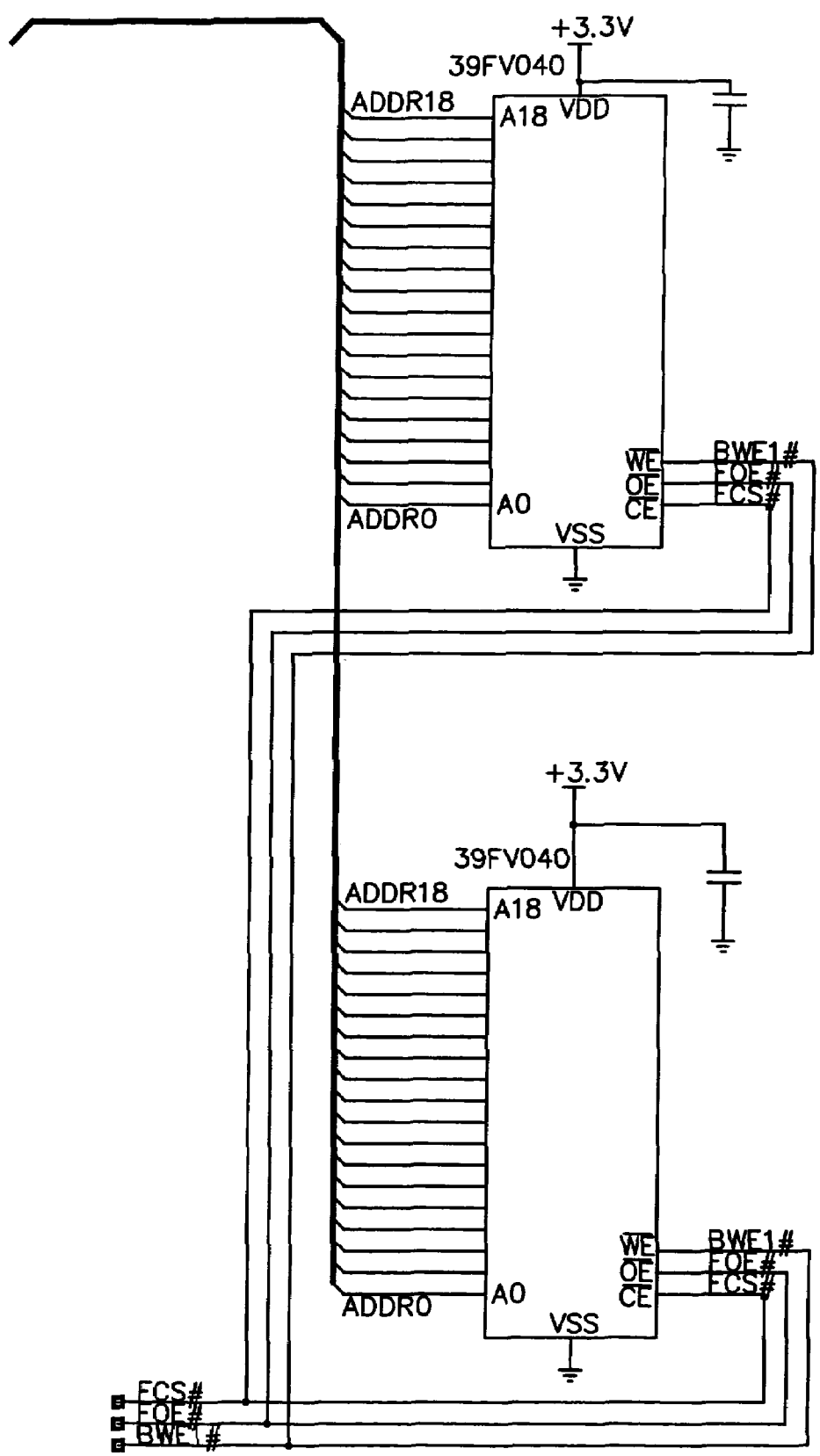
Figure 16J:
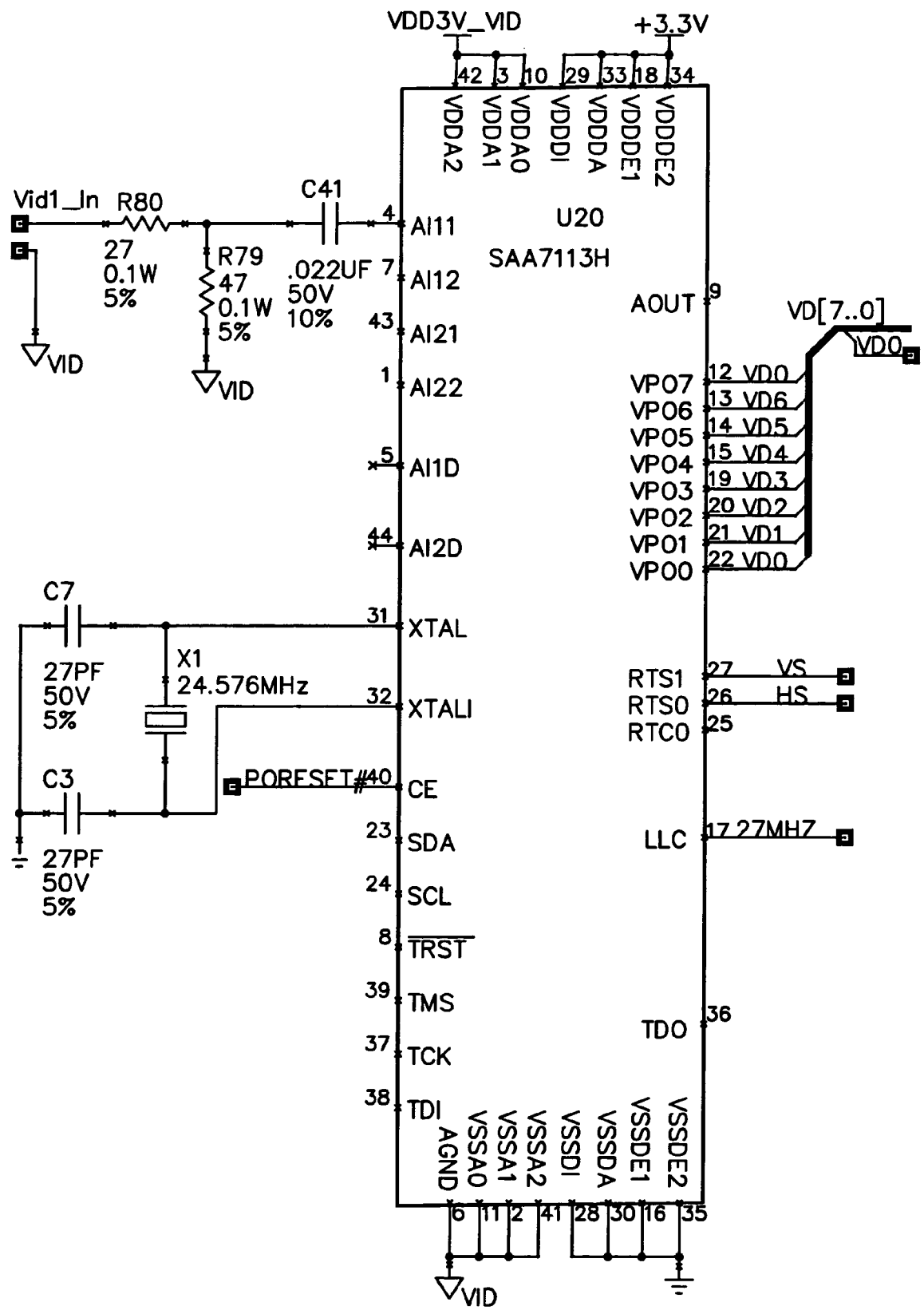
Figure 16K:
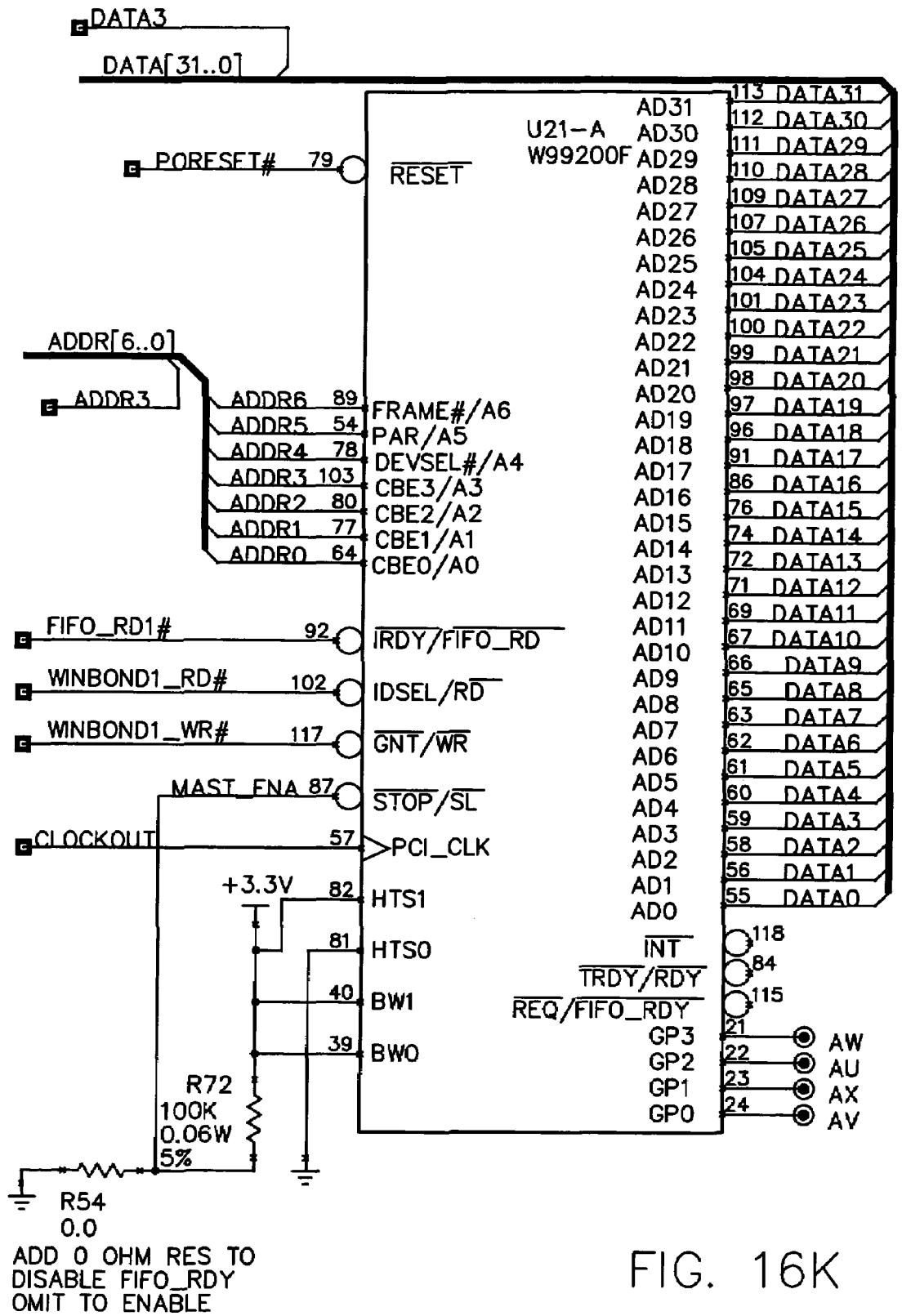
Figure 16L:
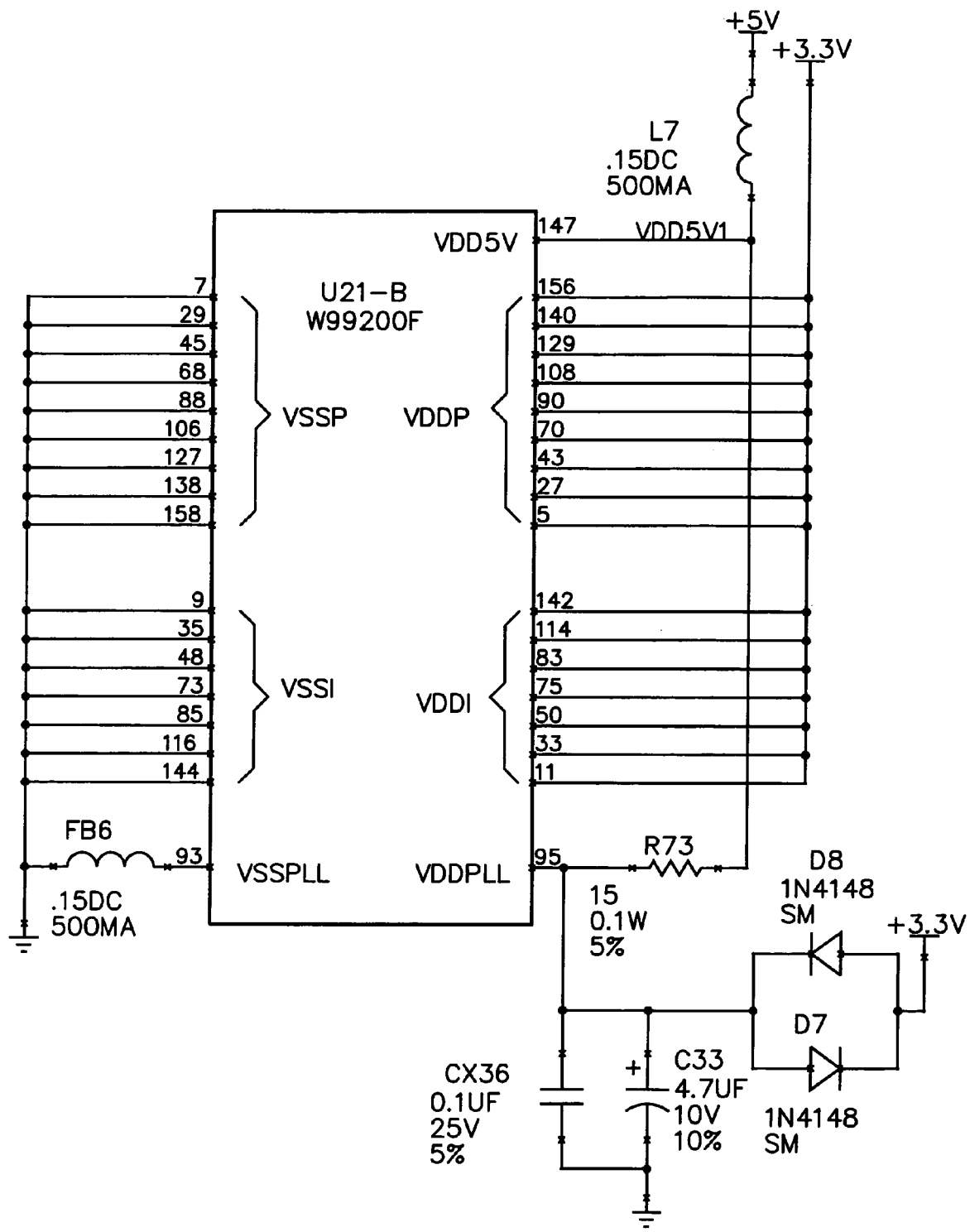
Figure 16M:
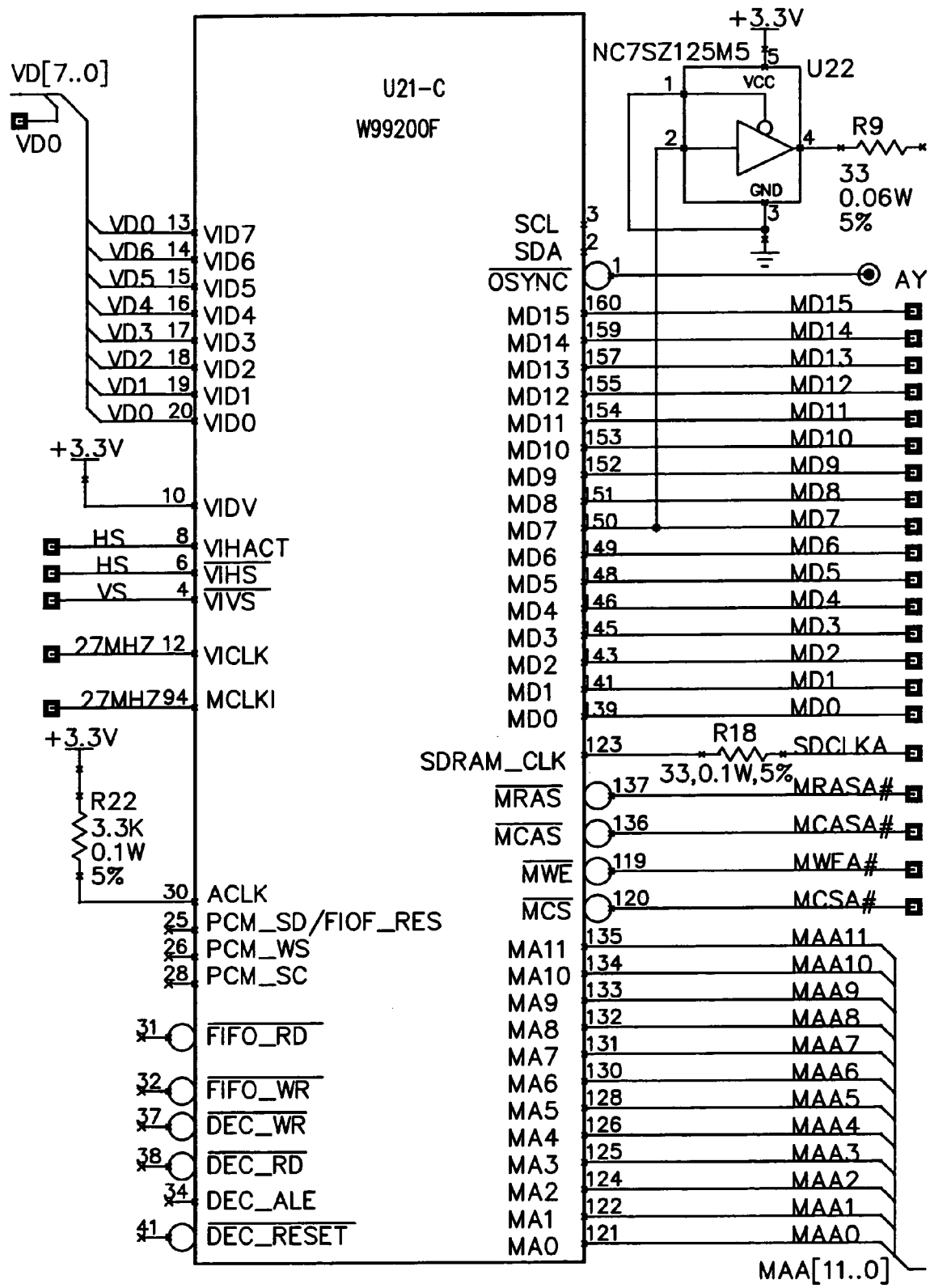
Figure 16N:
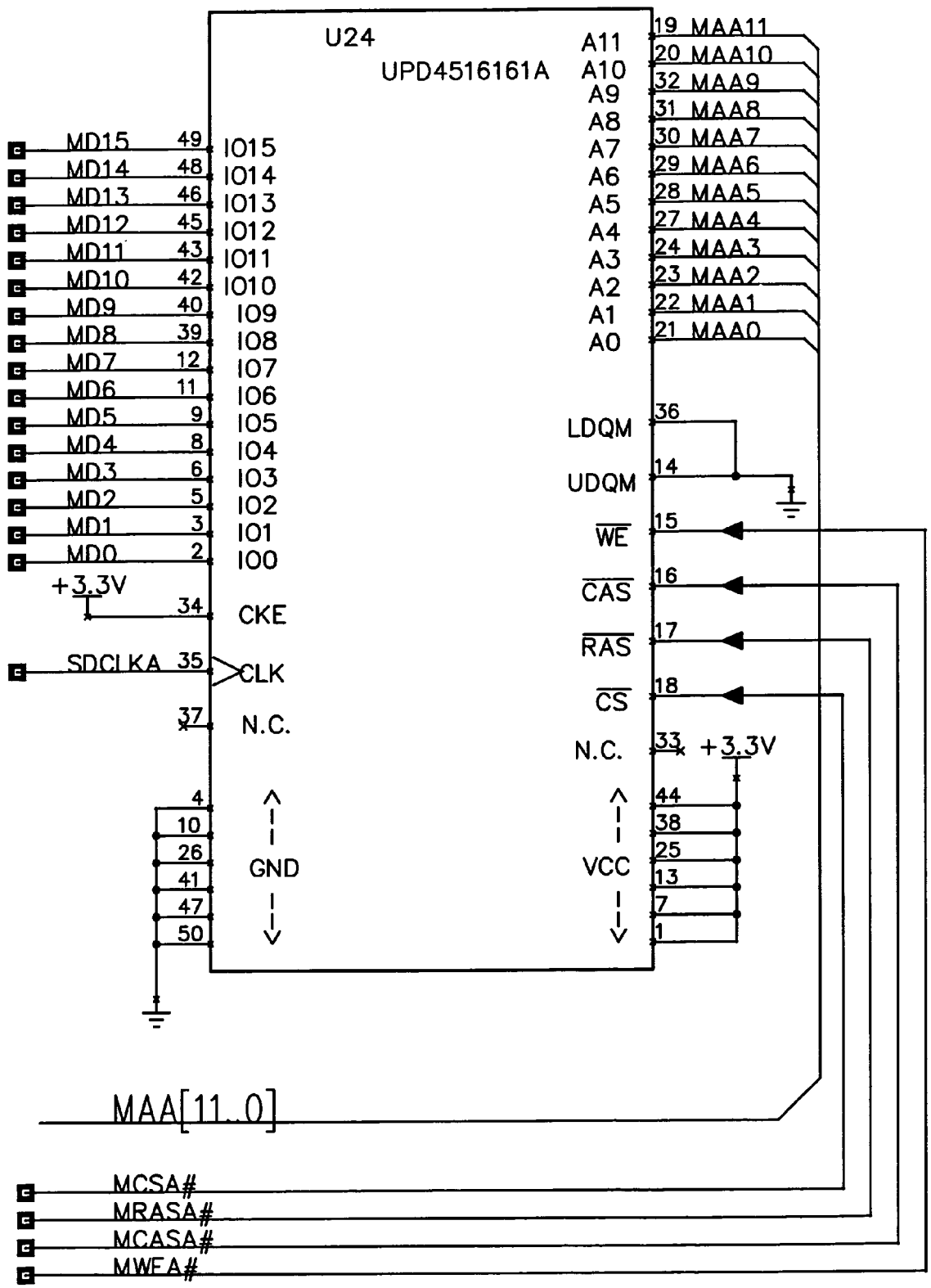
Figure 16P:
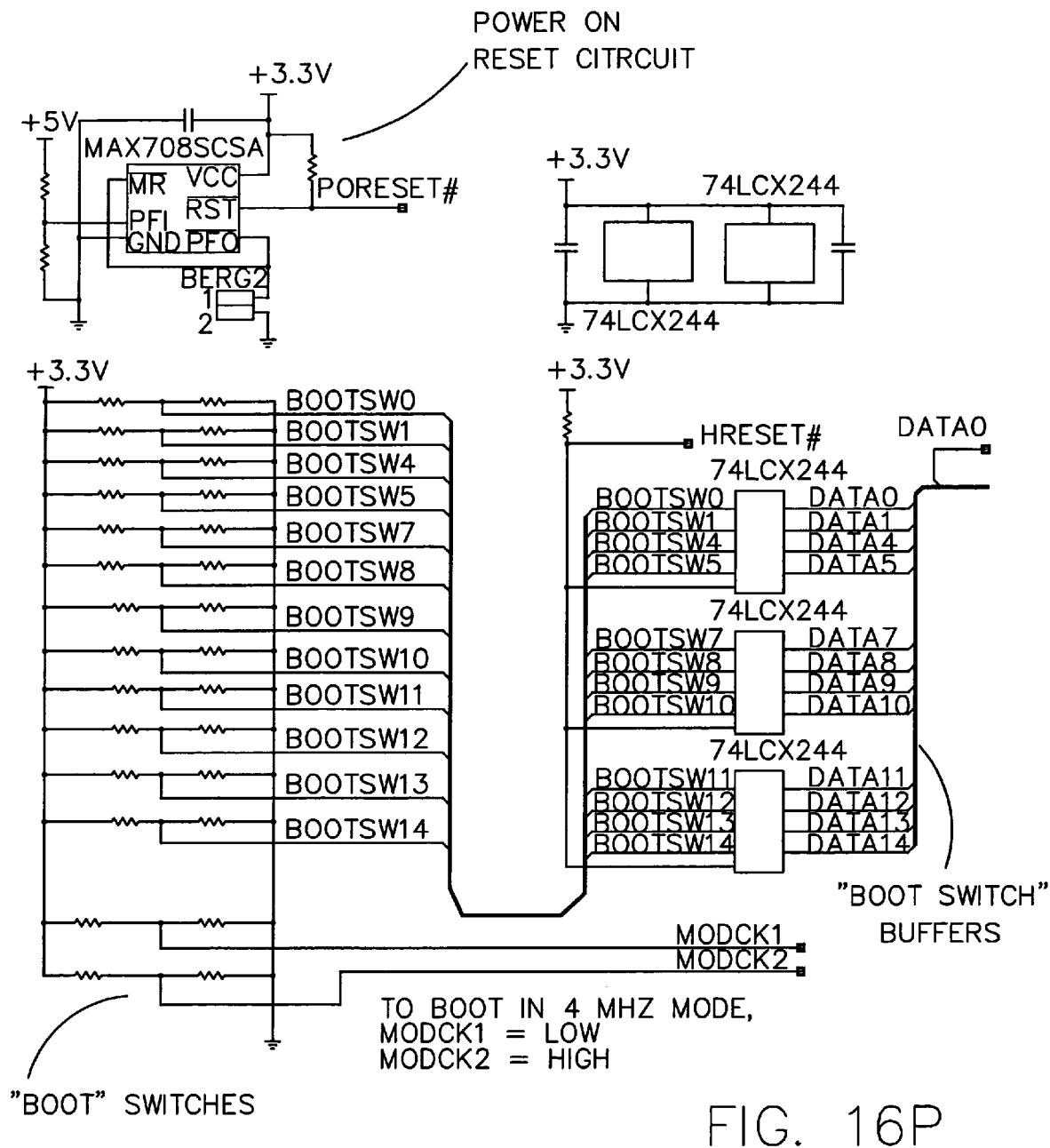
Figure 16Q:
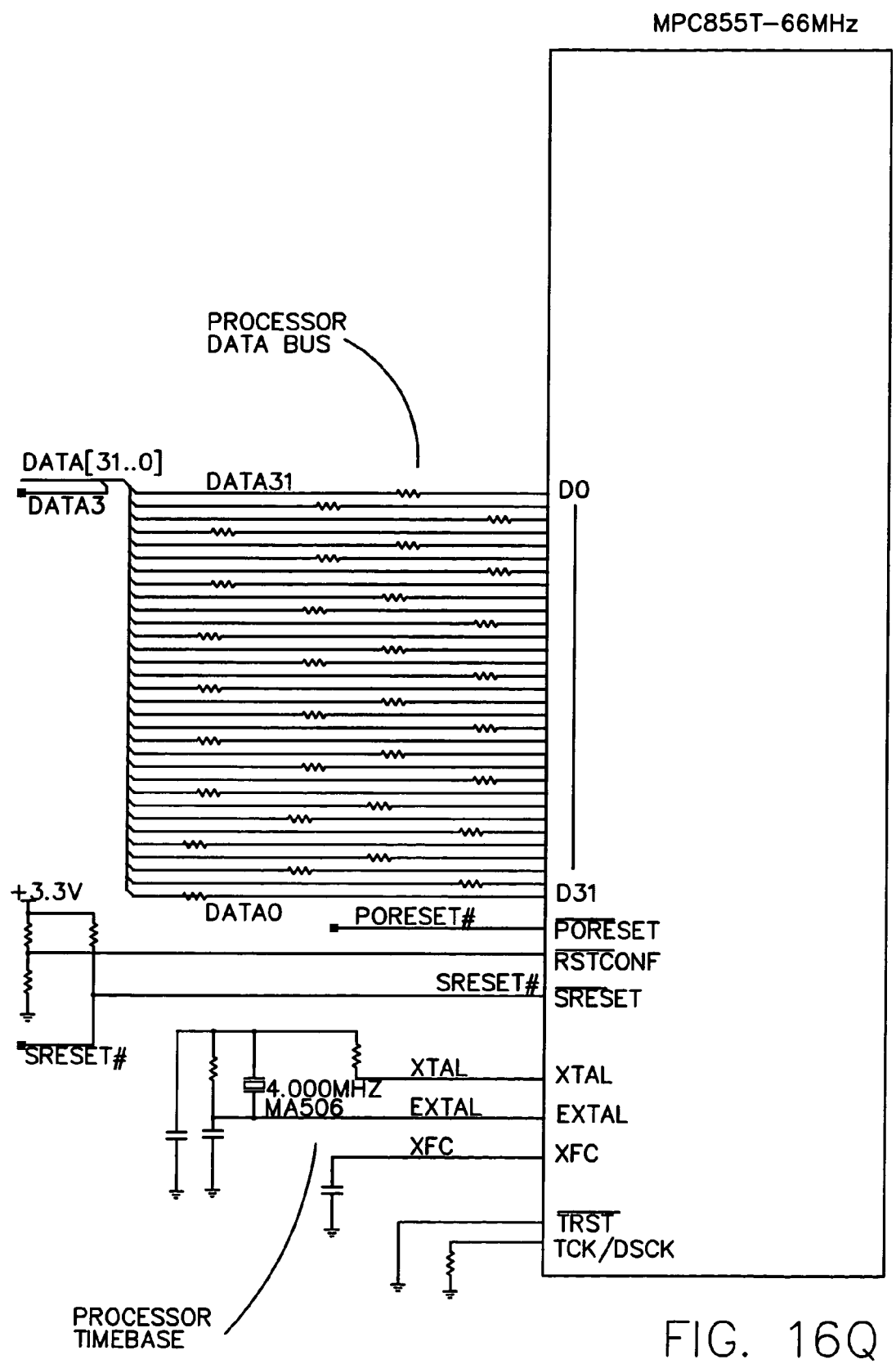
Figure 16R:
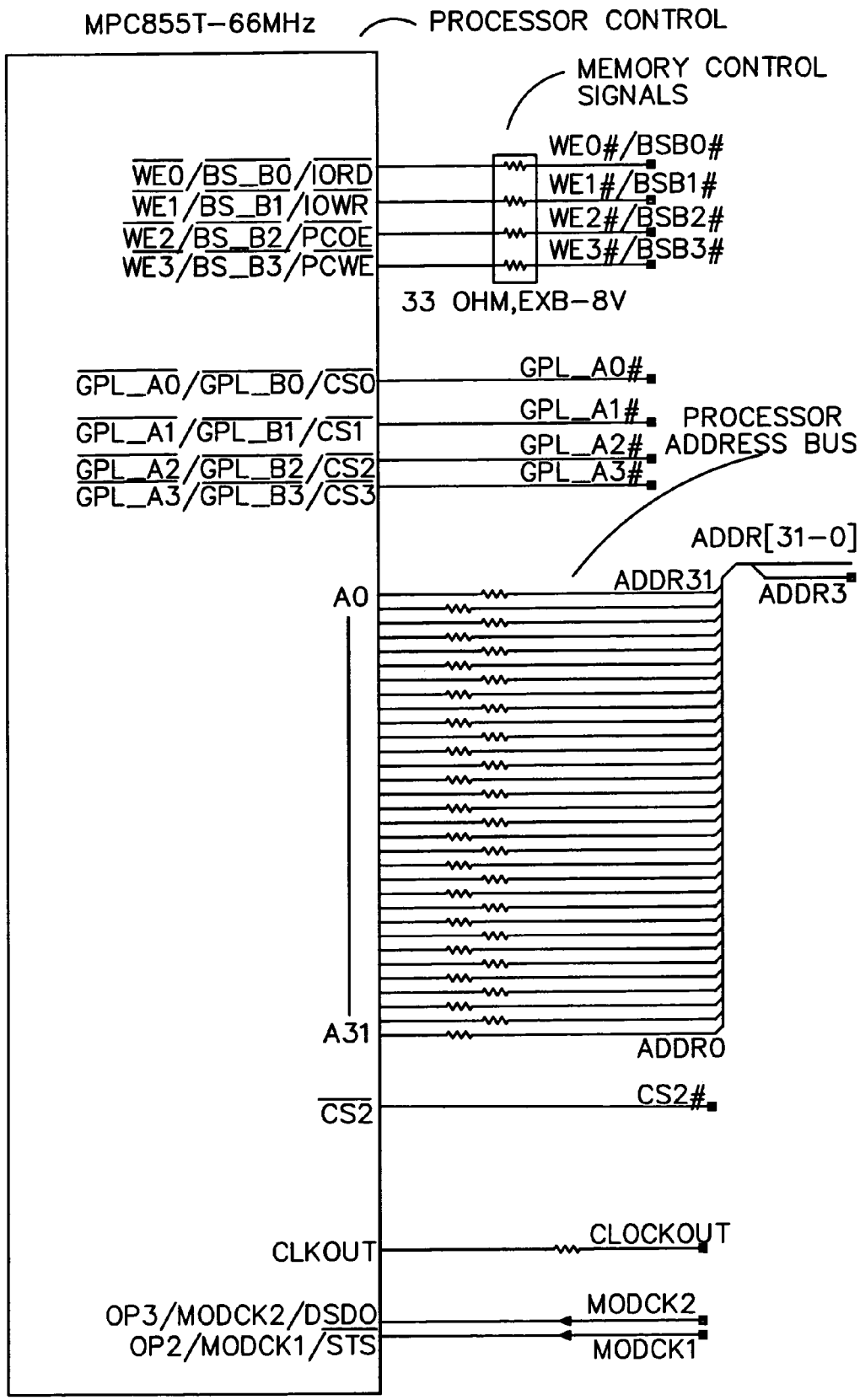
Figure 16S:
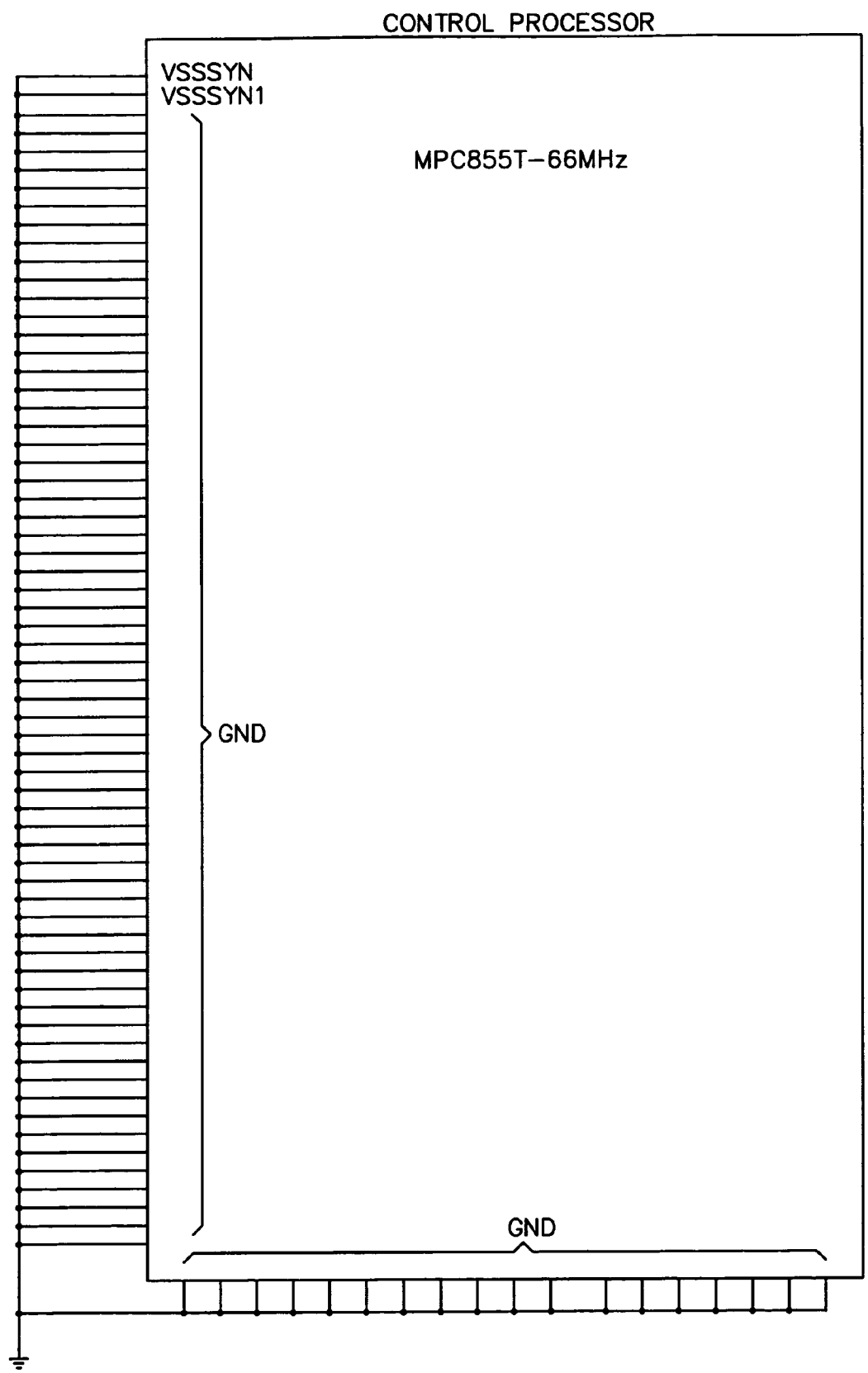
Figure 16T:
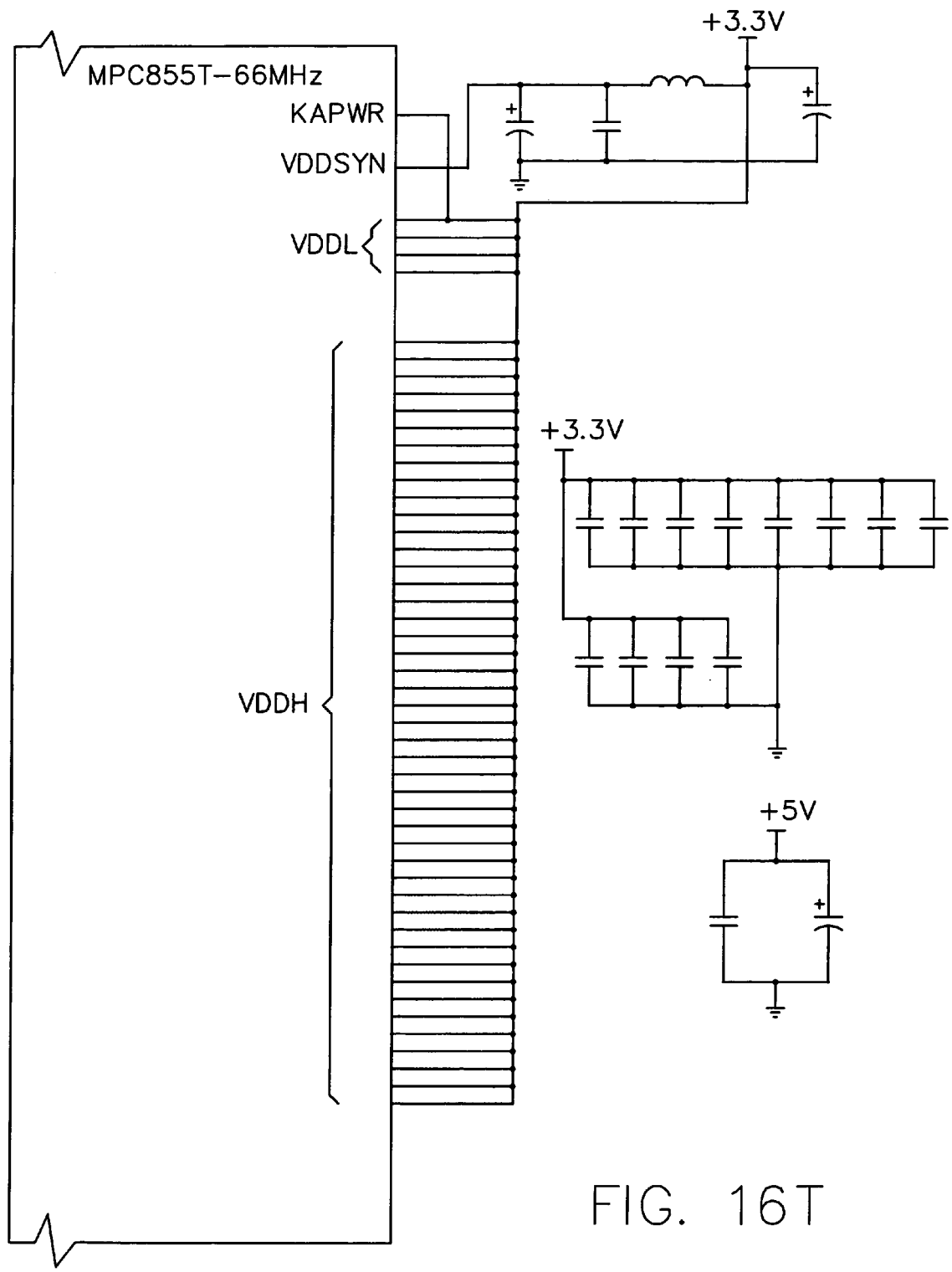
Figure 16U:
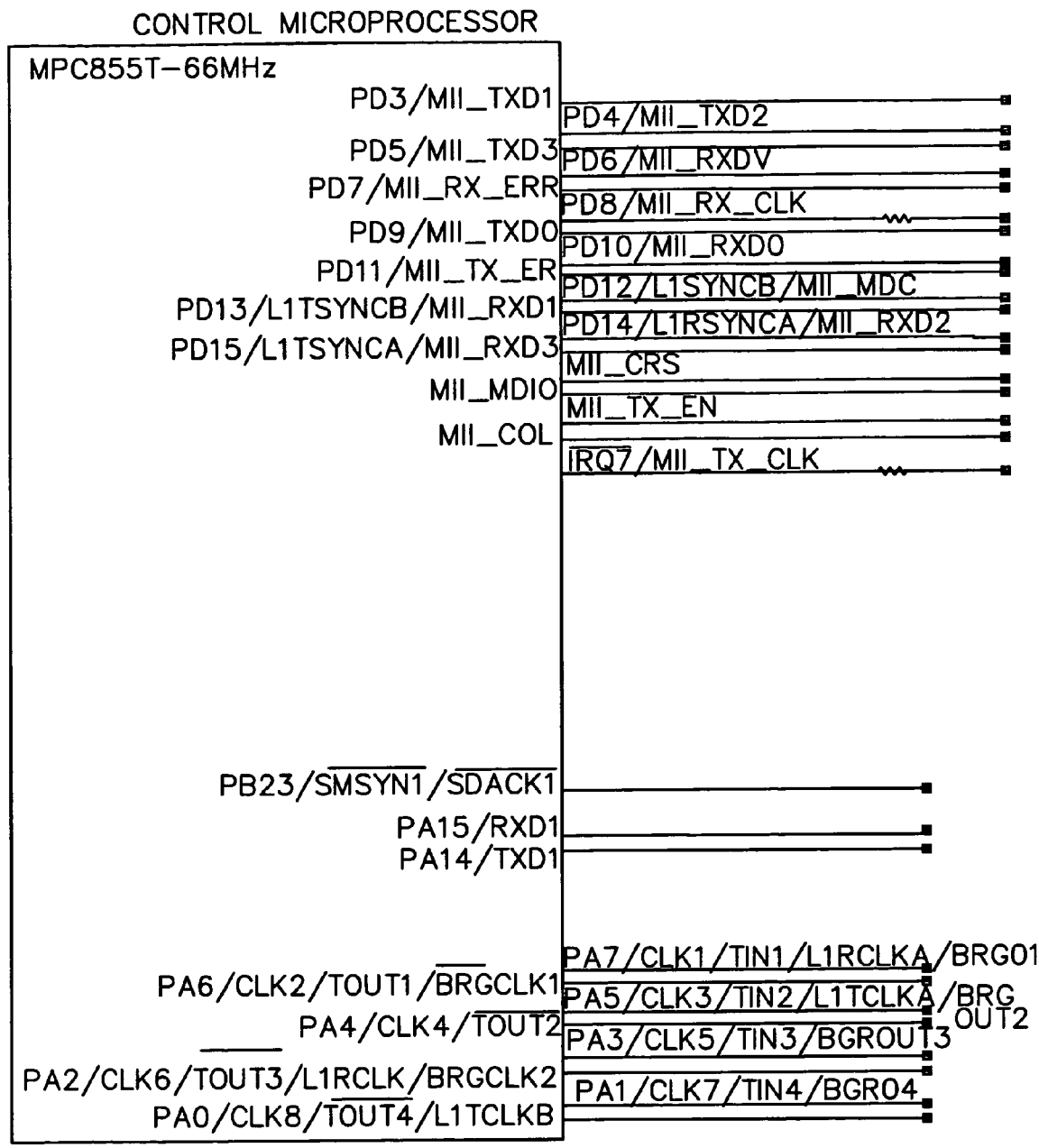
Figure 16V:
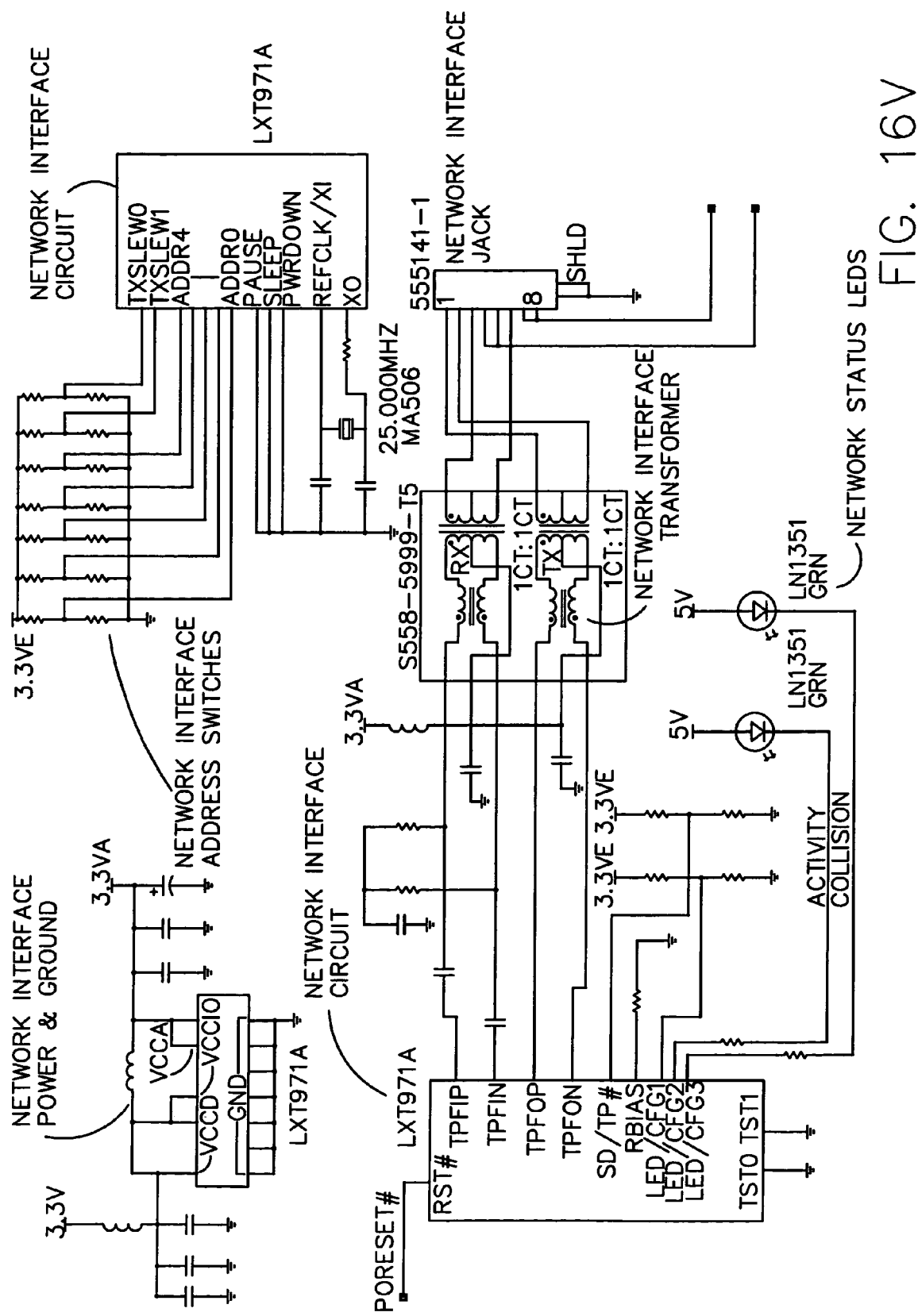
Figure 16W:
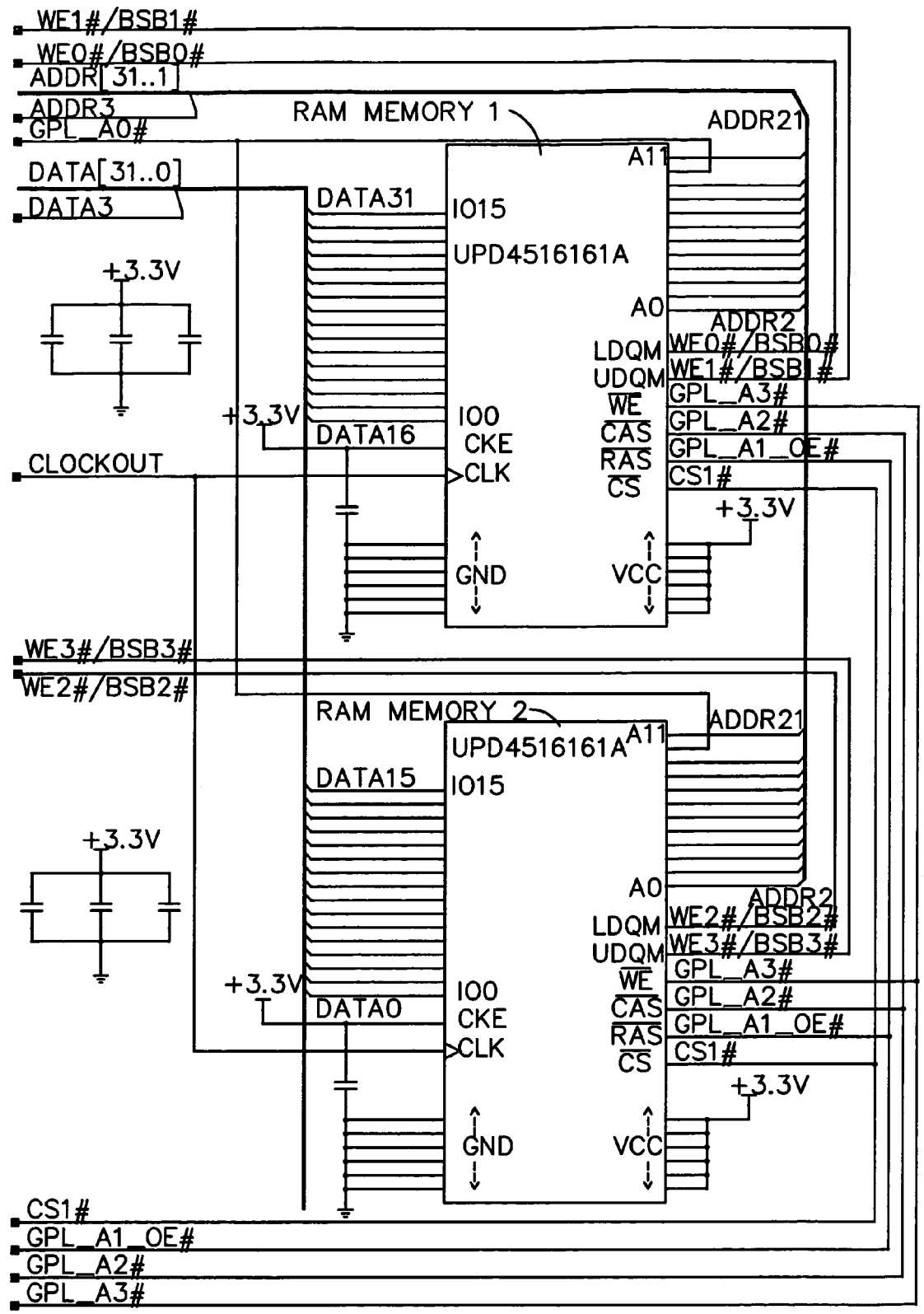
Figure 16X:
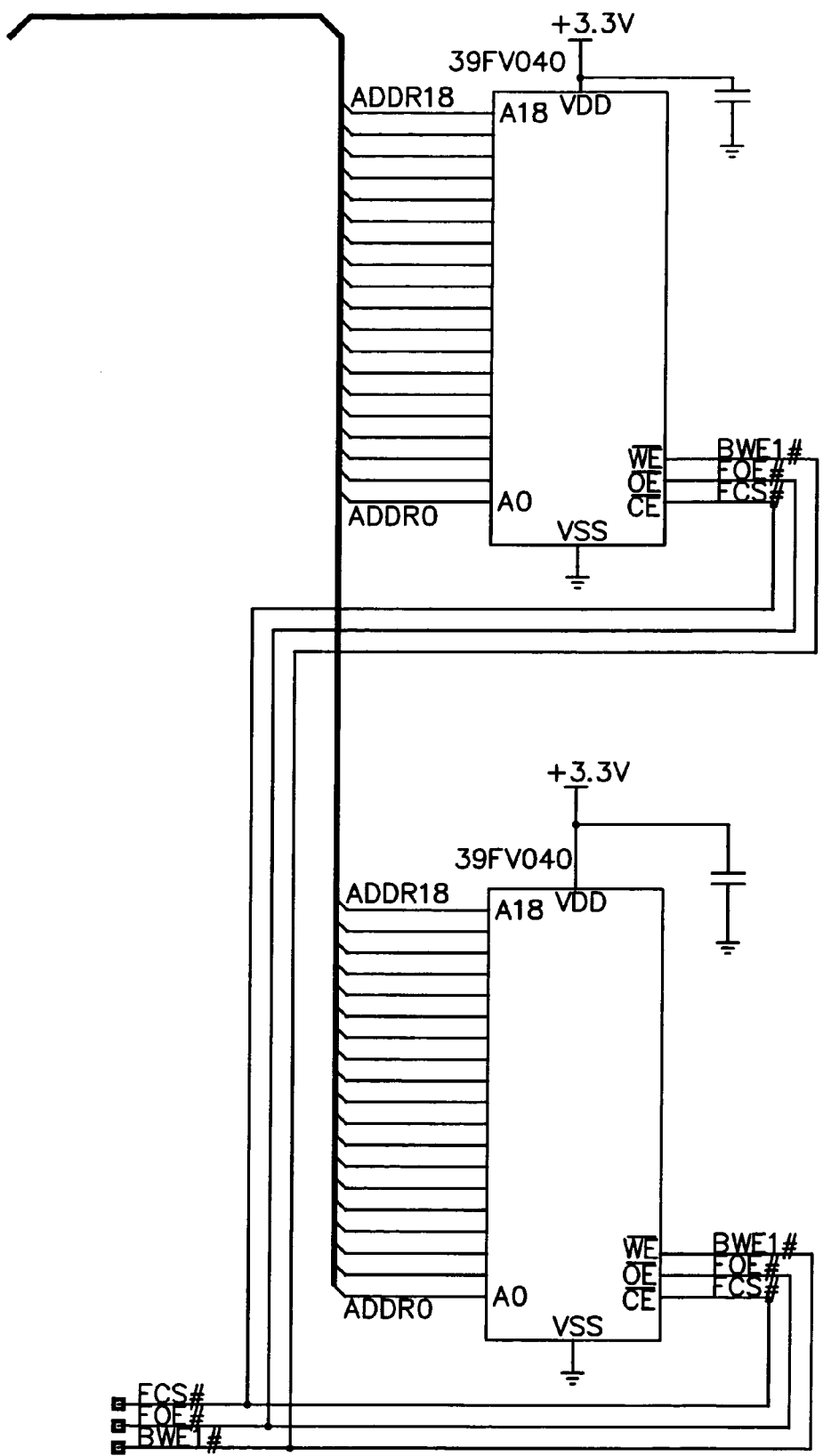
Figure 16Y:
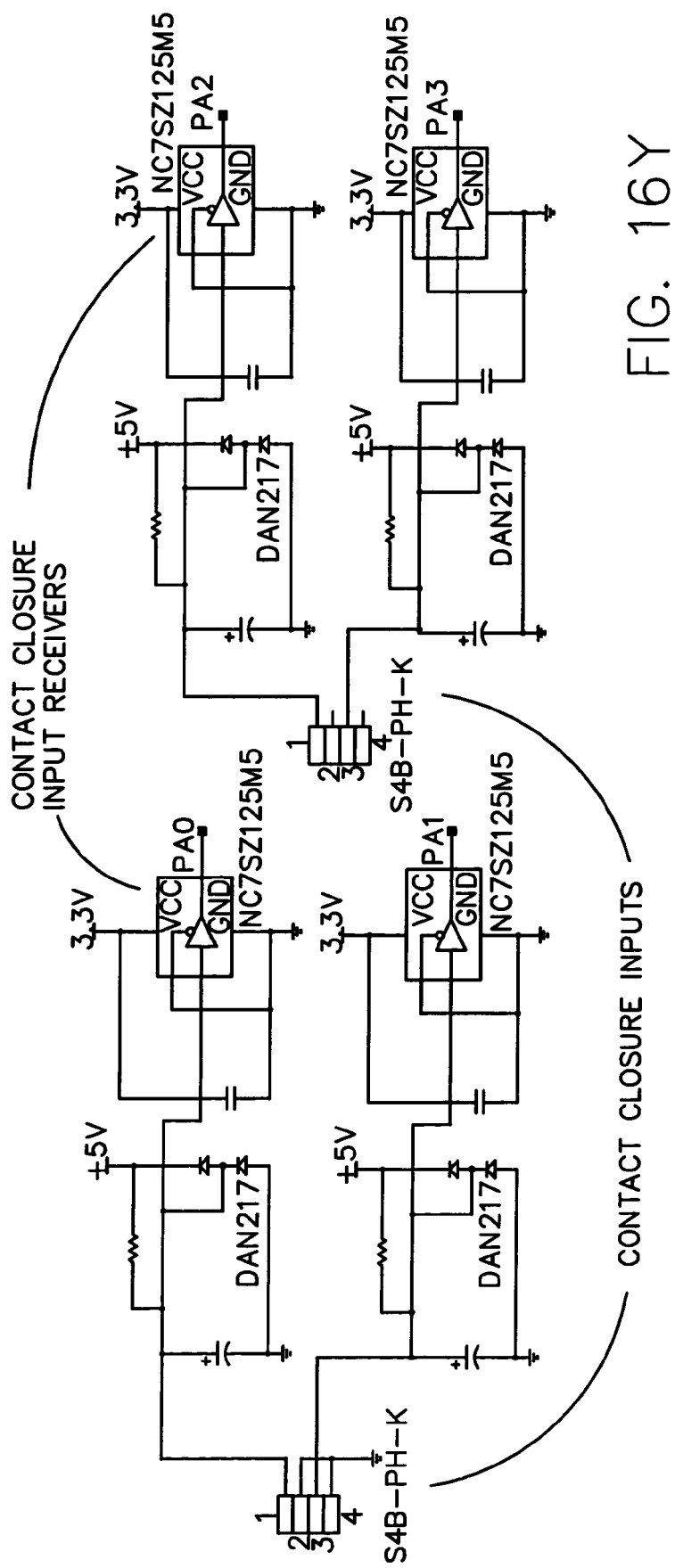
Figure 16Z:
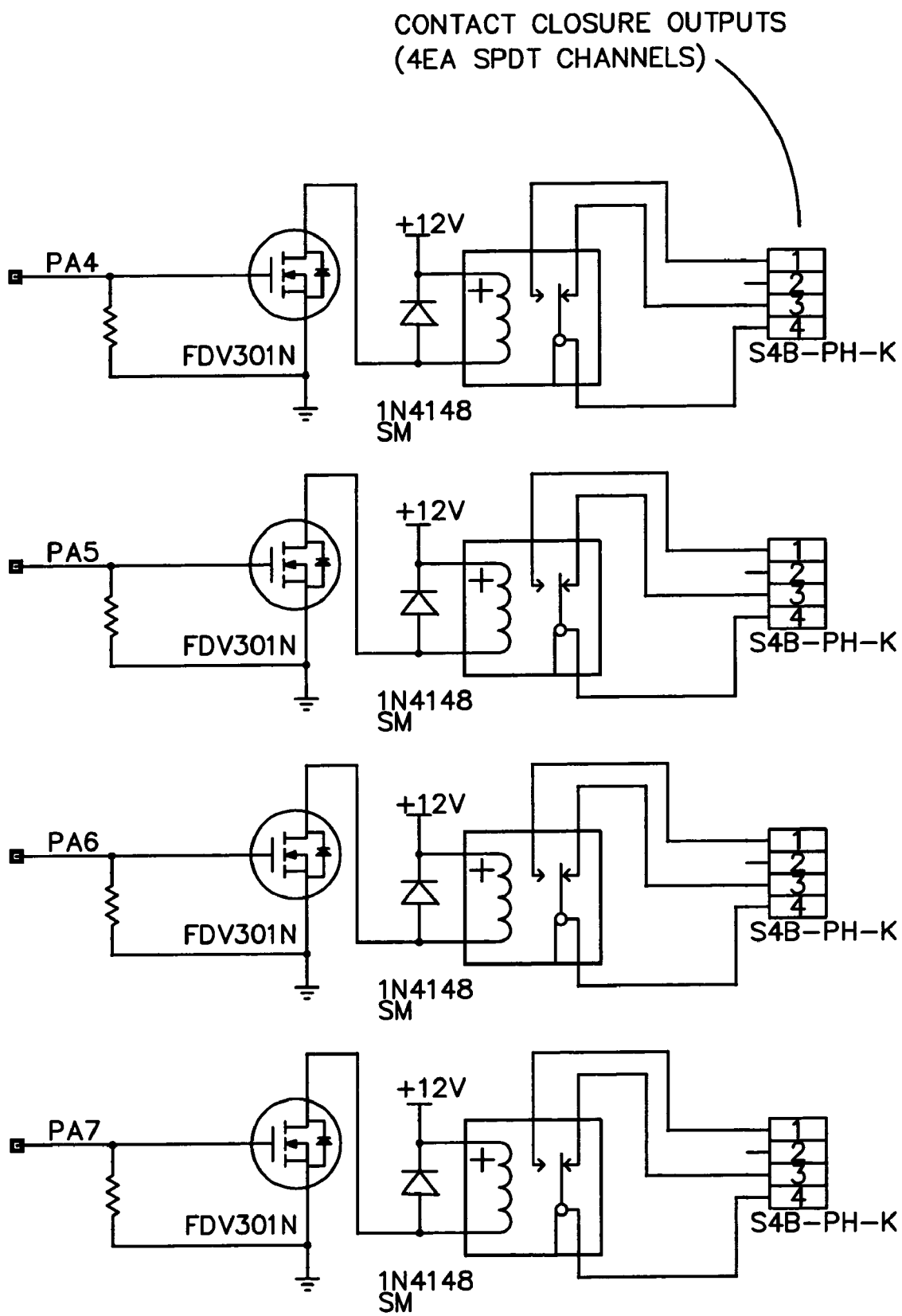
Figure 17A:
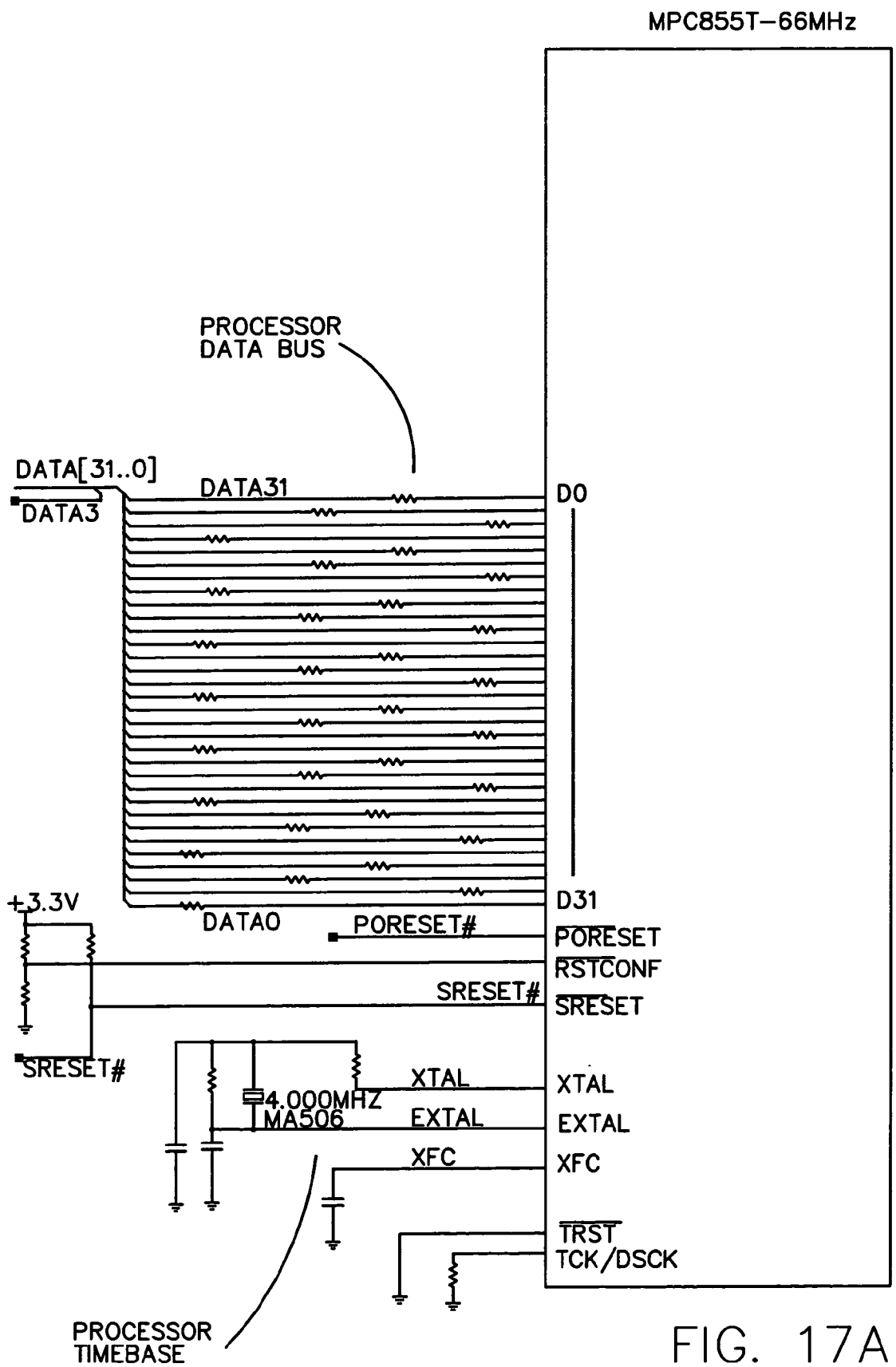
FIGS. 17A to 17M are the schematic of the hardened memory module of the preferred embodiment as shown in FIG. 12.
Figure 17B:
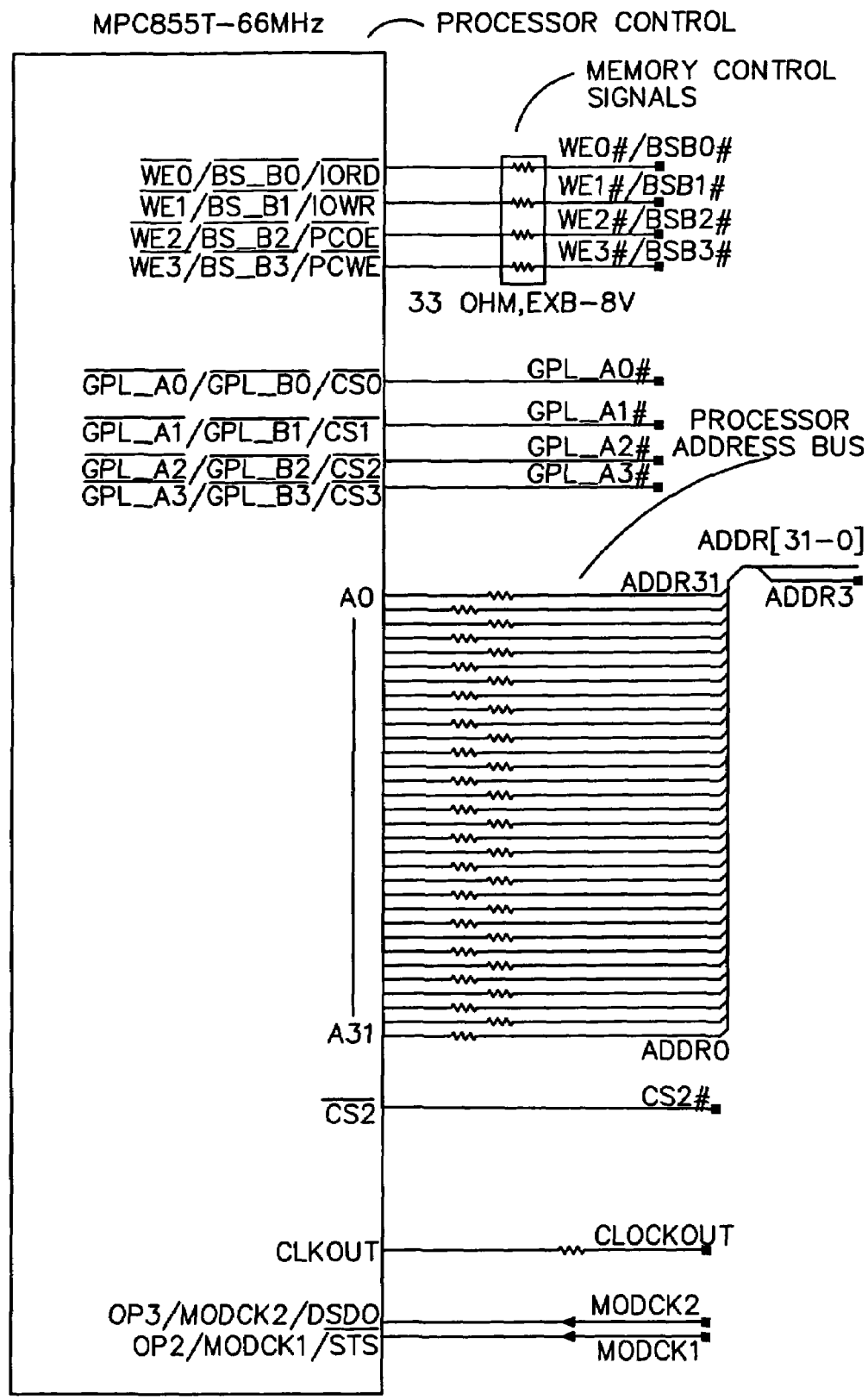
Figure 17C:
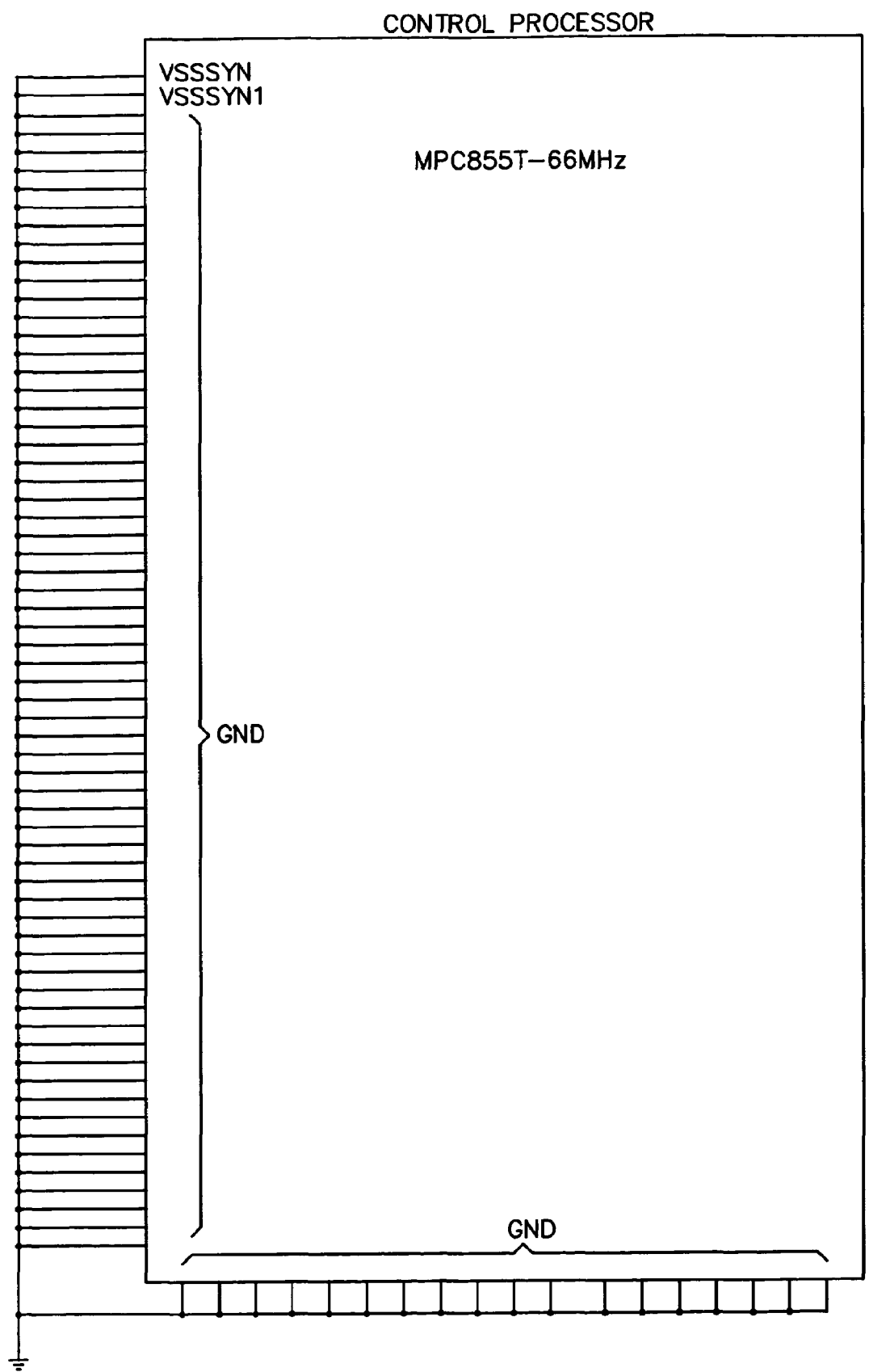
Figure 17D:
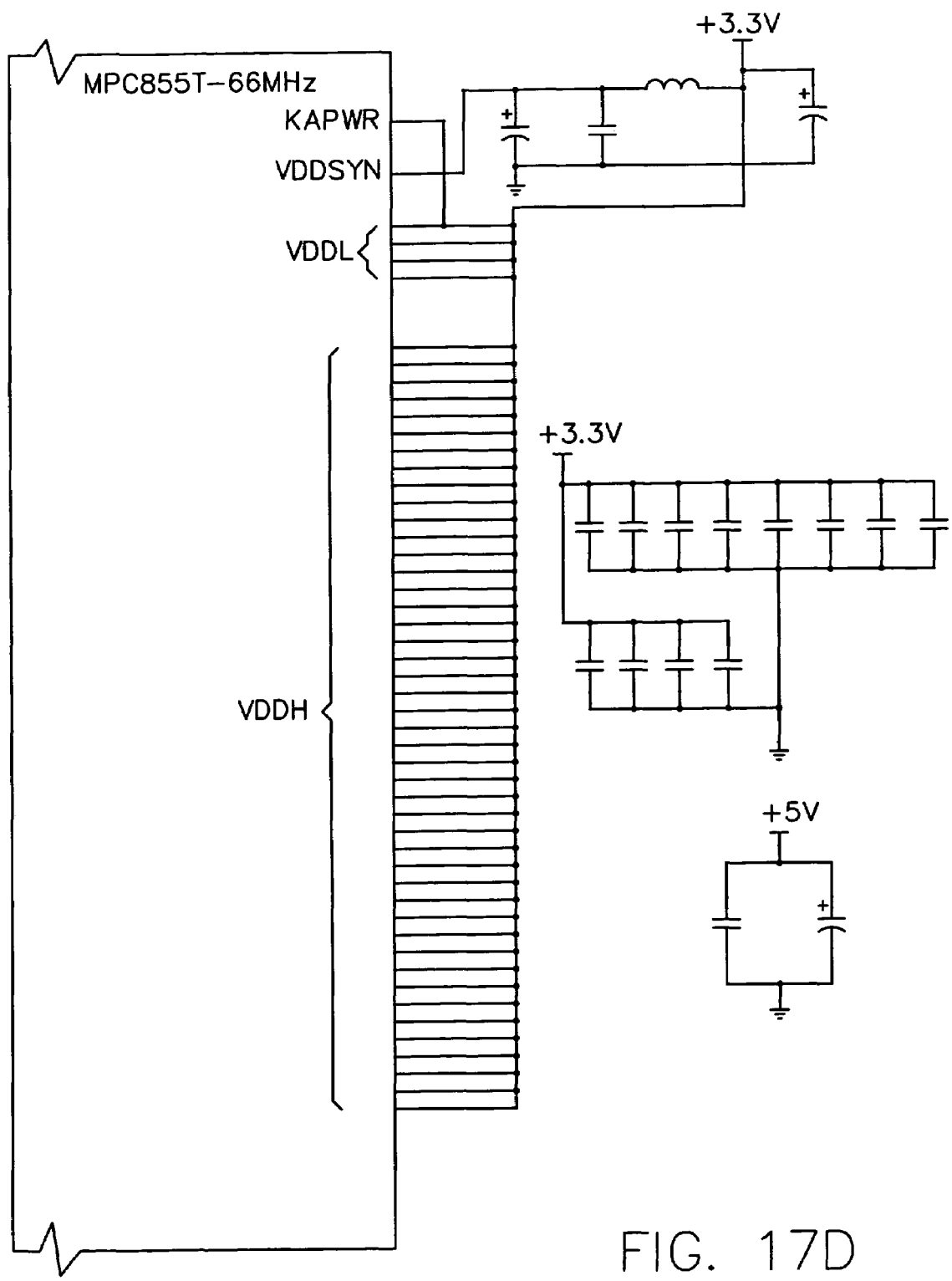
Figure 17E:
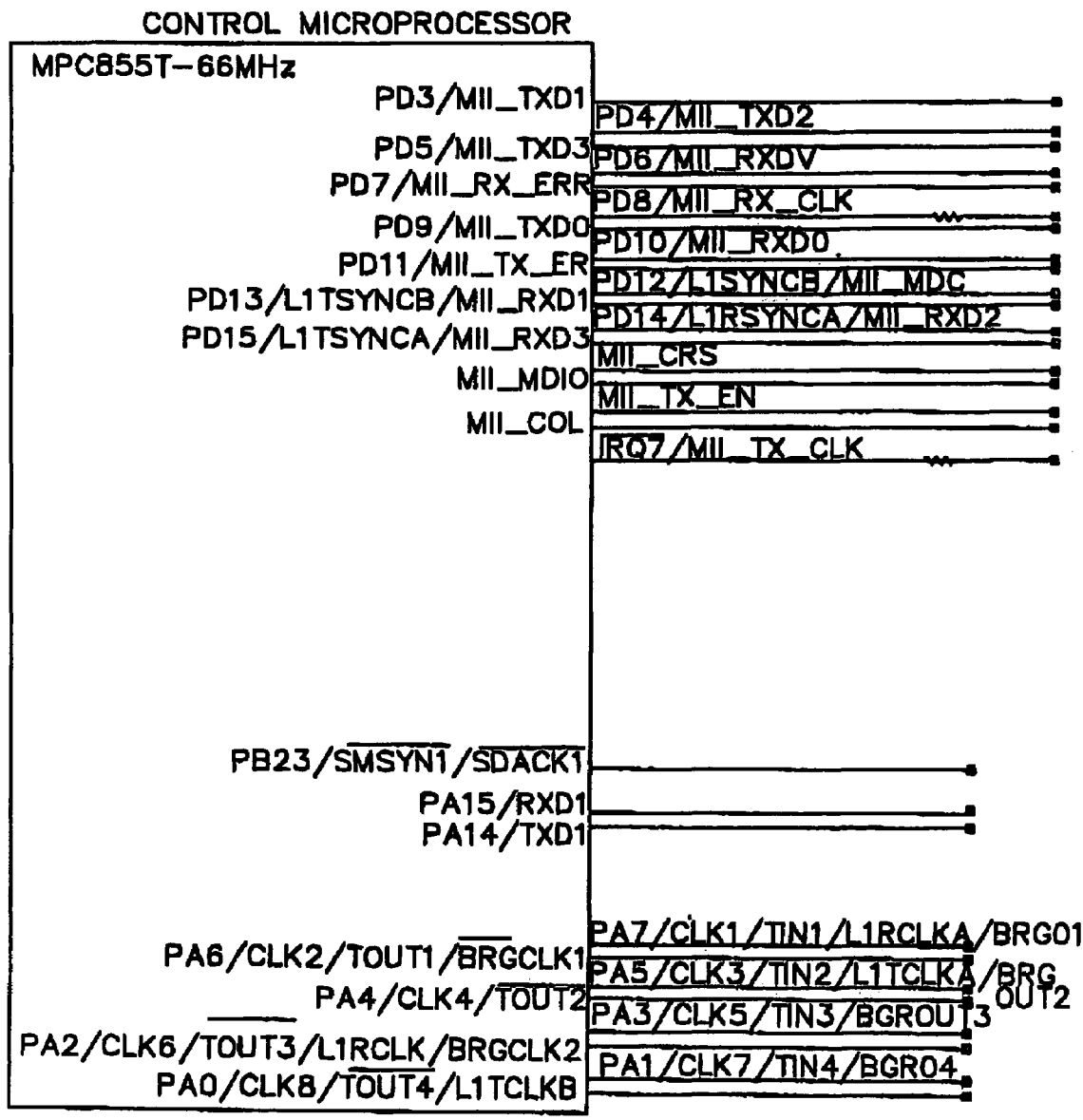
Figure 17F:
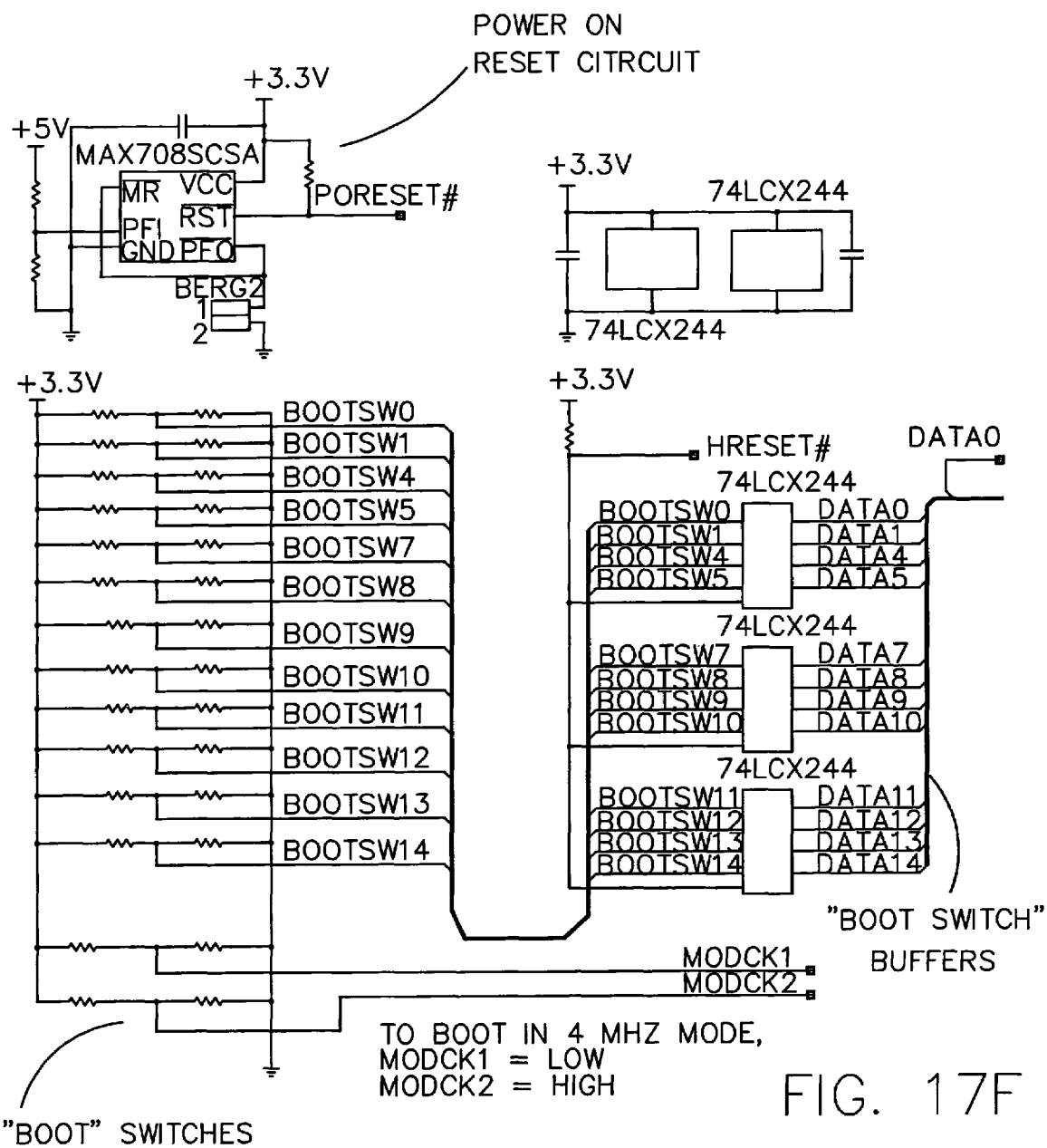
Figure 17G:
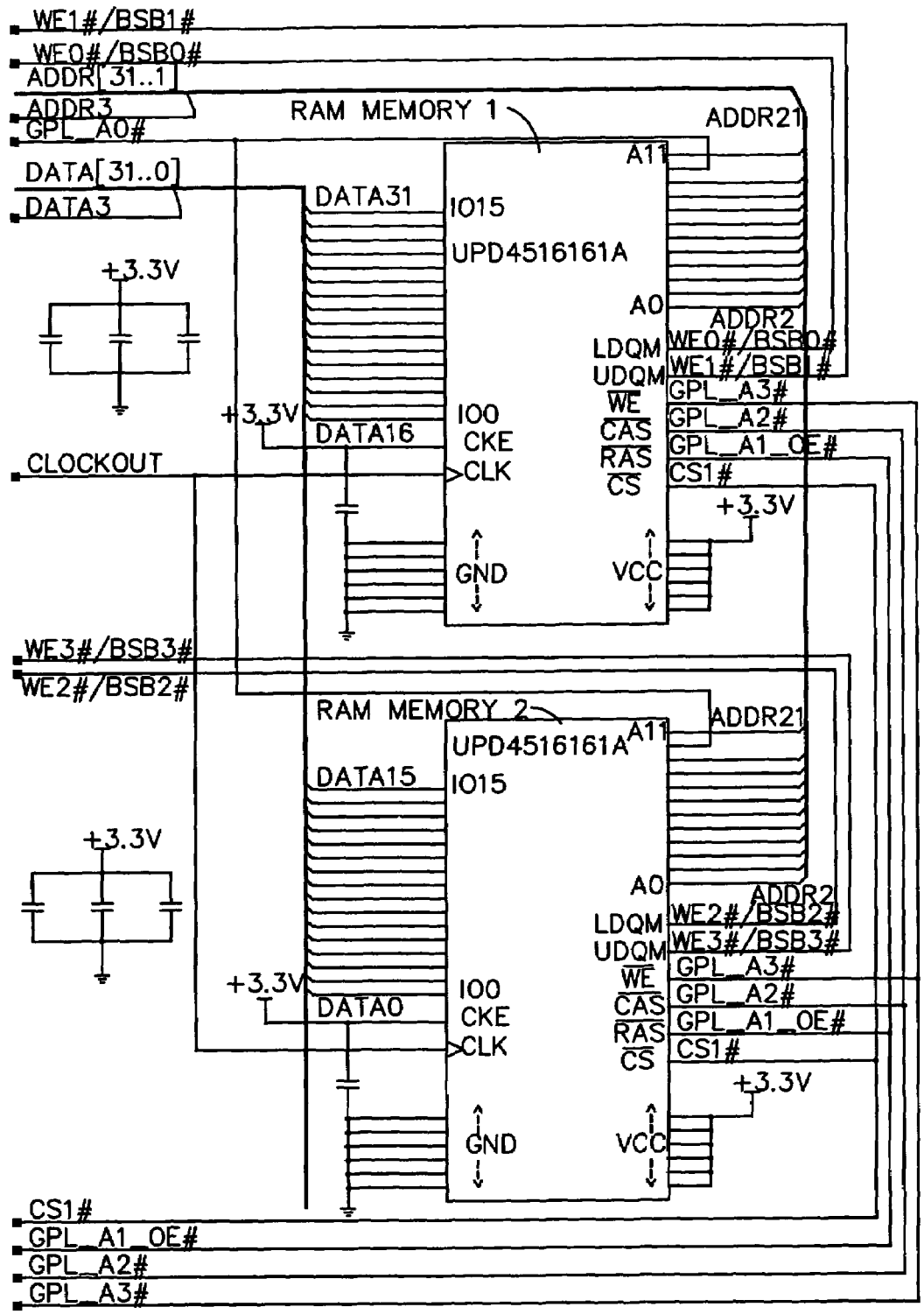
Figure 17H:
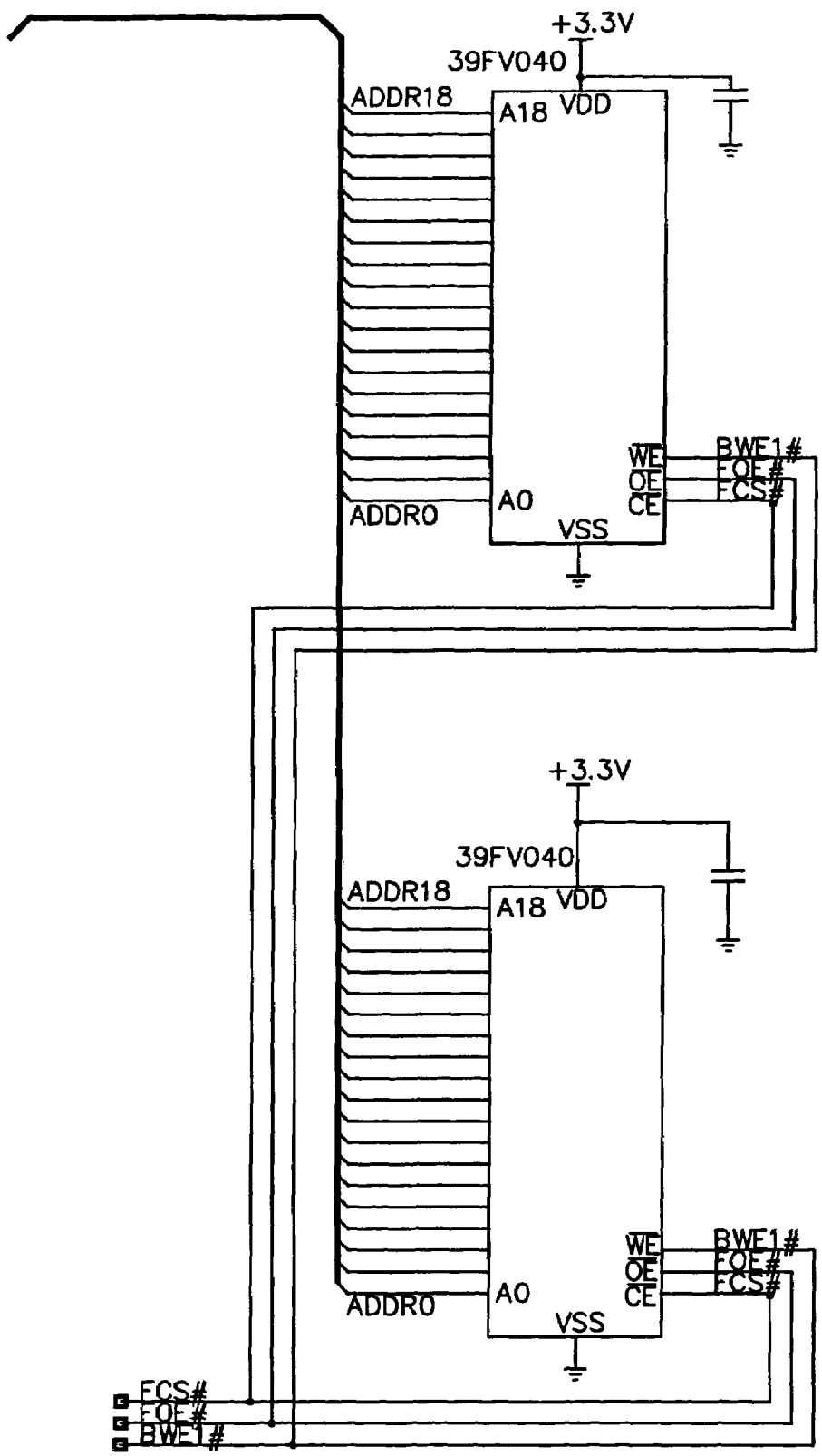
Figure 17I:
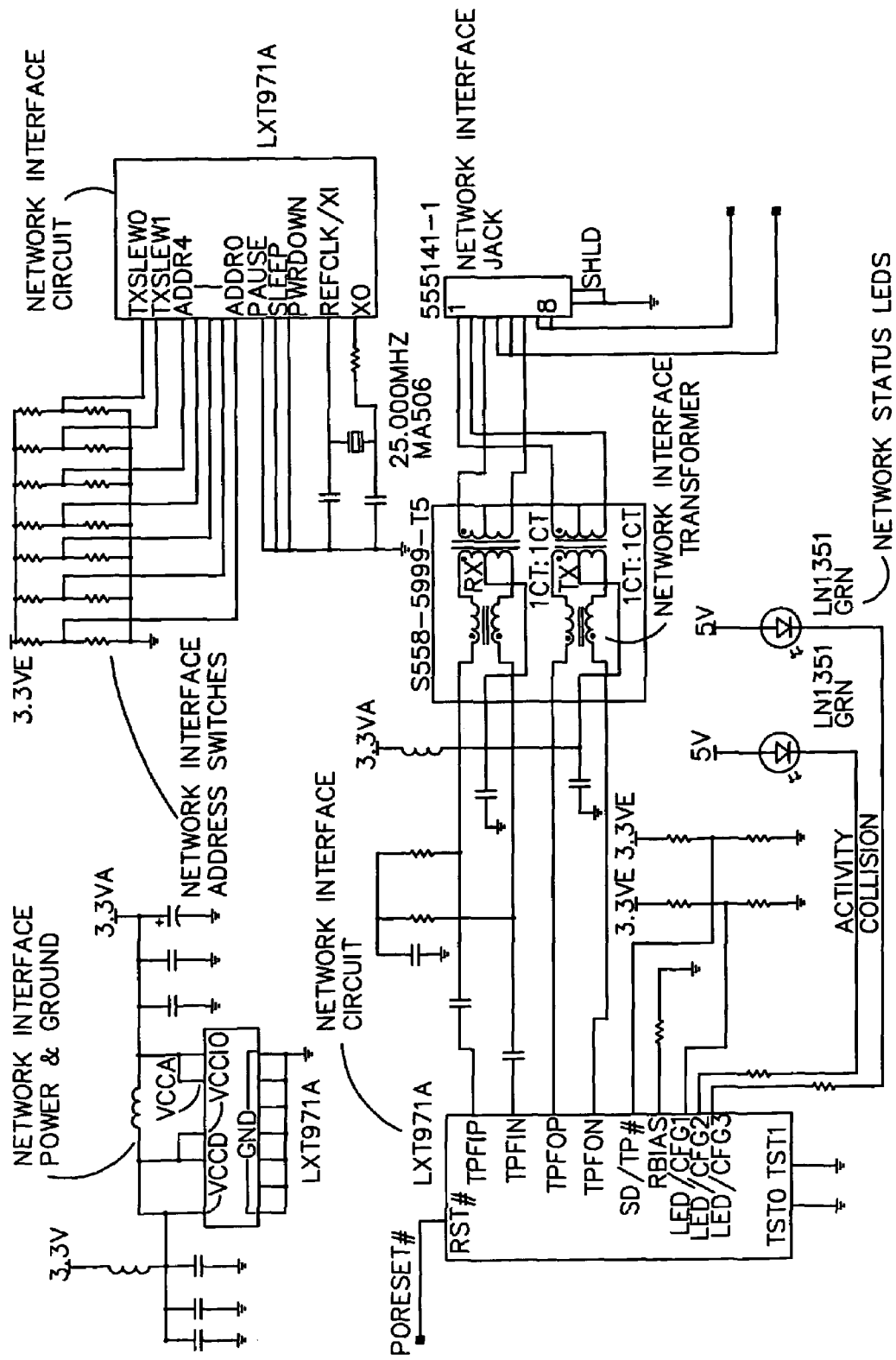
Figure 17J:
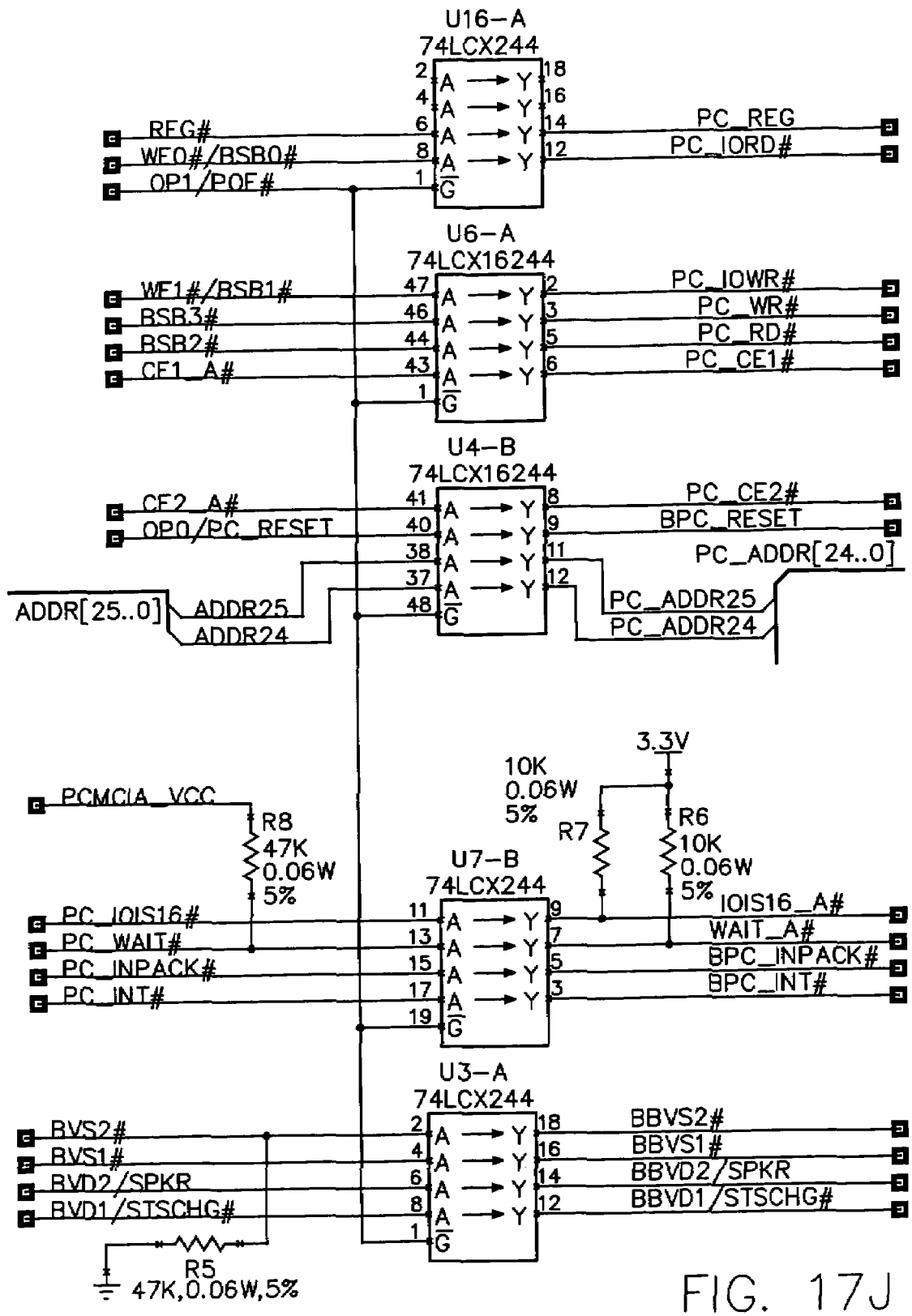
Figure 17K:
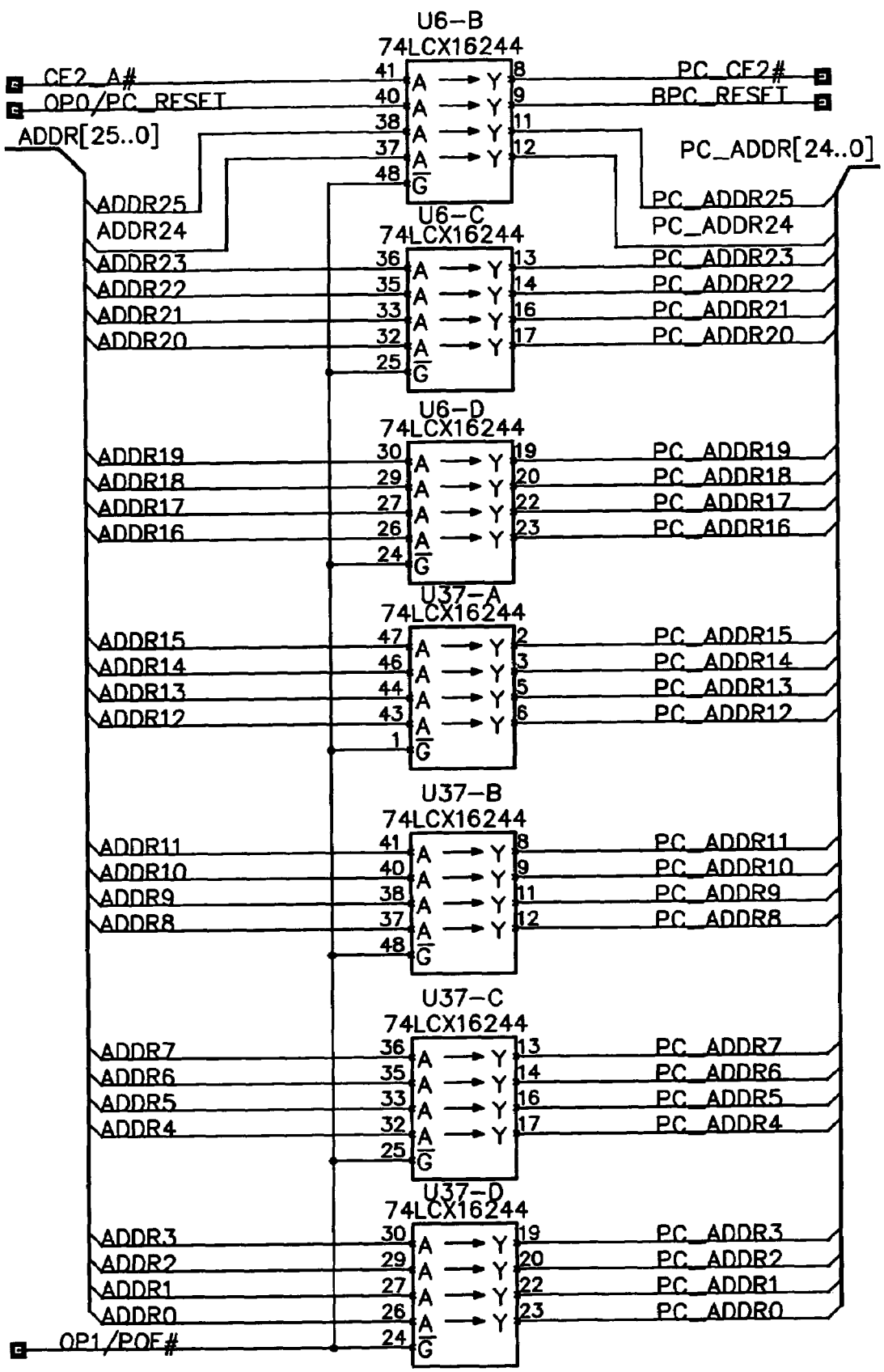
Figure 17L:
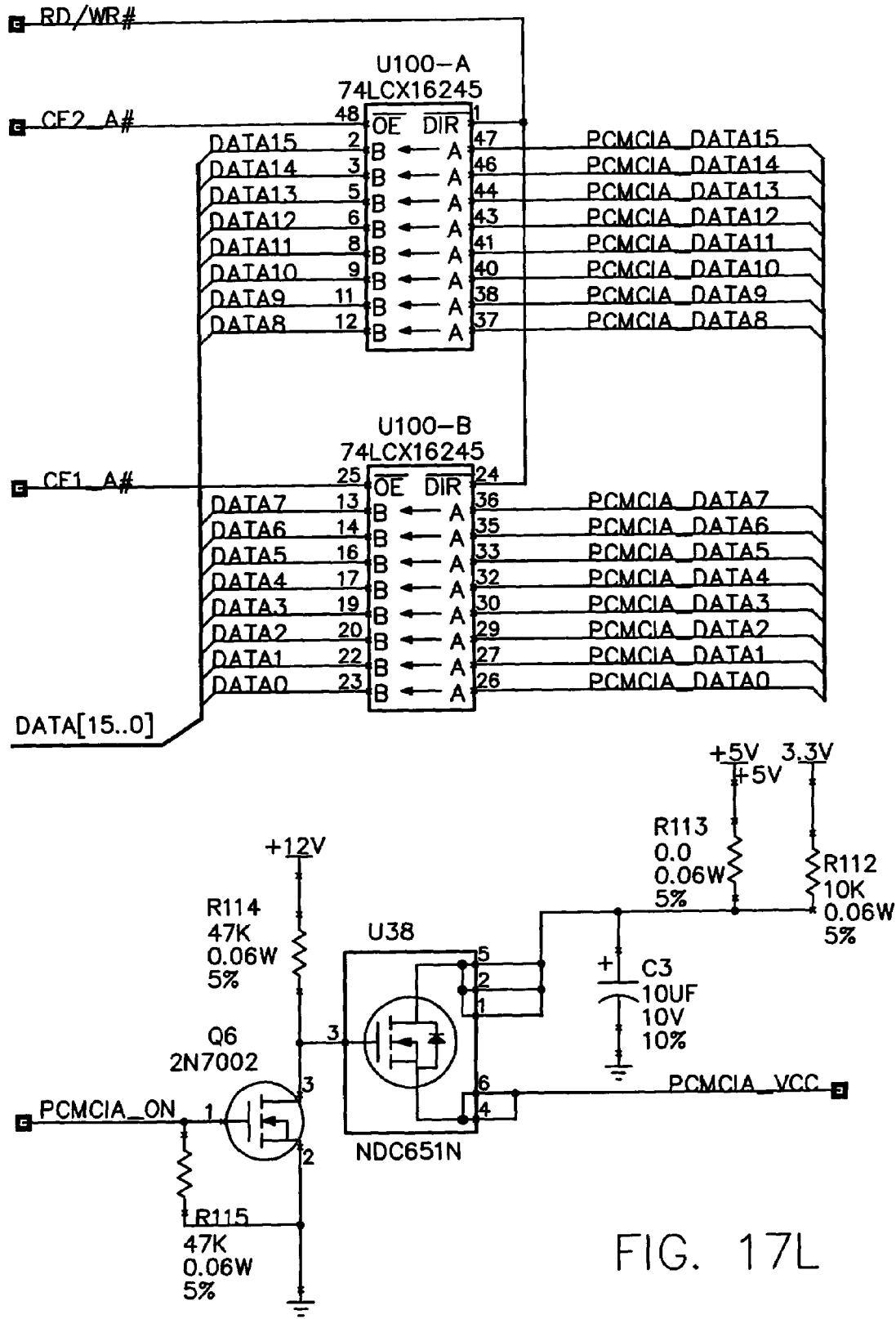
Figure 17M:
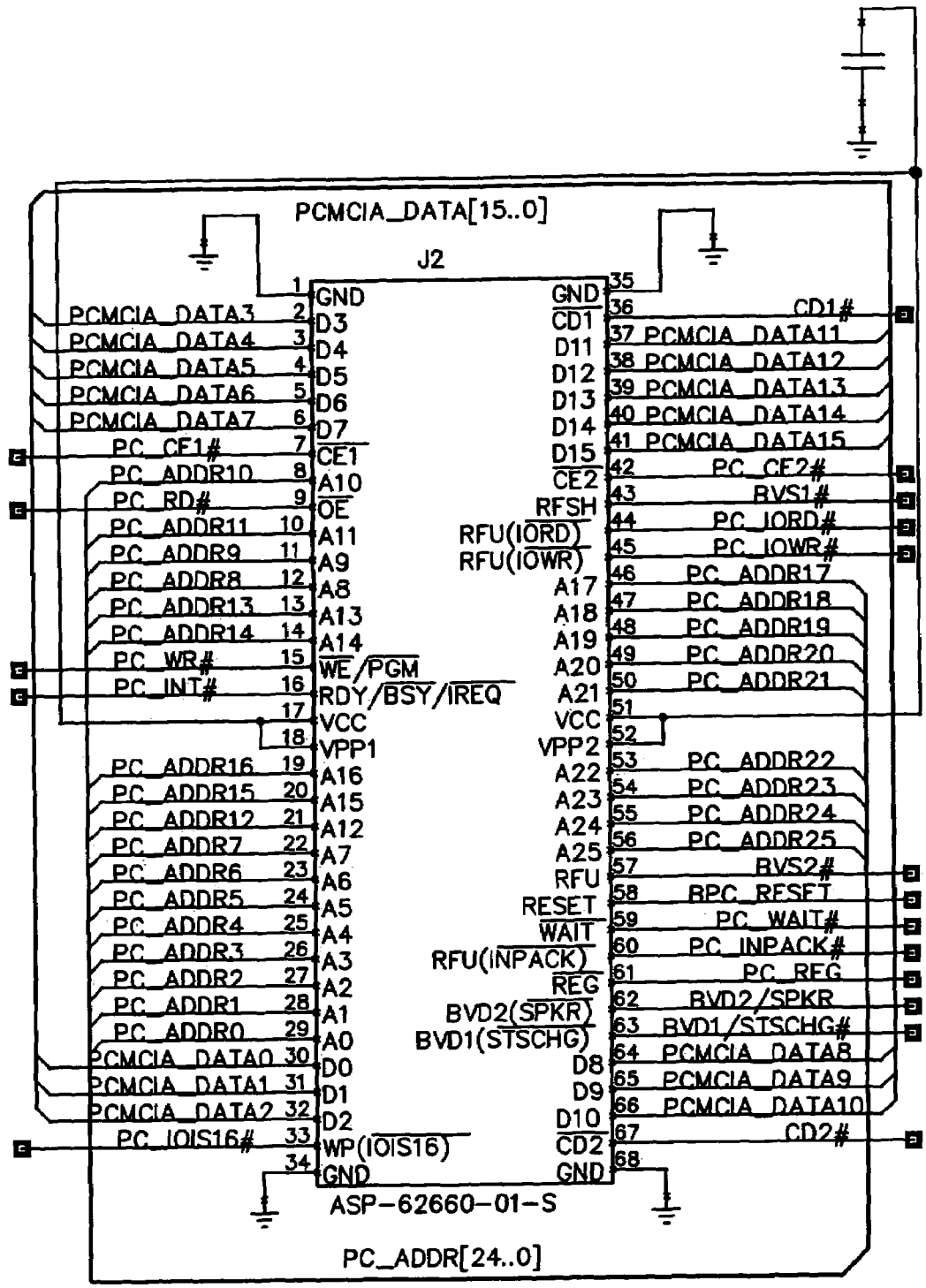

FIGS. 16A to 16Z are the schematic of the support electronics module of the preferred embodiment as shown in FIG. 12.

FIGS. 17A to 17M are the schematic of the hardened memory module of the preferred embodiment as shown in FIG. 12.

While certain features and embodiments of the invention have been described in detail herein, it will be readily understood that the invention includes all modifications and enhancements within the scope and spirit of the following claims.

What is claimed is:

1. An aircraft flight data recorder adapted to be carried aboard an aircraft, the aircraft flight data recorder being adapted to receive from a plurality of sensors located on the aircraft a plurality of digital data signals, at least one of the sensors including a camera adapted to output at least one digital image data signal including respective image data, the image data including at least one of still frame image data and motion video data, the at least one digital image data signal being compressed at the camera by at least one compressor located at the camera, the at least one compressed digital image data signal being encoded in IP format by at least one IP encoder located at the camera, the at least one compressed digital image data signal in IP format being transmitted to the aircraft flight data recorder, the aircraft flight data recorder comprising:
   a nonvolatile memory array; and
   an interface, the interface being adapted to receive the plurality of digital data signals, the interface being adapted to convert into IP format any digital data signal not received by the interface in IP format, a set of digital data in IP format corresponding respectively to each converted digital data signal, the interface being adapted to introduce into the memory array the sets of digital data in IP format, the interface being adapted to receive the at least one compressed digital image data signal in IP format, the interface being adapted to introduce into the memory array at least one set of compressed digital image data in IP format, the at least one set of compressed digital image data in IP format corresponding to the received at least one compressed digital image data signal in IP format.

2. An aircraft flight data recorder according to claim 1 and further comprising:
   apparatus adapted to retrieve from the memory array selected of the at least one set of compressed digital image data in IP format, the selected at least one set of compressed digital image data in IP format being at least one of: transmitted to a recipient external of the aircraft and displayed for viewing.

3. An aircraft flight data recorder according to claim 1 and further comprising:
   a communications interface adapted to transmit to a recipient external of the aircraft at least one of the at least one compressed digital image data signal and the at least one set of compressed digital image data, the at least one set of compressed digital image data being derived from at least one set of compressed digital image data in IP format retrieved from the memory array.

4. An aircraft flight data recorder according to claim 1 and further comprising:
   a processor adapted drive a memory manager to distribute to the memory array the sets of digital data in IP format and the at least one set of compressed digital image data in IP format.

5. An aircraft flight data recorder according to claim 1 and further comprising:
   a multiplexer in communication with the interface, the multiplexer being adapted to combine into a stream of data packets in IP format for transmission to the memory at least one of the following: the plurality of digital data signals, the sets of digital data in IP format corresponding to converted digital data signals, the at least one compressed digital image data signal in IP format, the at least one set of compressed digital image data in IP format.

6. An aircraft flight data recorder according to claim 1 and further comprising:
   the plurality of signals including at least one signal received from a legacy flight data acquisition system.

7. An aircraft flight data recorder according to claim 1 and further comprising:
   a hardened hermetic housing adapted to preserve from damage in the event of an aircraft crash the digital memory array, the preserved digital memory array subsequent to an aircraft crash permitting recovery from the memory array of the sets of digital data in IP format and the at least one set of compressed digital image data in IP format.

8. An aircraft flight data recorder according to claim 7 and further comprising:
   apparatus coupled to the hardened hermetic housing, the apparatus being adapted to generate a locating signal to assist in locating the hardened housing in the event of an aircraft crash.

9. An aircraft flight data recorder according to claim 1 and further comprising:
   the interface being an Ethernet interface adapted to receive the compressed digital image data in IP format.

10. An aircraft including an aircraft flight data recorder according to claim 1.

11. An aircraft flight data recorder adapted to be carried aboard an aircraft, the aircraft flight data recorder being adapted to receive from a plurality of signal generating devices located on the aircraft a plurality of digital data signals, the plurality of signal generating devices including at least one camera adapted to output at least one digital image data signal including respective image data, the image data including at least one of still frame image data and motion video data, the at least one digital image data signal being compressed at the camera by at least one compressor located at the camera, the at least one compressed digital image data signal being encoded in IP format by at least one IP encoder located at the camera, the at least one compressed digital image data signal in IP format being transmitted to the aircraft flight data recorder, the plurality of signal generating devices including at least one legacy flight data recorder system, the at least one legacy flight data recorder system not receiving the at least one compressed digital image data signal in IP format, the at least one legacy flight data recorder system outputting at least one legacy data signal, the aircraft flight data recorder comprising:
   a nonvolatile memory array; and
   an interface, the interface being adapted to receive the plurality of digital data signals, the interface being adapted to convert into IP format any digital data signal not received by the interface in IP format, a set of digital data in IP format corresponding respectively to each converted digital data signal, the interface being adapted to introduce into the memory array the sets of digital data in IP format, the interface being adapted to receive the at least one compressed digital image data signal in IP format, the interface being adapted to introduce into the memory array at least one set of compressed digital image data in IP format, the at least one set of compressed digital image data in IP format corresponding to the received at least one compressed digital image data signal in IP format, the interface being adapted to receive the at least one legacy data signal, the interface being adapted to convert into IP format the at least one legacy data signal, at least one set of legacy data in IP format corresponding respectively to each converted at least one legacy data signal, the interface being adapted to introduce into the memory array the at least one set of legacy data in IP format.

12. An aircraft flight data recorder according to claim 11 and further comprising:
a video decoder adapted to output for display at least one of the at least one compressed digital image data signal in IP format and the at least one set of compressed digital image data in IP format, the at least one set of compressed digital image data in IP format being recalled from the memory array.

13. An aircraft flight data recorder according to claim 11 and further comprising:
an external transmission interface adapted to transmit to a recipient external of the aircraft at least one of the at least one compressed digital image data signal in IP format and the at least one set of compressed digital image data in IP format, the at least one set of compressed digital image data in IP format being recalled from the memory array.

14. An aircraft flight data recorder according to claim 11 and further comprising:
a processor adapted drive a memory manager to distribute to the memory array the sets of digital data in IP format, the at least one set of compressed digital image data in IP format, and the at least one set of legacy data in IP format.

15. An aircraft flight data recorder according to claim 11 and further comprising:
a multiplexer in communication with the interface, the multiplexer being adapted to combine into a stream of data packets in IP format for transmission to the memory at least one of the following: the plurality of digital data signals, the sets of digital data in IP format corresponding to converted digital data signals, the at least one compressed digital image data signal in IP format, the at least one set of compressed digital image data in IP format, the at least one legacy data signal, the at least one set of legacy data in IP format.

16. An aircraft flight data recorder according to claim 11 and further comprising:
a hardened hermetic housing adapted to preserve from damage in the event of an aircraft crash the digital memory array, the preserved digital memory array subsequent to an aircraft crash permitting recovery from the memory array of the sets of digital data in IP format, the at least one set of compressed digital image data in IP format, and the at least one set of legacy data in IP format.

17. An aircraft flight data recorder according to claim 16 and further comprising:
apparatus coupled to the hardened hermetic housing, the apparatus being adapted to generate a locating signal to assist in locating the hardened housing in the event of an aircraft crash.

18. An aircraft flight data recorder according to claim 11 and further comprising:
the interface being an Ethernet interface adapted to receive the compressed digital image data in IP format.

19. An aircraft including an aircraft flight data recorder according to claim 11.

20. An aircraft flight data recorder adapted to be carried aboard an aircraft, the aircraft flight data recorder being adapted to receive at least one legacy flight data signal output by a legacy flight data acquisition system, the at least one legacy flight data signal not including a compressed digital image data signal in IP format, the aircraft flight data recorder being adapted to receive from at least one camera at least one compressed digital image data signal, the aircraft flight data recorder comprising:
a nonvolatile memory array;
an interface, the interface being adapted to receive the at least one legacy flight data signal, the interface being adapted to output at least one set of legacy flight data in IP format, the at least one set of legacy flight data in IP format corresponding to the at least one legacy flight data signal received by the interface, the interface being adapted to introduce to a memory manager the at least one set of legacy flight data in IP format, the interface being adapted to receive the at least one compressed digital image data signal, the interface being adapted to output at least one set of compressed digital image data in IP format, the at least one set of compressed digital image data in IP format corresponding to the at least one compressed digital image data signal received by the interface, the interface being adapted to introduce to a memory manager the at least one set of compressed digital image data in IP format; and
a processor adapted to drive the memory manager to distribute to the memory array the at least one set of legacy flight data in IP format and the at least one set of compressed digital image data in IP format.

21. An aircraft flight data recorder according to claim 20 and further comprising:
a hardened hermetic housing adapted to preserve from damage in the event of an aircraft crash the digital memory array, the preserved digital memory array subsequent to an aircraft crash permitting recovery from the memory array of the at least one set of legacy flight data in IP format and the at least one set of compressed digital image data in IP format.

22. An aircraft flight data recorder according to claim 20 and further comprising:
apparatus coupled to the hardened hermetic housing, the apparatus being adapted to generate a locating signal to assist in locating the hardened housing in the event of an aircraft crash.

23. An aircraft flight data recorder according to claim 20 and further comprising:
the interface being an Ethernet interface adapted to receive the compressed digital image data in IP format.

24. An aircraft including an aircraft flight data recorder according to claim 11.

* * * * *